(12) United States Patent
Ritthipichai et al.

(10) Patent No.: US 11,357,841 B2
(45) Date of Patent: Jun. 14, 2022

(54) EXPANSION OF TUMOR INFILTRATING LYMPHOCYTES WITH POTASSIUM CHANNEL AGONISTS AND THERAPEUTIC USES THEREOF

(71) Applicant: Iovance Biotherapeutics, Inc., San Carlos, CA (US)

(72) Inventors: Krit Ritthipichai, Tampa, FL (US); Michael T. Lotze, Pittsburgh, PA (US)

(73) Assignee: Iovance Biotherapeutics, Inc., San Carlos, CA (US)

(*) Notice: Subject to any disclaimer, the term of this patent is extended or adjusted under 35 U.S.C. 154(b) by 361 days.

(21) Appl. No.: 16/475,925

(22) PCT Filed: Jan. 5, 2018

(86) PCT No.: PCT/US2018/012610
§ 371 (c)(1),
(2) Date: Jul. 3, 2019

(87) PCT Pub. No.: WO2018/129336
PCT Pub. Date: Jul. 12, 2018

(65) Prior Publication Data
US 2019/0374577 A1    Dec. 12, 2019

Related U.S. Application Data

(60) Provisional application No. 62/443,519, filed on Jan. 6, 2017, provisional application No. 62/466,921, filed on Mar. 3, 2017, provisional application No. 62/504,385, filed on May 10, 2017.

(51) Int. Cl.
| | |
|---|---|
| *A61K 35/17* | (2015.01) |
| *A61K 39/00* | (2006.01) |
| *A61P 35/00* | (2006.01) |
| *A61K 31/428* | (2006.01) |
| *C12N 5/0783* | (2010.01) |

(52) U.S. Cl.
CPC ........ *A61K 39/0011* (2013.01); *A61K 31/428* (2013.01); *A61K 35/17* (2013.01); *A61P 35/00* (2018.01); *C12N 5/0638* (2013.01)

(58) Field of Classification Search
CPC .................................................. A61K 39/0011
See application file for complete search history.

(56) References Cited

U.S. PATENT DOCUMENTS

| | | | |
|---|---|---|---|
| 5,126,132 A | 6/1992 | Rosenberg | |
| 5,443,983 A | 8/1995 | Ochoa et al. | |
| 6,352,694 B1 | 3/2002 | June et al. | |
| 6,534,055 B1 | 3/2003 | June et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 7,144,575 B2 | 12/2006 | June et al. | |
| 7,175,843 B2 | 2/2007 | June et al. | |
| 7,232,566 B2 | 6/2007 | June et al. | |
| 7,479,269 B2 | 1/2009 | June et al. | |
| 7,572,631 B2 | 8/2009 | Berenson et al. | |
| 7,943,743 B2 | 5/2011 | Korman et al. | |
| 7,951,365 B2 | 5/2011 | Winqvist et al. | |
| 8,007,785 B2 | 8/2011 | Winqvist et al. | |
| 8,008,449 B2 | 8/2011 | Korman et al. | |
| 8,034,334 B2 | 10/2011 | Dudley et al. | |
| 8,206,702 B2 | 6/2012 | Winqvist et al. | |
| 8,211,424 B2 | 7/2012 | Winqvist et al. | |
| 8,211,425 B2 | 7/2012 | Winqvist et al. | |
| 8,383,099 B2 | 2/2013 | Dudley et al. | |
| 8,617,884 B2 | 12/2013 | Berenson et al. | |
| 9,074,185 B2 | 7/2015 | Dudley et al. | |
| 9,476,028 B2 | 10/2016 | Karlsson-Parra et al. | |
| 9,528,088 B2 | 12/2016 | Berenson et al. | |
| 9,687,510 B2 | 6/2017 | Borrello et al. | |
| 9,844,569 B2 | 12/2017 | Gros et al. | |
| 10,172,887 B2 | 1/2019 | Borrello et al. | |
| 2002/0028808 A1* | 3/2002 | Hansen | A61K 31/542 514/223.2 |
| 2003/0072748 A1 | 4/2003 | Black et al. | |
| 2005/0106717 A1 | 5/2005 | Wilson et al. | |
| 2011/0052530 A1 | 3/2011 | Dudley et al. | |
| 2011/0136228 A1 | 6/2011 | Vera et al. | |

(Continued)

FOREIGN PATENT DOCUMENTS

| | | |
|---|---|---|
| CN | 106244538 A | 12/2016 |
| CN | 106591232 A | 4/2017 |
| CN | 107384867 A | 11/2017 |
| EP | 1539929 B1 | 4/2013 |
| EP | 2925329 A1 | 10/2015 |
| EP | 3188740 A1 | 7/2017 |
| EP | 3365434 A1 | 8/2018 |
| EP | 3368659 A1 | 9/2018 |
| EP | 3487990 A1 | 5/2019 |

(Continued)

OTHER PUBLICATIONS

He et al: "Ex vivo expansion of tumor-infiltrating lymphocytes from nasopharyngeal carcinoma patients for adoptive immunotherapy", Chinese Journal of Cancer, vol. 31, No. 6, Jun. 5, 2012 (Jun. 5, 2012), pp. 287-294) (Year: 2012).*
Chimote et al: ("Selective Inhibition of KCa3.1 Channels Mediates Adenosine Regulation of the Motility of Human T Cells", Journal of Immunology, vol. 191, No. 12, Dec. 2013 (Dec. 2013), pp. 6273-6280) (Year: 2013).*
Ye et al.; Engineered artificial antigen presenting cells facilitate direct and efficient expansion of tumor infiltrating lymphocytes; Journal of Translational Medicine 2011, 9:131, 1-13.
Office Action dated Aug. 19, 2020 for European Patent Application No. 18704639.6, 6 pages.

(Continued)

*Primary Examiner* — Scott Long
(74) *Attorney, Agent, or Firm* — Morgan, Lewis & Bockius LLP

(57) ABSTRACT

Methods of expanding tumor infiltrating lymphocytes (TILs) using a potassium channel agonist, such as a $K_{Ca}3.1$ (IK channel) agonist, and uses of such expanded TILs in the treatment of diseases such as cancer are disclosed herein.

17 Claims, 25 Drawing Sheets

Specification includes a Sequence Listing.

(56) References Cited

U.S. PATENT DOCUMENTS

| | | |
|---|---|---|
| 2012/0244133 A1 | 9/2012 | Rosenberg et al. |
| 2013/0102075 A1 | 4/2013 | Vera et al. |
| 2013/0115617 A1 | 5/2013 | Wilson |
| 2014/0377739 A1 | 12/2014 | Welch et al. |
| 2015/0125466 A1* | 5/2015 | Krogsgaard ..... G01N 33/57407 424/144.1 |
| 2015/0175966 A1 | 6/2015 | Vera et al. |
| 2015/0320798 A1 | 11/2015 | Borrello et al. |
| 2016/0010058 A1 | 1/2016 | Gros et al. |
| 2016/0208216 A1 | 7/2016 | Vera et al. |
| 2016/0215262 A1 | 7/2016 | Powell |
| 2017/0044496 A1 | 2/2017 | Sarnaik et al. |
| 2017/0081635 A1 | 3/2017 | Sarnaik et al. |
| 2017/0107490 A1 | 4/2017 | Maeurer |
| 2017/0114321 A1 | 4/2017 | Berenson et al. |
| 2017/0152478 A1 | 6/2017 | Rosenberg et al. |
| 2017/0258838 A1 | 9/2017 | Borrello et al. |
| 2018/0148690 A1 | 5/2018 | Gros et al. |
| 2018/0187150 A1 | 7/2018 | De Larichaudy |
| 2019/0000070 A1 | 1/2019 | De Larichaudy |
| 2019/0062706 A1 | 2/2019 | Almaasbak et al. |
| 2019/0136186 A1 | 5/2019 | Germeroth et al. |

FOREIGN PATENT DOCUMENTS

| | | |
|---|---|---|
| WO | WO 2013/057500 A1 | 4/2013 |
| WO | WO 2013/088147 A1 | 6/2013 |
| WO | WO 2013/173835 A1 | 11/2013 |
| WO | WO 2013/188427 A1 | 12/2013 |
| WO | 2015/157636 A1 | 10/2015 |
| WO | 2015189356 A1 | 12/2015 |
| WO | WO 2015/189357 A1 | 12/2015 |
| WO | WO 2016/053338 A1 | 4/2016 |
| WO | WO 2016/096903 A1 | 6/2016 |
| WO | 2017048614 A1 | 3/2017 |
| WO | 2018005712 A1 | 1/2018 |
| WO | WO 2018/081473 A1 | 5/2018 |
| WO | 2018102761 A1 | 6/2018 |
| WO | 2018170188 A2 | 9/2018 |
| WO | 2018/182817 | 10/2018 |

OTHER PUBLICATIONS

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):0F1-0F9 (2013).

Chimote Ameet A et al: "Selective Inhibition of KCa3.1 Channels Mediates Adenosine Regulation of the Motility of Human T Cells", Journal of Immunology, vol. 191, No. 12, Dec. 2013 (Dec. 2012), pp. 6273-6280.

Chimote Ameet A et al, "Kv1.3 Channels Mark Functionally Competent CD8(+) Tumor-Infiltrating Lymphocytes in Head and Neck Cancer", Cancer Research,vol. 77, No. 1, Jan. 1, 2017 (Jan. 1, 2017), p. 53-61.

Donia M, et al. Simplified protocol for clinical-grade tumor-infiltrating lymphocyte manufacturing with use of the Wave bioreactor. Cytotherapy. Aug. 2014;16(8):1117-20.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley et al., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley et al., "Generation of Tumor-Infiltrating Lymphocyte Cultures for Use in Adoptive Transfer Therapy for Melanoma Patients," J Immunother., 2003: 26(4): 332-342.

Dudley, et al., "Cancer Regression and Autoimmunity in Patients After Clonal Repopulation with Antitumor Lymphocytes", Science, Oct. 2002, 298, 850-54.

Eil Robert et al, "Ionic immune suppression within the tumour microenvironment limits T cell effector function", Nature (LONDON), vol. 537, No. 7621, Sep. 22, 2016 (Sep. 22, 2016), p. 539-543+17PP.

International Search Report and Written Opinion for International Patent Application No. PCT/US2018/012633 dated May 25, 2018, 11 pages.

International Search Report for International Patent Application No. PCT/US2018/012610, 6 pages.

Jia He et al: "Ex vivo expansion of tumor-infiltrating lymphocytes from nasopharyngeal carcinoma patients for adoptive immunotherapy", Chinese Journal of Cancer, vol. 31, No. 6, Jun. 5, 2012 (Jun. 5, 2012), pp. 287-294.

Jin et al., "Simplified method of the growth of human tumor infiltrating lymphocytes in gas-permiable flasks to numbers needed for patient treatment", J. Immunotherapy, 2012, 35:283-292.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65.

Ritthipichai Krit et al, "K+ Channel Activation Promotes Tumor infiltrating Lymphocyte (TIL) Expansion and Enhances Expression of CCR7", Journal of Immunology, vol. 198, No. 1, Suppl. 198.1, May 1, 2017 (May 1, 2017).

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg Sa, Dudley Me. "Adoptive cell therapy for the treatment of patients with metastatic melanoma", Curr Opin Immunol. Apr. 2009;21(2):233-40.

Rosenberg, "IL-2: The First Effective Immunotherapy for Human Cancer," The Journal of Immunology, col. 192, No. 12, Jun. 6, 2014.

Sadeghi, et al., "Rapid expansion of T cells: Effects of culture and cryopreservation and improtance of short-term cell recovery", Acta Oncologica 2013, 52, 978-986.

Somerville RP, et al., "Clinical scale rapid expansion of lymphocytes for adoptive cell transfer therapy in the WAVE® bioreactor", J Transl Med. Apr. 4, 2012;10:69.

Tran et al., "Minimally Cultured tumor-infiltrating lymphocytes display optimal characteristics for adoptive cell therapy", J. Immunother., Oct. 2008; 31(8), 742-751.

Written Opinion dated Mar. 27, 2018 for International Patent Application No. PCT/US2018/012610, 8 pages.

English translation of Office Action dated Dec. 22, 2021 for Japanese Patent Application No. 2019-536179, 8 pages.

Ikarashi et al.: Solid-phase Anti-CD3 Antibody Activation and Cryopreservation of Human Tumor-infiltrating Lymphocytes Derived from Epithelial Ovarian Cancer, Jpn. J. Cancer Res. 83, 1359-1365, Dec. 1992.

Wilson Wolf—Superior Cell Culture Devices, G-Rex, Oct. 31, 2016.

Bajgain et al.: Optimizing the production of suspension cells using the D6 G-Rex "M" series, Molecular Therapy—Methods & Clinical D6 Development (2014) 1, 14015.

Itzhaki et al.: Establishment and Large-scale Expansion of Minimally D7 cultured "Young" Tumor Infiltrating Lymphocytes for Adoptive Transfer D7 Therapy, J Immunother, vol. 34, No. 2, Feb.-Mar. 2011.

Dudley et al.: CDS+ Enriched "Young" Tumor infiltrating Lymphocytes D9 Can Mediate Regression of Metastatic Melanoma, Clin Cancer Res; D9 16(24), Dec. 15, 2010.

Besser et al.: Clinical Responses in a Phase II Study Using Adoptive D10 Transfer of Short-term Cultured Tumor infiltration Lymphocytes in D10 Metastatic Melanoma Patients; Ciin Cancer Res; 16(9), May 1, 201 O.

Lee et al.: Tumor-infiltrating lymphocytes in melanoma, Curr Oneel D11 Rep. Oct. 2012; 14(5), 468-474.

(56) References Cited

OTHER PUBLICATIONS

Rosenberg et al.: A New Approach to the Adoptive Immunotherapy of D15 Cancer with Tumor-Infiltrating Lymphocytes, Science 19(233): 1318-D1521 (1986).

Rosenberg et al.: Use of Tumor-infiltrating Lymphocytes and Interleukin-2 in the Immunotherapy of Patients with Metastatic Melanoma, N Engl J Med. 319:1676-80 (1988).

Rosenberg et al.: Treatment of Patients with Metastatic Melanoma With Autologous Tumor-Infiltrating Lymphocytes and Interleukin 2; J. Natl. Cancer Inst. 86(15):1159-66 (1994).

Forget et al., The beneficial effects of a gas-permeable flask for expansion of Tumor-Infiltrating lymphocytes as reflected in their mitochondrial function and respiration capacity, OncoImmunology 5(2), Feb. 2016.

* cited by examiner

EXPANSION OF TUMOR INFILTRATING LYMPHOCYTES WITH POTASSIUM CHANNEL AGONISTS AND THERAPEUTIC USES THEREOF

CROSS-REFERENCE TO RELATED APPLICATIONS

This application is a U.S. National Stage application of International Application No. PCT/US2018/012610, filed Jan. 5, 2018, which claims the benefit of priority to U.S. Provisional Patent Application No. 62/504,385, filed May 10, 2017, U.S. Provisional Application No. 62/466,921, filed Mar. 3, 2017, and U.S. Provisional Application No. 62/443,519, filed Jan. 6, 2017, the entireties of which are incorporated herein by reference.

FIELD OF THE INVENTION

Methods of expanding tumor infiltrating lymphocytes (TILs) using potassium channel agonists, including $K_{Ca}3.1$, and compositions of populations of TILs obtained therefrom are disclosed herein. In addition, therapeutic uses of TILs expanded using potassium channel agonists, including in the treatment of diseases such as cancer, are disclosed herein.

BACKGROUND OF THE INVENTION

Treatment of bulky, refractory cancers using adoptive autologous transfer of tumor infiltrating lymphocytes (TILs) represents a powerful approach to therapy for patients with poor prognoses. Gattinoni, et al., *Nat. Rev. Immunol.* 2006, 6, 383-393. TILs are dominated by T cells, and IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. A number of approaches to improve responses to TIL therapy in melanoma and to expand TIL therapy to other tumor types have been explored with limited success, and the field remains challenging. Goff, et al., *J. Clin. Oncol.* 2016, 34, 2389-97; Dudley, et al., *J. Clin. Oncol.* 2008, 26, 5233-39; Rosenberg, et al., *Clin. Cancer Res.* 2011, 17, 4550-57.

Potassium channels ($K^+$ channels) are a class of membrane-spanning ion conductance channels commonly found in cells. $K^+$ channels fall into four major classes: (1) voltage-gated potassium channels ($K_v$), which open or in response to variations in transmembrane voltage; (2) calcium-activated potassium channels ($K_{Ca}$), which open in response to the presence of calcium ions or other signaling molecules; (3) inwardly-rectifying potassium channels ($K_{IR}$), which allow positive charge to pass more readily into the cell; and (4) tandem pore domain potassium channels ($K_{2P}$), which are constitutively open or possess a high basal activation. Within these four classes, a very large number of $K^+$ channel subtypes have been recognized. However, only two $K^+$ channel subtypes are known to be expressed by T cells. Activated effector T cells express high levels of $K_v1.3$ (voltage-gated potassium channel, shaker-related subfamily member 3, encoded by KCNA3), while activated naïve and central memory T cell subsets express high levels of $K_{Ca}3.1$ (intermediate conductance $Ca^{2+}$-activated $K^+$ channel, also known as the IK channel or the SK4 channel, encoded by KCNN4). Feske, et al., *Annu. Rev. Immunol.* 2015, 33, 291-353; Di, et al., *Proc. Nat'l Acad. Sci. USA* 2010, 107, 1541-46. Inhibition of $K_{Ca}3.1$ suppresses murine T cell proliferation and cytokine production. Di, et al., *Proc. Nat'l Acad. Sci. USA* 2010, 107, 1541-46. Necrotic tissues release high intracellular stores of $K^+$ into the extracellular space, high intracellular $K^+$ concentrations suppress interferon-γ (IFN-γ) production in T-cells, and overexpression of $K_v1.3$ in murine T cells improves anti-tumor immunity and host survival. Eil, et al., *Nature* 2016, 537, 539-543. However, the influence of $K^+$ channel manipulation on the expansion and performance of TILs as a therapy for diseases such as cancer has not been explored.

The present invention provides the surprising finding that $K^+$ channel agonists, openers, or activators, including $K_{Ca}3.1$ channel agonists, openers, or activators, when employed in a TIL expansion process, results in improved TIL phenotypic characteristics and less TIL differentiation.

SUMMARY OF THE INVENTION

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
  wherein either the first cell culture medium or the second cell culture medium or both the first cell culture medium and the second cell culture medium further comprise a potassium channel agonist.

In an embodiment, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor into tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist; and wherein the potassium channel agonist is a $K_{Ca}3.1$ (IK channel) agonist.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the second population of TILs comprises an increased population of T cells with a phenotype selected from the group consisting CD8$^+$CD28$^+$, CD8$^+$CD27$^+$, CD8$^+$CD27$^+$CD28$^+$, CCR7$^+$, and combinations thereof, relative to a reference population of TILs obtained without the potassium channel agonist, wherein the phenotype in the second population of TILs is increased by at least 5% relative to the reference population of TILs. In some instances, the increase is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000%.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the third population of TILs comprises an increased population of T cells with a phenotype selected from the group consisting CD8$^+$CD28$^+$, CD8$^+$CD27$^+$, CD8$^+$CD27$^+$CD28$^+$, CCR7$^+$, and combinations thereof, relative to a reference population of TILs obtained without the potassium channel agonist, wherein the phenotype in the third population of TILs is increased by at least 5% relative to the reference population of TILs. In some instances, the increase is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000%.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer; wherein the potassium channel agonist is a $K_{Ca}3.1$ (IK channel) agonist, and wherein both the first cell culture medium further comprises the $K_{Ca}3.1$ agonist and the second cell culture medium further comprises the $K_{Ca}3.1$ agonist.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer; wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the first cell culture medium is between 1 and 1000 nM.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer; wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the first cell culture medium is about 100 nM.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer; wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the second cell culture medium is between 0.1 and 100 mM.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the second cell culture medium is about 50 mM.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the initial expansion is performed over a period of 21 days or less.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the initial expansion is performed over a period of 11 days or less.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the rapid expansion is performed over a period of 7 days or less.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is a compound according to Formula (1):

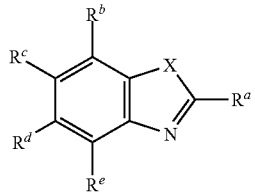

Formula (1)

or a pharmaceutically-acceptable salt, cocrystal, solvate, or prodrug thereof, wherein $R^a$ is selected from halo, cyano, hydroxy, thiol, $(C_{1-6})$ alkyl, —$NH_2$, and —$NR^1R^2$;

$R^1$ and $R^2$ are independently H or $(C_{1-6})$alkyl;

X is selected from the group consisting of S, O, and NH;

$R^b$ and $R^c$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^b$ and $R^c$ together with the carbon atoms to which they are attached form a ring selected from the group consisting of an aryl, naphthyl, anthryl, heteroaryl, cycloalkyl, and heterocycloalkyl ring; and $R^d$ and $R^e$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^d$ and $R^e$ together with the carbon atoms to which they are attached form a ring selected from the group consisting of an aryl, naphthyl, anthryl, heteroaryl, cycloalkyl, and heterocycloalkyl ring;

with the proviso that if $R^b$ and $R^c$ form a ring, then $R^d$ and $R^e$ do not form a ring, and if $R^d$ and $R^e$ form a ring, then $R^b$ and $R^c$ do not form a ring.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer, wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is naphtho[1,2-d]thiazol-2-ylamine (SKA-31):

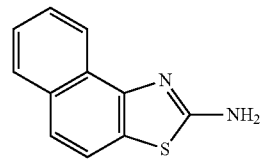 [SMILES: Nc1nc2c(ccc3ccccc32)s1]

or a pharmaceutically-acceptable salt, cocrystal, solvate, or prodrug thereof.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is anthra[2,1-d]thiazol-2-ylamine (SKA-20):

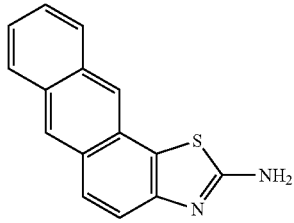 [SMILES: Nc1nc2ccc3cc4ccccc4cc3c2s1]

or a pharmaceutically-acceptable salt, cocrystal, solvate, or prodrug thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is 6,7-dichloro-1H-indole-2,3-dione 3-oxime (NS309):

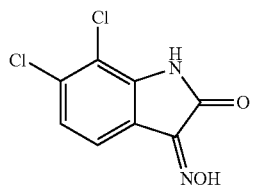

or a pharmaceutically-acceptable salt, cocrystal, solvate, or prodrug thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is riluzole:

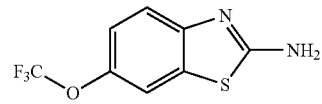

or a pharmaceutically-acceptable salt, cocrystal, solvate, or prodrug thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (1K channel) agonist, and wherein the $K_{Ca}3.1$ agonist is selected from the group consisting of:

5-methylnaphtho[1,2-d]oxazol-2-amine;
5-ethylnaphtho[1,2-d]oxazol-2-amine;
5-propylnaphtho[1,2-d]oxazol-2-amine;
5-cyclopropylnaphtho[1,2-d]oxazol-2-amine;
5-(tert-butyl)naphtho[1,2-d]oxazol-2-amine;
5-fluoronaphtho[1,2-d]oxazol-2-amine;
5-chloronaphtho[1,2-d]oxazol-2-amine;
5-bromonaphtho[1,2-d]oxazol-2-amine;
5-iodonaphtho[1,2-d]oxazol-2-amine;
2-aminonaphtho[1,2-d]oxazole-5-carbonitrile;
naphtho[1,2-d]oxazol-2,5-diamine;
$N^5$-methylnaphtho[1,2-d]oxazole-2,5-diamine;
$N^5,N^5$-dimethylnaphtho[1,2-d]oxazole-2,5-diamine;
$N^5$-ethylnaphtho[1,2-d]oxazole-2,5-diamine;
5-(pyrrolidine-1-yl)naphtho[1,2-d]oxazol-2-amine;
5-methoxynaphtho[1,2-d]oxazol-2-amine;
5-trifluoromethylnaphtho[1,2-d]oxazol-2-amine;
5-methylnaphtho[2,1-d]oxazol-2-amine;
5-ethylnaphtho[2,1-d]oxazol-2-amine;
5-propylnaphtho[2,1-d]oxazol-2-amine;
5-cyclopropylnaphtho[2,1-d]oxazol-2-amine;
5-(tert-butyl)naphtho[2,1-d]oxazol-2-amine;
5-fluoronaphtho[2,1-d]oxazol-2-amine;
5-chloronaphtho[2,1-d]oxazol-2-amine;
5-bromonaphtho[2,1-d]oxazol-2-amine;
5-iodonaphtho[2,1-d]oxazol-2-amine;
2-aminonaphtho[2,1-d]oxazole-5-carbonitrile;
naphtho[2,1-d]oxazol-2,5-diamine;
N5-methylnaphtho[2,1-d]oxazole-2,5-diamine;
N5,N5-dimethylnaphtho[2,1-d]oxazole-2,5-diamine;
N5-ethylnaphtho[2,1-d]oxazole-2,5-diamine;
5-(pyrrolidine-1-yl)naphtho[2,1-d]oxazol-2-amine;
5-methoxynaphtho[2,1-d]oxazol-2-amine;
5-trifluoromethylnaphtho[2,1-d]oxazol-2-amine;

and pharmaceutically-acceptable salts, cocrystals, solvates, or prodrugs thereof.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, and wherein the IL-2 is present at an initial concentration of between 1000 IU/mL and 6000 IU/mL in the first cell culture medium.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, wherein the IL-2 is present at an initial concentration of between 1000 IU/mL and 6000 IU/mL and the OKT-3 antibody is present at an initial concentration of about 30 ng/mL in the second cell culture medium.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the initial expansion is performed using a gas permeable container.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, and wherein the rapid expansion is performed using a gas permeable container.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, and wherein the first cell culture medium further comprises a cytokine selected from the group consisting of IL-4, IL-7, IL-15, IL-21, and combinations thereof.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, and wherein the second cell culture medium further comprises a cytokine selected from the group consisting of IL-4, IL-7, IL-15, IL-21, and combinations thereof.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, further comprising the step of treating the patient with the potassium channel agonist starting on the day after administration of the third population of TILs to the patient.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, further comprising the step of treating the patient with the potassium channel agonist prior to the step of resecting of a tumor from the patient.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, further comprising the step of treating the patient with a non-myeloablative lymphodepletion regimen prior to administering the third population of TILs to the patient.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
(f) harvesting the third population of TILs; and
(g) administering a therapeutically effective portion of the third population of TILs to a patient with the cancer;
wherein either the first cell culture medium or the second cell culture medium or both the first cell culture medium and the second cell culture medium further comprise a potassium channel agonist, further comprising the step of treating the patient with a non-myeloablative lymphodepletion regimen prior to administering the third population of TILs to the patient, wherein the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In an embodiment, the invention provides a method of treating a cancer with a population of tumor infiltrating lymphocytes (TILs) comprising the steps of:
(a) resecting a tumor from a patient, the tumor comprising a first population of TILs;
(b) fragmenting the tumor into tumor fragments;
(c) contacting the tumor fragments with a first cell culture medium;
(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, further comprising the step of treating the patient with a high-dose IL-2 regimen starting on the day after administration of the third population of TILs to the patient.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, further comprising the step of treating the patient with a high-dose IL-2 regimen starting on the day after administration of the third population of TILs to the patient, wherein the high-dose IL-2 regimen comprises 600,000 or 720,000 IU/kg of aldesleukin, or a biosimilar or variant thereof, administered as a 15-minute bolus intravenous infusion every eight hours until tolerance.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the cancer is selected from the group consisting of melanoma, ovarian cancer, cervical cancer, lung cancer, bladder cancer, breast cancer, head and neck cancer, renal cell carcinoma, acute myeloid leukemia, colorectal cancer, and sarcoma.

In an embodiment, the invention provides a method of treating a cancer with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer;

wherein either the first cell culture medium or the second cell culture medium or both the first cell culture medium and the second cell culture medium further comprise a potassium channel agonist, and wherein the cancer is selected from the group consisting of non-small cell lung cancer (NSCLC), estrogen receptor positive (ER$^+$) breast cancer, progesterone receptor positive (PR$^+$) breast cancer, human epidermal growth factor receptor 2 (HER2$^+$) breast cancer, triple positive breast cancer (ER+/PR+/HER2+), triple negative breast cancer (ER−/PR−/HER2−), double-refractory melanoma, and uveal (ocular) melanoma.

In an embodiment, the invention provides a process for the preparation of a population of tumor infiltrating lymphocytes (TILs) from a tumor, the process comprising the steps of:
- (a) fragmenting the tumor;
- (b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
- (b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
- (c) harvesting the third population of TILs; and
- wherein either the first cell culture medium or the second cell culture medium or both the first cell culture medium and the second cell culture medium further comprise a potassium channel agonist.

In an embodiment, the invention provides a process for the preparation of a population of tumor infiltrating lymphocytes (TILs) from a tumor, the process comprising the steps of:
- (a) fragmenting the tumor;
- (b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
- (b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
- (c) harvesting the third population of TILs; and
- wherein either the first cell culture medium or the second cell culture medium or both the first cell culture medium and the second cell culture medium further comprise a potassium channel agonist, and wherein the first population of TILs is obtained from a tumor or a portion thereof.

In an embodiment, the invention provides a process for the preparation of a population of tumor infiltrating lymphocytes (TILs) from a tumor, the process comprising the steps of:
- (a) fragmenting the tumor;
- (b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
- (b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
- (c) harvesting the third population of TILs; and
- wherein either the first cell culture medium or the second cell culture medium or both the first cell culture medium and the second cell culture medium further comprise a potassium channel agonist, and wherein the tumor or portion thereof has been resected from a patient.

In an embodiment, the invention provides a process for the preparation of a population of tumor infiltrating lymphocytes (TILs) from a tumor, the process comprising the steps of:
- (a) fragmenting the tumor;
- (b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
- (b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
- (c) harvesting the third population of TILs; and
- wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist.

In an embodiment, the invention provides a process for the preparation of a population of tumor infiltrating lymphocytes (TILs) from a tumor, the process comprising the steps of:
- (a) fragmenting the tumor;
- (b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
- (b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, and wherein the second population of TILs comprises an increased population of T cells with a phenotype selected from the group consisting CD8$^+$CD28$^+$, CD8$^+$CD27$^+$, CD8$^+$CD27$^+$CD28$^+$, CCR7$^+$, and combinations thereof, relative to a reference population of TILs obtained without the potassium channel agonist, wherein the phenotype in the second population of TILs is increased by at least 5% relative to the reference population of TILs. In some instances, the increase is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000%.

In an embodiment, the invention provides a process for the preparation of a population of tumor infiltrating lymphocytes (TILs) from a tumor, the process comprising the steps of:

(a) fragmenting the tumor;

(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;

(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, and wherein the third population of TILs comprises an increased population of T cells with a phenotype selected from the group consisting CD8$^+$CD28$^+$, CD8$^+$CD27$^+$, CD8$^+$CD27$^+$CD28$^+$, CCR7$^+$, and combinations thereof, relative to a reference population of TILs obtained without the potassium channel agonist, wherein the phenotype in the third population of TILs is increased by at least 5% relative to the reference population of TILs. In some instances, the increase is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, about 600%, about 700%, about 800%, about 900%, or about 1000%.

In an embodiment, the invention provides a process for the preparation of a population of tumor infiltrating lymphocytes (TILs) from a tumor, the process comprising the steps of:

(a) fragmenting the tumor;

(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;

(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein both the first cell culture medium further comprises the $K_{Ca}3.1$ agonist and the second cell culture medium further comprises the $K_{Ca}3.1$ agonist.

In an embodiment, the invention provides a process for the preparation of a population of tumor infiltrating lymphocytes (TILs) from a tumor, the process comprising the steps of:

(a) fragmenting the tumor;

(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;

(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the first cell culture medium is between 1 and 1000 nM.

In an embodiment, the invention provides a process for the preparation of a population of tumor infiltrating lymphocytes (TILs) from a tumor, the process comprising the steps of:

(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the first cell culture medium is about 100 nM.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the second cell culture medium is between 0.1 and 100 mM.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the concentration of the $K_{Ca}3.1$ agonist in the first cell culture medium is about 50 mM.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, and wherein the initial expansion is performed over a period of 21 days or less.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, and wherein the initial expansion is performed over a period of 11 days or less.

In an embodiment, the invention provides a process for the preparation of a population of tumor infiltrating lymphocytes (TILs) from a tumor, the process comprising the steps of:

(a) fragmenting the tumor;

(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;

(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, and wherein the rapid expansion is performed over a period of 7 days or less.

In an embodiment, the invention provides a process for the preparation of a population of tumor infiltrating lymphocytes (TILs) from a tumor, the process comprising the steps of:

(a) fragmenting the tumor;

(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;

(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is a compound according to Formula (1):

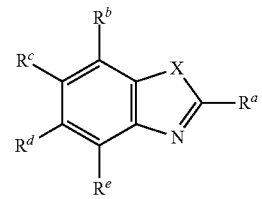

Formula (1)

or a pharmaceutically-acceptable salt, cocrystal, solvate, or prodrug thereof, wherein $R^a$ is selected from halo, cyano, hydroxy, thiol, $(C_{1-6})$ alkyl, —$NH_2$, and —$NR^1R^2$;

$R^1$ and $R^2$ are independently H or $(C_{1-6})$alkyl;

X is selected from the group consisting of S, O, and NH;

$R^b$ and $R^c$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^b$ and $R^c$ together with the carbon atoms to which they are attached form a ring selected from the group consisting of an aryl, naphthyl, anthryl, heteroaryl, cycloalkyl, and heterocycloalkyl ring; and $R^d$ and $R^e$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^d$ and $R^e$ together with the carbon atoms to which they are attached form a ring selected from the group consisting of an aryl, naphthyl, anthryl, heteroaryl, cycloalkyl, and heterocycloalkyl ring;

with the proviso that if $R^b$ and $R^c$ form a ring, then $R^d$ and $R^e$ do not form a ring, and if $R^d$ and $R^e$ form a ring, then $R^b$ and $R^c$ do not form a ring.

In an embodiment, the invention provides a process for the preparation of a population of tumor infiltrating lymphocytes (TILs) from a tumor, the process comprising the steps of:

(a) fragmenting the tumor;

(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;

(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;

(c) harvesting the third population of TILs; and wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is naphtho[1,2-d]thiazol-2-ylamine (SKA-31):

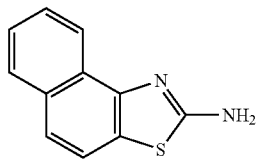 [SMILES: Nc1nc2c(ccc3ccccc32)s1]

or a pharmaceutically-acceptable salt, cocrystal, solvate, or prodrug thereof.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is anthra[2,1-d]thiazol-2-ylamine (SKA-20):

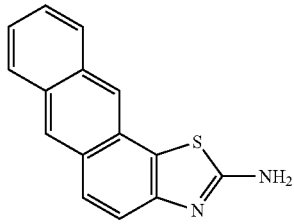

or a pharmaceutically-acceptable salt, cocrystal, solvate, or prodrug thereof.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is 6,7-dichloro-1H-indole-2,3-dione 3-oxime (NS309):

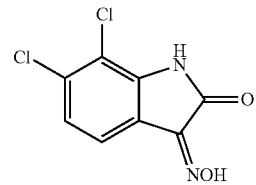

or a pharmaceutically-acceptable salt, cocrystal, solvate, or prodrug thereof.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is riluzole:

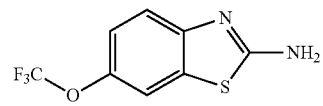

or a pharmaceutically-acceptable salt, cocrystal, solvate, or prodrug thereof.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the $K_{Ca}3.1$ agonist is selected from the group consisting of:
5-methylnaphtho[1,2-d]oxazol-2-amine;
5-ethylnaphtho[1,2-d]oxazol-2-amine;
5-propylnaphtho[1,2-d]oxazol-2-amine;
5-cyclopropylnaphtho[1,2-d]oxazol-2-amine;
5-(tert-butyl)naphtho[1,2-d]oxazol-2-amine;
5-fluoronaphtho[1,2-d]oxazol-2-amine;
5-chloronaphtho[1,2-d]oxazol-2-amine;
5-bromonaphtho[1,2-d]oxazol-2-amine;
5-iodonaphtho[1,2-d]oxazol-2-amine;
2-aminonaphtho[1,2-d]oxazole-5-carbonitrile;
naphtho[1,2-d]oxazol-2,5-diamine;
$N^5$-methylnaphtho[1,2-d]oxazole-2,5-diamine;
$N^5,N^5$-dimethylnaphtho[1,2-d]oxazole-2,5-diamine;
$N^5$-ethylnaphtho[1,2-d]oxazole-2,5-diamine;
5-(pyrrolidine-1-yl)naphtho[1,2-d]oxazol-2-amine;
5-methoxynaphtho[1,2-d]oxazol-2-amine;
5-trifluoromethylnaphtho[1,2-d]oxazol-2-amine;
5-methylnaphtho[2,1-d]oxazol-2-amine;
5-ethylnaphtho[2,1-d]oxazol-2-amine;
5-propylnaphtho[2,1-d]oxazol-2-amine;
5-cyclopropylnaphtho[2,1-d]oxazol-2-amine;
5-(tert-butyl)naphtho[2,1-d]oxazol-2-amine;
5-fluoronaphtho[2,1-d]oxazol-2-amine;
5-chloronaphtho[2,1-d]oxazol-2-amine;
5-bromonaphtho[2,1-d]oxazol-2-amine;
5-iodonaphtho[2,1-d]oxazol-2-amine;
2-aminonaphtho[2,1-d]oxazole-5-carbonitrile;
naphtho[2,1-d]oxazol-2,5-diamine;
N5-methylnaphtho[2,1-d]oxazole-2,5-diamine;
N5,N5-dimethylnaphtho[2,1-d]oxazole-2,5-diamine;
N5-ethylnaphtho[2,1-d]oxazole-2,5-diamine;
5-(pyrrolidine-1-yl)naphtho[2,1-d]oxazol-2-amine;
5-methoxynaphtho[2,1-d]oxazol-2-amine;
5-trifluoromethylnaphtho[2,1-d]oxazol-2-amine;
and pharmaceutically-acceptable salts, cocrystals, solvates, or prodrugs thereof.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, and wherein the IL-2 is present at an initial concentration of between 1000 IU/mL and 6000 IU/mL in the first cell culture medium.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, and wherein the IL-2 is present at an initial concentration of between 1000 IU/mL and 6000 IU/mL and the OKT-3 antibody is present at an initial concentration of about 30 ng/mL in the second cell culture medium.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the initial expansion is performed using a gas permeable container.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the rapid expansion is performed using a gas permeable container.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, and wherein the first cell culture medium further comprises a cytokine selected from the group consisting of IL-4, IL-7, IL-15, IL-21, and combinations thereof.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, and wherein the second cell culture medium further comprises a cytokine selected from the group consisting of IL-4, IL-7, IL-15, IL-21, and combinations thereof.

In an embodiment, the invention provides a process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(b) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(c) harvesting the third population of TILs; and
wherein either the first cell culture medium or the second cell culture medium or both the first cell culture medium and the second cell culture medium further comprise a potassium channel agonist, wherein the potassium channel agonist is a $K_{Ca}3.1$ (IK channel) agonist, and wherein the process is an ex vivo method.

In an embodiment, the invention provides a population of TILs for the treatment of cancer in a patient, the population of TILs obtainable by a process according to any one of the foregoing processes. In an embodiment, the invention provides a population of TILs for the treatment of cancer in a patient, the population of TILs obtainable by a process according to any one of the foregoing processes, wherein the cancer is selected from melanoma, ovarian cancer, cervical cancer, lung cancer, bladder cancer, breast cancer, head and neck cancer, renal cell carcinoma, acute myeloid leukemia, colorectal cancer, sarcoma, non-small cell lung cancer (NSCLC) or triple negative breast cancer, double-refractory melanoma, and uveal (ocular) melanoma. In an embodiment, the invention provides a population of TILs for the treatment of cancer in a patient by intratumoral injection or intravenous infusion, the population of TILs obtainable by a process according to any one of the foregoing processes, wherein the cancer is selected from melanoma, ovarian cancer, cervical cancer, lung cancer, bladder cancer, breast cancer, head and neck cancer, renal cell carcinoma, acute myeloid leukemia, colorectal cancer, sarcoma, non-small cell lung cancer (NSCLC) or triple negative breast cancer, double-refractory melanoma, and uveal (ocular) melanoma. In any of the foregoing embodiments, the population of TILs may be administered in combination with a chemotherapeutic agent.

In an embodiment, the invention provides a cell culture medium comprising IL-2 and a potassium channel agonist.

In an embodiment, the invention provides a cell culture medium comprising IL-2, an anti-CD3 antibody or a fragment, variant, or biosimilar thereof, peripheral blood mononuclear cells (PBMCs), and a potassium channel agonist.

In an embodiment, the invention provides a cell culture medium comprising IL-2 and a potassium channel agonist, wherein the potassium channel agonist is a $K_{Ca}3.1$ agonist.

In an embodiment, the invention provides a cell culture medium comprising IL-2, an anti-CD3 antibody or a fragment, variant, or biosimilar thereof, peripheral blood mononuclear cells (PBMCs), and a potassium channel agonist, wherein the potassium channel agonist is a $K_{Ca}3.1$ agonist.

In an embodiment, the invention provides a cell culture medium comprising IL-2 and a potassium channel agonist, wherein the potassium channel agonist is a $K_{Ca}3.1$ agonist, wherein the $K_{Ca}3.1$ agonist is a compound according to Formula (1):

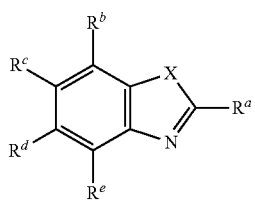

Formula (1)

or a pharmaceutically-acceptable salt, cocrystal, solvate, or prodrug thereof, wherein $R^a$ is selected from halo, cyano, hydroxy, thiol, (C$_{1-6}$) alkyl, —NH$_2$, and —NR$^1$R$^2$;

$R^1$ and $R^2$ are independently H or (C$_{1-6}$)alkyl;

X is selected from the group consisting of S, O, and NH;

$R^b$ and $R^c$ are independently selected from the group consisting of hydrogen, (C$_{1-6}$)alkyl, (C$_{1-6}$)alkoxyl, halo, nitro, aryl, heteroaryl, (C$_{1-6}$)alkyl and (C$_{3-7}$)cycloalkyl or $R^b$ and $R^c$ together with the carbon atoms to which they are attached form a ring selected from the group consisting of an aryl, naphthyl, anthryl, heteroaryl, cycloalkyl, and heterocycloalkyl ring; and $R^d$ and $R^e$ are independently selected from the group consisting of hydrogen, (C$_{1-6}$)alkyl, (C$_{1-6}$)alkoxyl, halo, nitro, aryl, heteroaryl, (C$_{1-6}$)alkyl and (C$_{3-7}$)cycloalkyl or $R^d$ and $R^e$ together with the carbon atoms to which they are attached form a ring selected from the group consisting of an aryl, naphthyl, anthryl, heteroaryl, cycloalkyl, and heterocycloalkyl ring;

with the proviso that if $R^b$ and $R^c$ form a ring, then $R^d$ and $R^e$ do not form a ring, and if $R^d$ and $R^e$ form a ring, then $R^b$ and $R^c$ do not form a ring.

In an embodiment, the invention provides a cell culture medium comprising IL-2 and a potassium channel agonist, wherein the potassium channel agonist is a $K_{Ca}3.1$ agonist, wherein the $K_{Ca}3.1$ agonist is naphtho[1,2-d]thiazol-2-ylamine (SKA-31):

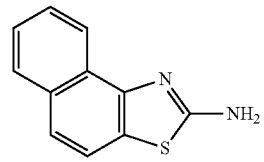

or a pharmaceutically-acceptable salt, cocrystal, solvate, or prodrug thereof.

In an embodiment, the invention provides a cell culture medium comprising IL-2 and a potassium channel agonist, wherein the potassium channel agonist is a $K_{Ca}3.1$ agonist, wherein the $K_{Ca}3.1$ agonist is anthra[2,1-d]thiazol-2-ylamine (SKA-20):

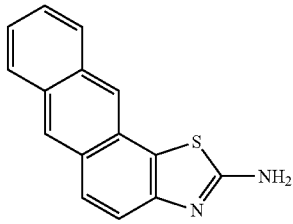 [SMILES: Nc1nc2ccc3cc4ccccc4cc3c2s1]

or a pharmaceutically-acceptable salt, cocrystal, solvate, or prodrug thereof.

In an embodiment, the invention provides a cell culture medium comprising IL-2 and a potassium channel agonist, wherein the potassium channel agonist is a $K_{Ca}3.1$ agonist, wherein the $K_{Ca}3.1$ agonist is 6,7-dichloro-1H-indole-2,3-dione 3-oxime (NS309):

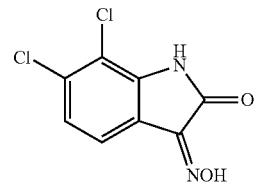

or a pharmaceutically-acceptable salt, cocrystal, solvate, or prodrug thereof.

In an embodiment, the invention provides a cell culture medium comprising IL-2 and a potassium channel agonist, wherein the potassium channel agonist is a $K_{Ca}3.1$ agonist, wherein the $K_{Ca}3.1$ agonist is riluzole:

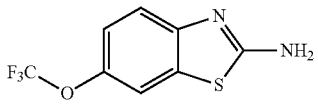 [SMILES: Nc1nc2ccc(OC(F)(F)F)cc2s1]

or a pharmaceutically-acceptable salt, cocrystal, solvate, or prodrug thereof.

In an embodiment, the invention provides a cell culture medium comprising IL-2 and a potassium channel agonist, wherein the potassium channel agonist is a $K_{Ca}3.1$ agonist, wherein the $K_{Ca}3.1$ agonist is selected from the group consisting of:
5-methylnaphtho[1,2-d]oxazol-2-amine;
5-ethylnaphtho[1,2-d]oxazol-2-amine;
5-propylnaphtho[1,2-d]oxazol-2-amine;
5-cyclopropylnaphtho[1,2-d]oxazol-2-amine;
5-(tert-butyl)naphtho[1,2-d]oxazol-2-amine;
5-fluoronaphtho[1,2-d]oxazol-2-amine;
5-chloronaphtho[1,2-d]oxazol-2-amine;
5-bromonaphtho[1,2-d]oxazol-2-amine;
5-iodonaphtho[1,2-d]oxazol-2-amine;
2-aminonaphtho[1,2-d]oxazole-5-carbonitrile;
naphtho[1,2-d]oxazol-2,5-diamine;
$N^5$-methylnaphtho[1,2-d]oxazole-2,5-diamine;
$N^5,N^5$-dimethylnaphtho[1,2-d]oxazole-2,5-diamine;
$N^5$-ethylnaphtho[1,2-d]oxazole-2,5-diamine;
5-(pyrrolidine-1-yl)naphtho[1,2-d]oxazol-2-amine;
5-methoxynaphtho[1,2-d]oxazol-2-amine;
5-trifluoromethylnaphtho[1,2-d]oxazol-2-amine;
5-methylnaphtho[2,1-d]oxazol-2-amine;
5-ethylnaphtho[2,1-d]oxazol-2-amine;
5-propylnaphtho[2,1-d]oxazol-2-amine;
5-cyclopropylnaphtho[2,1-d]oxazol-2-amine;
5-(tert-butyl)naphtho[2,1-d]oxazol-2-amine;
5-fluoronaphtho[2,1-d]oxazol-2-amine;
5-chloronaphtho[2,1-d]oxazol-2-amine;
5-bromonaphtho[2,1-d]oxazol-2-amine;
5-iodonaphtho[2,1-d]oxazol-2-amine;
2-aminonaphtho[2,1-d]oxazole-5-carbonitrile;
naphtho[2,1-d]oxazol-2,5-diamine;
N5-methylnaphtho[2,1-d]oxazole-2,5-diamine;
N5,N5-dimethylnaphtho[2,1-d]oxazole-2,5-diamine;
N5-ethylnaphtho[2,1-d]oxazole-2,5-diamine;
5-(pyrrolidine-1-yl)naphtho[2,1-d]oxazol-2-amine;
5-methoxynaphtho[2,1-d]oxazol-2-amine;
5-trifluoromethylnaphtho[2,1-d]oxazol-2-amine;
and pharmaceutically-acceptable salts, cocrystals, solvates, or prodrugs thereof.

In an embodiment, the invention provides a cell culture medium comprising IL-2 and a potassium channel agonist, wherein the potassium channel agonist is a $K_{Ca}3.1$ agonist.

In an embodiment, the invention provides a kit comprising a cell culture medium comprising IL-2 and a potassium channel agonist, wherein the potassium channel agonist is a $K_{Ca}3.1$ agonist.

In an embodiment, the invention provides a kit comprising a cell culture medium comprising IL-2, a potassium channel agonist, and a tumor, wherein the potassium channel agonist is a $K_{Ca}3.1$ agonist.

In an embodiment, the invention provides the use of a potassium channel agonist in the manufacture of a population of TILs for the treatment of cancer. Aptly, the potassium channel agonist is a $K_{Ca}3.1$ (IK channel) agonist.

In an embodiment, the invention provides the use of a potassium channel agonist in the manufacture of a population of TILs for the treatment of cancer, wherein the potassium channel agonist is a $K_{Ca}3.1$ agonist. In an embodiment, the invention provides the use of a potassium channel agonist in the manufacture of a population of TILs for the treatment of cancer, wherein the potassium channel agonist is a $K_{Ca}3.1$ agonist disclosed herein. Aptly, the potassium channel agonist is SKA-31, SKA-20, NS309, riluzole, or a pharmaceutically-acceptable salt, cocrystal, solvate, or prodrug thereof.

BRIEF DESCRIPTION OF THE DRAWINGS

The foregoing summary, as well as the following detailed description of the invention, will be better understood when read in conjunction with the appended drawings.

BRIEF DESCRIPTION OF THE SEQUENCE LISTING

Figure 1:
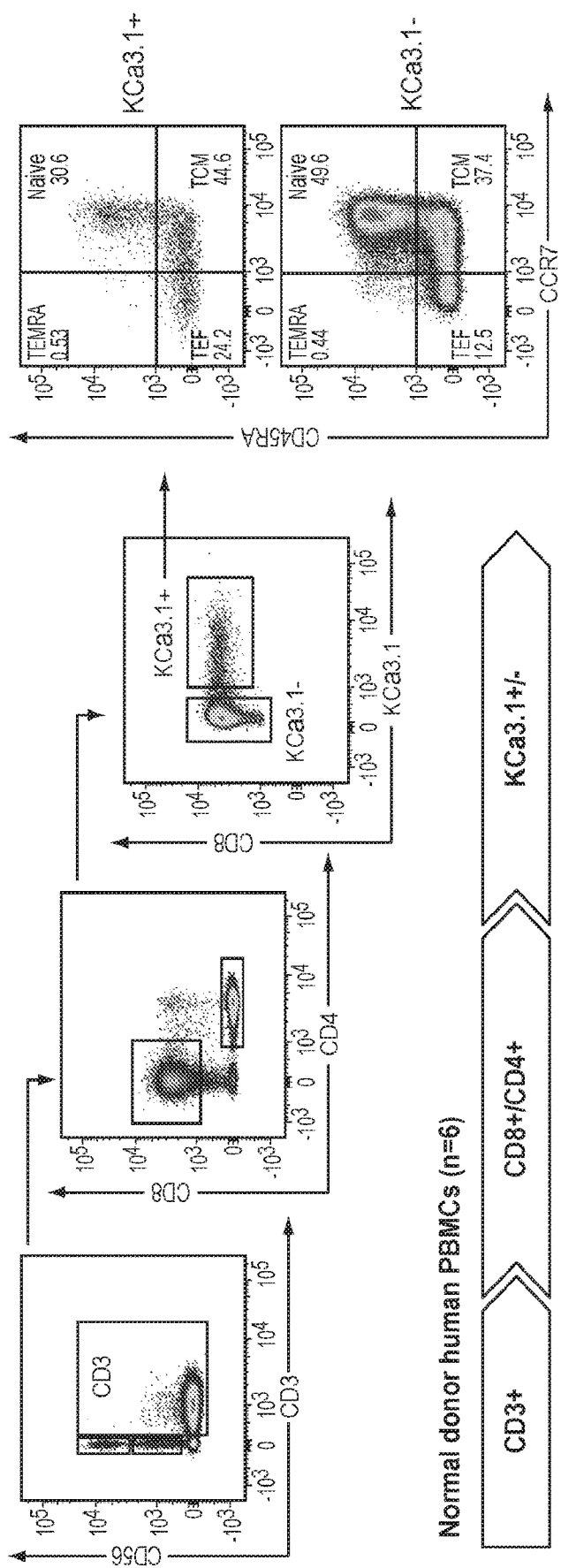
FIG. 1 illustrates the sorting strategy used in flow cytometry experiments for analysis of $K_{Ca}3.1$ expression in T cell subsets.

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is the amino acid sequence of a recombinant human IL-4 protein.

SEQ ID NO:6 is the amino acid sequence of a recombinant human IL-7 protein.

SEQ ID NO:7 is the amino acid sequence of a recombinant human IL-15 protein.

SEQ ID NO:8 is the amino acid sequence of a recombinant human IL-21 protein.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "in vivo" refers to an event that takes place in a mammalian subject's body.

The term "ex vivo" refers to an event that takes place outside of a mammalian subject's body, in an artificial environment.

The term "in vitro" refers to an event that takes places in a test system. In vitro assays encompass cell-based assays in which alive or dead cells may be are employed and may also encompass a cell-free assay in which no intact cells are employed.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are described herein.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "central memory T cell" refers to a subset of T cells that in the human are CD45R0+ and constitutively express CCR7 ($CCR7^{hi}$) and CD62L ($CD62L^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 ($CCR7^{lo}$) and are heterogeneous or low for CD62L expression ($CD62L^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, Calif., USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collodion. of Authenticated Cell Cultures (ECACC) and assigned Catalogue No. 86022706.

TABLE 1

Amino acid sequences of muromonab.

| Identifier | Sequence (One-Letter Amino Acid Symbols) | | | | | |
|---|---|---|---|---|---|---|
| SEQ ID NO: 1 Muromonab heavy chain | QVQLQQSGAE NQKFKDKATL KTTAPSVYPL YTLSSSVTVT PSVFLFPPKP | LARPGASVKM TTDKSSSTAY APVCGGTTGS SSTWPSQSIT KDTLMISRTP | SCKASGYTFT MQLSSLTSED SVTLGCLVKG CNVAHPASST EVTCVVVDVS | RYTMHWVKQR SAVYYCARYY YFPEPVTLTW KVDKKIEPRP HEDPEVKFNW | PGQGLEWIGY DDHYCLDYWG NSGSLSSGVH KSCDKTHTCP YVDGVEVHNA | INPSRGYTNY QGTTLTVSSA TFPAVLQSDL PCPAPELLGG KTKPREEQYN | 60 120 180 240 300 |

TABLE 1-continued

Amino acid sequences of muromonab.

| Identifier | Sequence (One-Letter Amino Acid Symbols) | |
|---|---|---|
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 Muromonab light chain | QIVLTQSPAI MSASPGEKVT MTCSASSSVS YMNWYQQKSG TSPKRWIYDT SKLASGVPAH | 60 |
| | FRGSGSGTSY SLTISGMEAE DAATYYCQQW SSNPFTFGSG TKLEINRADT APTVSIFPPS | 120 |
| | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, Calif., USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL | 60 |
| | EEELKPLEEV LNLAQSKNFH LRPRDLISNI NVIVLELKGS ETTFMCEYAD ETATIVEFLN | 120 |
| | RWITFCQSII STLT | 134 |
| SEQ ID NO: 4 Aldesleukin | PTSSSTKKTQ LQLEHLLLDL QMILNGINNY KNPKLTRMLT FKFYMPKKAT ELKHLQCLEE | 60 |
| | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREKYSKCSS | 130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP TKSLEENKSL | 120 |
| | KEQKKLNDLC FLKRLLQEIK TCWNKILMGT KEH | 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LQSFVHIVQM FINTS | 115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG | 60 |
| | NNERIINVSI KKLKRKPPST NAGRRQKHRL TCPSCDSYEK KPPKEFLERF KSLLQKMIHQ | 120 |
| | HLSSRTHGSE DS | 132 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and $IgG_1$ expression from B cells. Recombinant human IL-4 suitable for use in the invention is commercially available from multiple suppliers, including ProSpec-Tany TechnoGene Ltd., East Brunswick, N.J., USA (Cat. No. CYT-211) and ThermoFisher Scientific, Inc., Waltham, Mass., USA (human IL-4 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, N.J., USA (Cat. No. CYT-254) and ThermoFisher Scientific, Inc., Waltham, Mass., USA (human IL-7 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-15 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and ThermoFisher Scientific, Inc., Waltham, Mass., USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human $CD4^+$ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, N.J., USA (Cat. No. CYT-408-b) and ThermoFisher Scientific, Inc., Waltham, Mass., USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{10}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.,* 2012, 72, 2473. Although tumors express antigens that should be recognized by T cells, tumor clearance by the immune system is rare because of immune suppression by the microenvironment.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The term "solvate" refers to a compound in physical association with one or more molecules of a pharmaceutically acceptable solvent. The term solvate includes hydrates, wherein water is physically associated with a compound in the solid state, as well as organic solvates.

The term "prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, H., Design of Prodrugs (1985) (Elsevier, Amsterdam). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a)_2$, —C(O)N($R^a)_2$, —N($R^a$)C(O)O$R^a$, —N($R^a$)C(O)$R^a$, —N($R^a$)C(O)N($R^a)_2$, N($R^a$)C(N-$R^a$)N($R^a)_2$, —N($R^a$)S(O)$_t R^a$ (where t is 1 or 2), —S(O)$_t$O$R^a$ (where t is 1 or 2), —S(O)$_t$N($R^a)_2$ (where t is 1 or 2), or PO$_3(R^a)_2$ where each $R^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons. The term "substituted alkoxy" refers to alkoxy wherein the alkyl constituent is substituted (i.e., —O—(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a)_2$, —C(O)N($R^a)_2$, —N($R^a$)C(O)O$R^a$, —N($R^a$)C(O)$R^a$, —N($R^a$)C(O)N($R^a)_2$, N($R^a$)C(N-$R^a$)N($R^a)_2$, —N($R^a$)S(O)$_t R^a$ (where t is 1 or 2), —S(O)$_t$O$R^a$ (where t is 1 or 2), —S(O)$_t$N($R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —$N(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ substituents other than hydrogen, they can be combined with the nitrogen atom to form a 4-, 5-, 6- or 7-membered ring. For example, —$N(R^a)_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid.

"Aromatic" or "aryl" or "Ar" refers to an aromatic radical with six to fourteen ring atoms (e.g., $C_6$-$C_{14}$ aromatic or $C_6$-$C_{14}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. ($C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkoxy" refers to a cycloalkyl group attached to the parent structure through an oxygen. Examples include, but are not limited to, cyclopropyloxyl and cyclohexyloxyl.

"Cyano" refers to a —CN radical.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The term "halo$C_{n-m}$alkyl" includes $C_{n-m}$alkyl structures that are substituted with one or more halo groups or with combinations thereof. For example, the terms "fluoroalkyl" and "trifluoroalkyl" include haloalkyl in which the halo is fluorine.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4- benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofuranzanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Substituted heteroaryl also includes ring systems substituted with one or more oxide (—O—) substituents, such as, for example, pyridinyl N-oxides. Other non-limiting examples of heterocyclic rings include azetidine, pyrrolidine, imidazolidine, piperidine and piperazine.

"Hydroxy" refers to a —OH radical.

"Nitro" refers to the —NO$_2$ radical.

The terms "antibody" and its plural form "antibodies" refer to whole immunoglobulins and any antigen-binding fragment ("antigen-binding portion") or single chains thereof. An "antibody" further refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as V$_H$) and a heavy chain constant region. The heavy chain constant region is comprised of three domains, CH1, CH2 and CH3. Each light chain is comprised of a light chain variable region (abbreviated herein as V$_L$) and a light chain constant region. The light chain constant region is comprised of one domain, C$_L$. The V$_H$ and V$_L$ regions of an antibody may be further subdivided into regions of hypervariability, which are referred to as complementarity determining regions (CDR) or hypervariable regions (HVR), and which can be interspersed with regions that are more conserved, termed framework regions (FR). Each V$_H$ and V$_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen epitope or epitopes. The constant regions of the antibodies may mediate the binding of the immunoglobulin to host tissues or factors, including various cells of the immune system (e.g., effector cells) and the first component (Clq) of the classical complement system.

The term "antigen" refers to a substance that induces an immune response. In some embodiments, an antigen is a molecule capable of being bound by an antibody or a TCR if presented by major histocompatibility complex (MHC) molecules. The term "antigen", as used herein, also encompasses T cell epitopes. An antigen is additionally capable of being recognized by the immune system. In some embodiments, an antigen is capable of inducing a humoral immune response or a cellular immune response leading to the activation of B lymphocytes and/or T lymphocytes. In some cases, this may require that the antigen contains or is linked to a Th cell epitope. An antigen can also have one or more epitopes (e.g., B- and T-epitopes). In some embodiments, an antigen will preferably react, typically in a highly specific and selective manner, with its corresponding antibody or TCR and not with the multitude of other antibodies or TCRs which may be induced by other antigens.

The terms "monoclonal antibody," "mAb," "monoclonal antibody composition," or their plural forms refer to a preparation of antibody molecules of single molecular composition. A monoclonal antibody composition displays a single binding specificity and affinity for a particular epitope. Monoclonal antibodies specific to certain receptors can be made using knowledge and skill in the art of injecting test subjects with suitable antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

The terms "antigen-binding portion" or "antigen-binding fragment" of an antibody (or simply "antibody portion" or "fragment"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the V$_L$, V$_H$, C$_L$ and CH1 domains; (ii) a F(ab')2 fragment, a bivalent fragment comprising two Fab fragments linked by a disulfide bridge at the hinge region; (iii) a Fd fragment consisting of the V$_H$ and CH1 domains; (iv) a Fv fragment consisting of the V$_L$ and V$_H$ domains of a single arm of an antibody, (v) a domain antibody (dAb) fragment (Ward, et al., *Nature*, 1989, 341, 544-546), which may consist of a $V_H$ or a $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see, e.g., Bird, et al., *Science* 1988, 242, 423-426; and Huston, et al., *Proc. Natl. Acad. Sci. USA* 1988, 85, 5879-5883). Such scFv antibodies are also intended to be encompassed within the terms "antigen-binding portion" or "antigen-binding fragment" of an antibody. These antibody fragments are obtained using conventional techniques known to those with skill in the art, and the fragments are screened for utility in the same manner as are intact antibodies.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). The term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In an embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, including a conjugate of the antibody and another active pharmaceutical ingredient or antibody. The terms "conjugate," "antibody-drug conjugate", "ADC," or "immunoconjugate" refers to an antibody, or a fragment thereof, conjugated to another therapeutic moiety, which can be conjugated to antibodies described herein using methods available in the art.

The terms "humanized antibody," "humanized antibodies," and "humanized" are intended to refer to antibodies in which CDR sequences derived from the germline of another mammalian species, such as a mouse, have been grafted onto human framework sequences. Additional framework region modifications may be made within the human framework sequences. Humanized forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a 15 hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones, et al., *Nature* 1986, 321, 522-525; Riechmann, et al., *Nature* 1988, 332, 323-329; and Presta, *Curr. Op. Struct. Biol.* 1992, 2, 593-596. The antibodies described herein may also be modified to employ any Fc variant which is known to impart an improvement (e.g., reduction) in effector function and/or FcR binding. The Fc variants may include, for example, any one of the amino acid substitutions disclosed in International Patent Application Publication Nos. WO 1988/07089 A1, WO 1996/14339 A1, WO 1998/05787 A1, WO 1998/23289 A1, WO 1999/51642 A1, WO 99/58572 A1, WO 2000/09560 A2, WO 2000/32767 A1, WO 2000/42072 A2, WO 2002/44215 A2, WO 2002/060919 A2, WO 2003/074569 A2, WO 2004/016750 A2, WO 2004/029207 A2, WO 2004/035752 A2, WO 2004/063351 A2, WO 2004/074455 A2, WO 2004/099249 A2, WO 2005/040217 A2, WO 2005/070963 A1, WO 2005/077981 A2, WO 2005/092925 A2, WO 2005/123780 A2, WO 2006/019447 A1, WO 2006/047350 A2, and WO 2006/085967 A2; and U.S. Pat. Nos. 5,648,260; 5,739,277; 5,834,250; 5,869,046; 6,096,871; 6,121,022; 6,194,551; 6,242,195; 6,277,375;

6,528,624; 6,538,124; 6,737,056; 6,821,505; 6,998,253; and 7,083,784; the disclosures of which are incorporated by reference herein.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., European Patent No. EP 404,097, International Patent Publication No. WO 93/11161; and Bolliger, et al., *Proc. Natl. Acad. Sci. USA* 1993, 90, 6444-6448.

The term "glycosylation" refers to a modified derivative of an antibody. An aglycoslated antibody lacks glycosylation. Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Aglycosylation may increase the affinity of the antibody for antigen, as described in U.S. Pat. Nos. 5,714,350 and 6,350,861. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see e.g. U.S. Patent Publication No. 2004/0110704 or Yamane-Ohnuki, et al., *Biotechnol. Bioeng.*, 2004, 87, 614-622). As another example, European Patent No. EP 1,176,195 describes a cell line with a functionally disrupted FUT8 gene, which encodes a fucosyl transferase, such that antibodies expressed in such a cell line exhibit hypofucosylation by reducing or eliminating the alpha 1,6 bond-related enzyme, and also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). International Patent Publication WO 03/035835 describes a variant CHO cell line, Lec 13 cells, with reduced ability to attach fucose to Asn(297)-linked carbohydrates, also resulting in hypofucosylation of antibodies expressed in that host cell (see also Shields, et al., *J. Biol. Chem.* 2002, 277, 26733-26740. International Patent Publication WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana, et al., *Nat. Biotech.* 1999, 17, 176-180). Alternatively, the fucose residues of the antibody may be cleaved off using a fucosidase enzyme. For example, the fucosidase alpha-L-fucosidase removes fucosyl residues from antibodies as described in Tarentino, et al., *Biochem.* 1975, 14, 5516-5523.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$)alkoxy- or aryloxy-polyethylene glycol or polyethylene glycol-maleimide. The antibody to be pegylated may be an aglycosylated antibody. Methods for pegylation are known in the art and can be applied to the antibodies of the invention, as described for example in European Patent Nos. EP 0154316 and EP 0401384 and U.S. Pat. No. 5,824,778, the disclosures of each of which are incorporated by reference herein.

The terms "fusion protein" or "fusion polypeptide" refer to proteins that combine the properties of two or more individual proteins. Such proteins have at least two heterologous polypeptides covalently linked either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. The term encompasses conservatively modified variants, polymorphic variants, alleles, mutants, subsequences, interspecies homologs, and immunogenic fragments of the antigens that make up the fusion protein. Fusion proteins of the disclosure can also comprise additional copies of a component antigen or immunogenic fragment thereof. The fusion protein may contain one or more binding domains linked together and further linked to an Fc domain, such as an IgG Fc domain. Fusion proteins may be further linked together to mimic a monoclonal antibody and provide six or more binding domains. Fusion proteins may be produced by recombinant methods as is known in the art. Preparation of fusion proteins are known in the art and are described, e.g., in International Patent Application Publication Nos. WO 1995/027735 A1, WO 2005/103077 A1, WO 2008/025516 A1, WO 2009/007120 A1, WO 2010/003766 A1, WO 2010/010051 A1, WO 2010/078966 A1, U.S. Patent Application Publication Nos. US 2015/0125419 A1 and US 2016/0272695 A1, and U.S. Pat. No. 8,921,519, the disclosures of each of which are incorporated by reference herein.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The term "conservative amino acid substitutions" in means amino acid sequence modifications which do not abrogate the binding of an antibody or fusion protein to the antigen. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an antibody is preferably replaced with another amino acid residue from the same class. Methods of identifying amino acid conservative substitutions which do not eliminate antigen binding are well-known in the art (see, e.g., Brummell, et al., *Biochemistry* 1993, 32, 1180-1187; Kobayashi, et al., *Protein Eng.* 1999, 12, 879-884 (1999); and Burks, et al., *Proc. Natl. Acad. Sci. USA* 1997, 94, 412-417.

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, Calif.) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

Nucleic acid sequences implicitly encompass conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. Batzer, et al., *Nucleic Acid Res.* 1991, 19, 5081; Ohtsuka, et al., *J. Biol. Chem.* 1985, 260, 2605-2608; Rossolini, et al., *Mol. Cell. Probes* 1994, 8, 91-98. The term nucleic acid is used interchangeably with cDNA, mRNA, oligonucleotide, and polynucleotide.

The term "biosimilar" means a biological product, including a monoclonal antibody or protein, that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference IL-2 protein is aldesleukin (PROLEUKIN), a protein approved by drug regulatory authorities with reference to aldesleukin is a "biosimilar to" aldesleukin or is a "biosimilar thereof" of aldesleukin. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorized, approved for authorization or subject of an application for authorization under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorized by the EMA. However, in some instances, the biosimilar may be compared to a biological medicinal product which has been authorized outside the European Economic Area (a non-EEA authorized "comparator") in certain studies. Such studies include for example certain clinical and in vivo non-clinical studies. As used herein, the term "biosimilar" also relates to a biological medicinal product which has been or may be compared to a non-EEA authorized comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorized or considered suitable for authorization. In certain circumstances, the biosimilar exhibits different binding characteristics as compared to the reference medicinal product, wherein the different binding characteristics are considered by a Regulatory Authority such as the EMA not to be a barrier for authorization as a similar biological product. The term "biosimilar" is also used synonymously by other national and regional regulatory agencies.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

Potassium Channel Agonists

In an embodiment, the potassium channel agonist is a $K_{Ca}3.1$ agonist, activator, or opener, also known as an IK channel agonist, activator, or opener and a $K_{Ca}3.1$ channel agonist, activator, or opener. $K_{Ca}3.1$ is also known as hIKCa, hKCa4, hSK4, intermediate conductance calcium-activated potassium channel, and small conductance calcium-activated potassium channel 4.

In an embodiment, the $K_{Ca}3.1$ agonist is a benzothiazole derivative, or a pharmaceutically-acceptable salt, cocrystal, solvate, or prodrug thereof. In an embodiment, the $K_{Ca}3.1$ agonist is a benzimidazole derivative, or a pharmaceutically-acceptable salt, cocrystal, solvate, or prodrug thereof. Suitable benzothiazole and benzimidazole derivatives are described in Sankaranarayanan, et al., *Mol. Pharmacol.* 2009, 75, 281-95, the disclosure of which is incorporated by reference herein.

In an embodiment, the $K_{Ca}3.1$ agonist is a compound according to Formula (1):

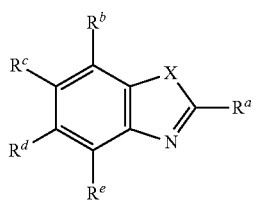

Formula (1)

or a pharmaceutically-acceptable salt, cocrystal, solvate, or prodrug thereof, wherein
  $R^a$ is selected from the group consisting of halo, cyano, hydroxy, thiol, $(C_{1-6})$alkyl, —$NH_2$, and —$NR^1R^2$;
  $R^1$ and $R^2$ are independently H or $(C_{1-6})$alkyl;
  X is selected from the group consisting of S, O, and NH;
  $R^b$ and $R^c$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^b$ and $R^c$ together with the carbon atoms to which they are attached form a ring selected from the group consisting of an aryl, naphthyl, anthryl, heteroaryl, cycloalkyl, and heterocycloalkyl ring; and
  $R^d$ and $R^e$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^d$ and $R^e$ together with the carbon atoms to which they are attached form a ring selected from the group consisting of an aryl, naphthyl, anthryl, heteroaryl, cycloalkyl, and heterocycloalkyl ring;

with the proviso that if $R^b$ and $R^c$ form a ring, then $R^d$ and $R^e$ do not form a ring, and if $R^d$ and $R^e$ form a ring, then $R^b$ and $R^c$ do not form a ring.

In an embodiment, the $K_{Ca}3.1$ agonist is a compound according to Formula (1), or a pharmaceutically-acceptable salt, cocrystal, solvate, or prodrug thereof, wherein
  $R^a$ is selected from thiol and —$NH_2$;
  $R^b$ and $R^c$ are independently selected from the group consisting of hydrogen, $(C_{1-3})$alkyl, $(C_{1-3})$alkoxyl, halo, nitro, unsubstituted aryl, $(C_{1-3})$alkyl and or $R^b$ and $R^c$ together with the carbon atom to which they are attached together form a 5 or 6 membered ring selected from the group consisting of an aryl, heteroaryl, cycloalkyl, and heterocycloalkyl ring; and
  $R^d$ and $R^e$ are independently selected from the group consisting of hydrogen, $(C_{1-3})$alkyl, $(C_{1-3})$alkoxyl, halo, nitro, unsubstituted aryl, $(C_{1-3})$alkyl and or $R^d$ and $R^e$ together with the carbon atom to which they are attached together form a 5 or 6 membered ring selected from the group consisting of an aryl, heteroaryl, cycloalkyl, and heterocycloalkyl ring,
  with the proviso that if $R^b$ and $R^c$ form a ring, then $R^d$ and $R^e$ do not form a ring, and if $R^d$ and $R^e$ form a ring, then $R^b$ and $R^c$ do not form a ring.

In an embodiment, the $K_{Ca}3.1$ agonist is SKA-31, also known as naphtho[1,2-d]thiazol-2-ylamine (Formula (2)):

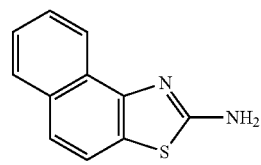 [SMILES: Nc1nc2c(ccc3ccccc32)s1]

Formula (2)

or a pharmaceutically-acceptable salt, cocrystal, solvate, or prodrug thereof. SKA-31 is commercially available from multiple sources (Chemical Abstracts Service (CAS) No. 40172-65-4), including Tocris Bioscience, Avonmouth, Bristol, UK, and Sigma-Aldrich Co., St. Louis, Mo., USA. The properties and synthesis of SKA-31 are described in Sankaranarayanan, et al., *Mol. Pharmacol.* 2009, 75, 281-95, the disclosure of which is incorporated by reference herein.

In an embodiment, the $K_{Ca}3.1$ agonist is SKA-20, also known as anthra[2,1-d]thiazol-2-ylamine (Formula (3)):

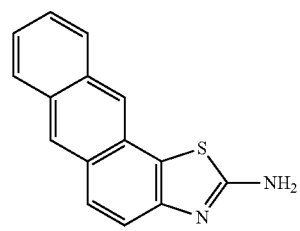 [SMILES: Nc1nc2ccc3cc4ccccc4cc3c2s1]

Formula (3)

or a pharmaceutically-acceptable salt, cocrystal, solvate, or prodrug thereof. The properties and synthesis of SKA-20 are described in Sankaranarayanan, et al., *Mol. Pharmacol.* 2009, 75, 281-95, the disclosure of which is incorporated by reference herein.

In an embodiment, the $K_{Ca}3.1$ agonist is NS309, also known as 6,7-dichloro-1H-indole-2,3-dione 3-oxime (Formula (4)):

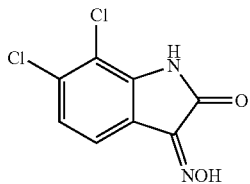

Formula (4)

or a pharmaceutically-acceptable salt, cocrystal, solvate, or prodrug thereof. NS309 is commercially available from multiple sources (CAS No. 18711-16-5), including Tocris Bioscience. The properties and synthesis of NS309 are described in U.S. Pat. No. 6,969,729 and Strøbæk, et al., Biochim. Biophys. Acta 2004, 1665, 1-5, the disclosures of which are incorporated by reference herein.

In an embodiment, the $K_{Ca}3.1$ agonist is a compound according to Formula (5):

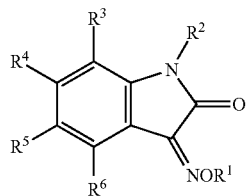

Formula (5)

or a pharmaceutically-acceptable salt, cocrystal, solvate, or prodrug thereof; wherein $R^1$ represents hydrogen; an alkyl group; a cycloalkyl group; an acyl group; a phenyl or a benzyl group, which phenyl and benzyl groups are unsubstituted or are substituted one or more times with substituents selected from halogen, $-NO_2$, $-CN$, $-CF_3$, alkyl, cycloalkyl, hydroxy, and alkoxy; a group of the formula $-CH_2CN$; a group of the formula $-CH_2CO_2R'$, wherein R' represents hydrogen or alkyl; a group of the formula $-CH_2CONR^{IV}R^V$, wherein $R^{IV}$ and $R^V$ independently represents hydrogen, alkyl, phenyl or benzyl, which phenyl and benzyl groups are unsubstituted or are substituted one or more times with halogen and/or alkyl, or $R^{IV}$ and $R^V$ together with the N-atom to which they are attached form a heterocyclic 4 to 7 membered monocyclic group, which heterocyclic group are unsubstituted or are substituted one or more times with substituents selected from the group consisting of halogen, alkyl, cycloalkyl, alkyloxy, cycloalkyloxy, phenyl or benzyl; or a group of the formula $-CH_2C(=NOH)NH_2$;

$R^2$ represents hydrogen; an alkyl group; a cycloalkyl group; a group of the formula $-CH_2CO_2R'$, wherein R' represents hydrogen or an alkyl group; a phenyl or a benzyl group, which phenyl and benzyl groups are unsubstituted or are substituted one or more times with substituents selected from halogen, $-NO_2$, $-CN$, $-CF_3$, alkyl, cycloalkyl, hydroxy, and alkoxy; and $R^3$, $R^4$, $R^5$, and $R^6$ independently of each another represents hydrogen; halogen; $-NO_2$; $-CN$; $-CF_3$; an alkyl group; an alkoxy group; a phenyl or a benzyl group, which phenyl and benzyl groups are unsubstituted or are substituted one or more times with substituents selected from halogen, $-NO_2$, $-CN$, $-CF_3$, alkyl, cycloalkyl, hydroxy, and alkoxy; or a group of the formula $-SO_2NR''R'''$, wherein R'' and R''' independently of each another represents hydrogen or an alkyl group;

or $R^5$ and $R^6$ are as defined above, and $R^3$ and $R^4$ together form an additional 4 to 7 membered fused ring, which fused ring may be aromatic, saturated or partially saturated, and which fused ring are unsubstituted or are substituted one or more times with substituents selected from the group consisting of halogen, $-NO_2$, $-CN$, $-CF_3$, and a group of the formula $-SO_2NR''R'''$, wherein R'' and R''' independently of each another represents hydrogen or an alkyl group.

The properties and synthesis of compounds according to Formula (5) are described in U.S. Pat. No. 6,969,729, the disclosure of which is incorporated by reference herein.

In an embodiment, the $K_{Ca}3.1$ agonist is 1-EBIO, also known as 1-ethyl-1,3-dihydro-2H-benzimidazol-2-one and 1-ethyl-2-benzimidazolinone (Formula (6)):

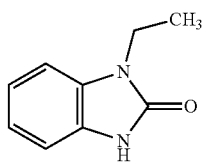

Formula (6)

or a pharmaceutically-acceptable salt, cocrystal, solvate, or prodrug thereof. 1-EBIO is commercially available from multiple sources (CAS No. 10045-45-1), including Tocris Bioscience and Sigma-Aldrich. The properties and synthesis of 1-EBIO are described in Adeagbo, Eur. J. Pharmacol. 1999, 379, 151-59 and Devor, et al., Am. J. Physiol. 1996, 271, L775-L784, the disclosures of which are incorporated by reference herein.

In an embodiment, the $K_{Ca}3.1$ agonist is DCEBIO, also known as 5,6-dichloro-1-ethyl-1,3-dihydro-2H-benzimidazol-2-one and DC-EBIO (Formula (7)):

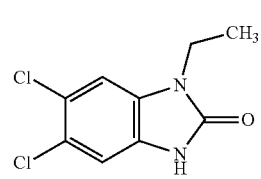

Formula (7)

or a pharmaceutically-acceptable salt, cocrystal, solvate, or prodrug thereof. DCEBIO is commercially available from multiple sources (CAS No. 60563-36-2), including Tocris Bioscience and Sigma-Aldrich. The properties and synthesis of DCEBIO are described in Singh, et al., J. Pharmacol. Exp. Ther. 2001, 296, 600-611, the disclosure of which is incorporated by reference herein.

In an embodiment, the $K_{Ca}3.1$ agonist is riluzole, also known as 2-amino-6-trifluoromethoxybenzothiazole or 6-(trifluoromethoxy)benzo[d]thiazol-2-amine (Formula (8)):

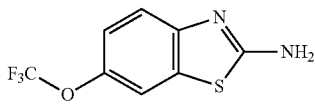

Formula (8)

or a pharmaceutically-acceptable salt, cocrystal, solvate, or prodrug thereof. Riluzole is commercially available from multiple sources under the trade names RILUTEK and TEGLUTIK, and may also be obtained from Sigma-Aldrich Co., St. Louis, Mo., USA (CAS No. 1744-22-5). The properties and synthesis of riluzole are described in U.S. Pat. No. 4,370,338 and Grunnet, et al., *Neuropharmacology* 2001, 40, 879-887, the disclosures of which are incorporated by reference herein.

In an embodiment, the $K_{Ca}3.1$ agonist is a compound of Formula (9a) or a compound of Formula (9b):

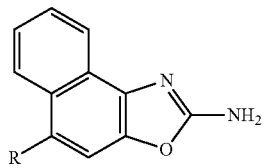

Formula (9a)

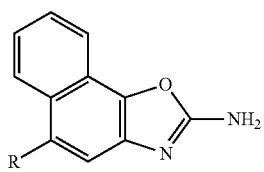

Formula (9b)

or a pharmaceutically-acceptable salt, cocrystal, solvate, or prodrug thereof; wherein R is selected from halo, cyano, hydroxy, $(C_{1-6})$alkyl, $(C_{3-7})$cycloalkyl, $(C_{1-6})$alkoxy, $(C_{3-7})$cycloalkoxy, halo $(C_{1-6})$alkyl and —$NR^1R^2$; and $R^1$ and $R^2$ are independently selected from hydrogen, $(C_{1-6})$alkyl and $(C_{3-7})$cycloalkyl or $R_1$ and $R_2$ together with the nitrogen atom to which they are attached together form a 4 to 7 membered heterocyclic ring.

The properties and synthesis of compounds of Formula (9a) and (9b) are described in International Patent Application Publication No. WO 2015/164816 A2, the disclosure of which is incorporated by reference herein.

In an embodiment, the $K_{Ca}3.1$ agonist is 5-methylnaphtho [1,2-d]oxazol-2-amine (Formula (10a)) or 5-methylnaphtho [2,1-d]oxazol-2-amine (Formula (10b), also known as SKA-121):

Formula (10a)

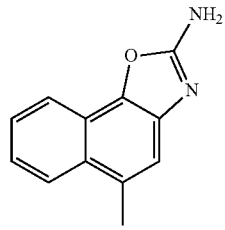

Formula (10b)

or a pharmaceutically-acceptable salt, cocrystal, solvate, or prodrug thereof.

The properties and synthesis of compounds of Formula (10a) and Formula (10b) (SKA-121) are described in International Patent Application Publication No. WO 2015/164816 A2 and Coleman, et al., *Mol. Pharmacol.* 2014, 86, 342-57, the disclosures of which are incorporated by reference herein.

In an embodiment, the $K_{Ca}3.1$ agonist is 6-(trifluoromethoxy)-1H-benzo[d]imidazol-2-amine, also known as SKA-12 (Formula (11)):

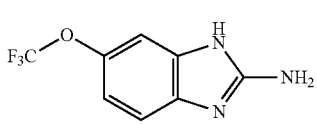

Formula (11)

or a pharmaceutically-acceptable salt, cocrystal, solvate, or prodrug thereof. The properties and synthesis of SKA-12 are described in Sankaranarayanan, et al., *Mol. Pharmacol.* 2009, 75, 281-95, the disclosure of which is incorporated by reference herein.

In an embodiment, the $K_{Ca}3.1$ agonist is 6-methoxybenzo [d]thiazole-2-thiol, also known as SKA-5 (Formula (12)):

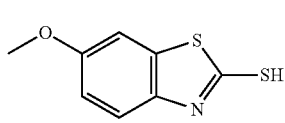

Formula (12)

or a pharmaceutically-acceptable salt, cocrystal, solvate, or prodrug thereof. The properties and synthesis of SKA-5 are described in Sankaranarayanan, et al., *Mol. Pharmacol.* 2009, 75, 281-95, the disclosure of which is incorporated by reference herein.

In an embodiment, the $K_{Ca}3.1$ agonist is 6-nitrobenzo[d] thiazole-2-thiol, also known as SKA-6 (Formula (13)):

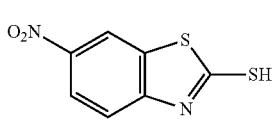

Formula (13)

or a pharmaceutically-acceptable salt, cocrystal, solvate, or prodrug thereof. The properties and synthesis of SKA-6 are described in Sankaranarayanan, et al., *Mol. Pharmacol.* 2009, 75, 281-95, the disclosure of which is incorporated by reference herein.

In an embodiment, the $K_{Ca}3.1$ agonist is 6-(trifluoromethoxy)-1H-benzo[d]imidazole-2-thiol, also known as SKA-46 (Formula (14)):

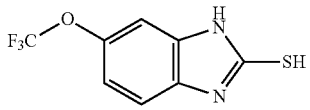

Formula (14)

or a pharmaceutically-acceptable salt, cocrystal, solvate, or prodrug thereof. The properties and synthesis of SKA-46 are described in Sankaranarayanan, et al., *Mol. Pharmacol.* 2009, 75, 281-95, the disclosure of which is incorporated by reference herein.

In an embodiment, the $K_{Ca}3.1$ agonist is 6-(difluoromethoxy)-1H-benzo[d]imidazole-2-thiol, also known as SKA-47 (Formula (15)):

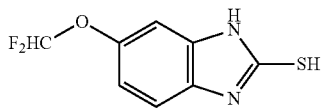

Formula (15)

or a pharmaceutically-acceptable salt, cocrystal, solvate, or prodrug thereof. The properties and synthesis of SKA-47 are described in Sankaranarayanan, et al., *Mol. Pharmacol.* 2009, 75, 281-95, the disclosure of which is incorporated by reference herein.

In an embodiment, the $K_{Ca}3.1$ agonist is 4-(4-(trifluoromethoxy)phenyl)thiazol-2-amine, also known as SKA-41 (Formula (17)):

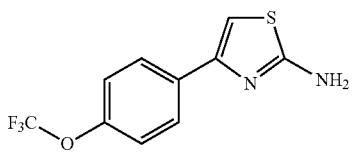

Formula (17)

or a pharmaceutically-acceptable salt, cocrystal, solvate, or prodrug thereof. The properties and synthesis of SKA-41 are described in Sankaranarayanan, et al., *Mol. Pharmacol.* 2009, 75, 281-95, the disclosure of which is incorporated by reference herein.

In an embodiment, the $K_{Ca}3.1$ agonist is benzo[d]thiazol-2-amine, also known as SKA-1 (Formula (18)):

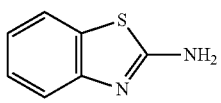

Formula (18)

or a pharmaceutically-acceptable salt, cocrystal, solvate, or prodrug thereof. The properties and synthesis of SKA-1 are described in Sankaranarayanan, et al., *Mol. Pharmacol.* 2009, 75, 281-95, the disclosure of which is incorporated by reference herein.

In an embodiment, the $K_{Ca}3.1$ agonist is benzo[d]thiazol-2-amine, also known as SKA-36 (Formula (19)):

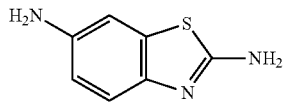

Formula (19)

or a pharmaceutically-acceptable salt, cocrystal, solvate, or prodrug thereof. The properties and synthesis of SKA-36 are described in Sankaranarayanan, et al., *Mol. Pharmacol.* 2009, 75, 281-95, the disclosure of which is incorporated by reference herein.

In an embodiment, the $K_{Ca}3.1$ agonist is 6-nitrobenzo[d]thiazol-2-amine, also known as SKA-4 (Formula (20)):

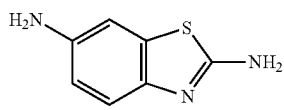

Formula (20)

or a pharmaceutically-acceptable salt, cocrystal, solvate, or prodrug thereof. The properties and synthesis of SKA-4 are described in Sankaranarayanan, et al., *Mol. Pharmacol.* 2009, 75, 281-95, the disclosure of which is incorporated by reference herein.

In an embodiment, the $K_{Ca}3.1$ agonist is 6-(methylsulfonyl)benzo[d]thiazol-2-amine, also known as SKA-16 (Formula (21)):

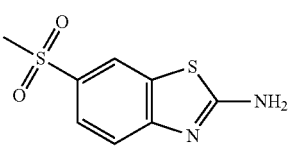

Formula (21)

or a pharmaceutically-acceptable salt, cocrystal, solvate, or prodrug thereof. The properties and synthesis of SKA-16 are described in Sankaranarayanan, et al., *Mol. Pharmacol.* 2009, 75, 281-95, the disclosure of which is incorporated by reference herein.

In an embodiment, the $K_{Ca}3.1$ agonist is 1-(2-aminobenzo[d]thiazol-6-yl)ethan-1-one, also known as SKA-24 (Formula (22)):

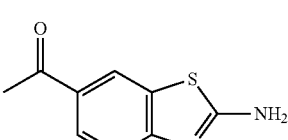

Formula (22)

or a pharmaceutically-acceptable salt, cocrystal, solvate, or prodrug thereof. The properties and synthesis of SKA-24 are described in Sankaranarayanan, et al., *Mol. Pharmacol.* 2009, 75, 281-95, the disclosure of which is incorporated by reference herein.

In an embodiment, the $K_{Ca}3.1$ agonist is 6-methoxybenzo[d]thiazol-2-amine, also known as SKA-2 (Formula (23)):

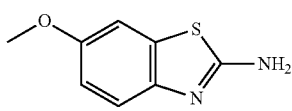

Formula (23)

or a pharmaceutically-acceptable salt, cocrystal, solvate, or prodrug thereof. The properties and synthesis of SKA-2 are described in Sankaranarayanan, et al., *Mol. Pharmacol.* 2009, 75, 281-95, the disclosure of which is incorporated by reference herein.

In an embodiment, the $K_{Ca}3.1$ agonist is 6-methoxybenzo[d]thiazol-2-amine, also known as SKA-17 (Formula (24)):

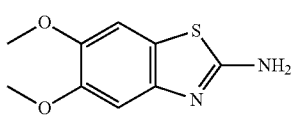

Formula (24)

or a pharmaceutically-acceptable salt, cocrystal, solvate, or prodrug thereof. The properties and synthesis of SKA-17 are described in Sankaranarayanan, et al., *Mol. Pharmacol.* 2009, 75, 281-95, the disclosure of which is incorporated by reference herein.

In an embodiment, the $K_{Ca}3.1$ agonist is 5-chloro-6-methoxybenzo[d]thiazol-2-amine, also known as SKA-13 (Formula (25)):

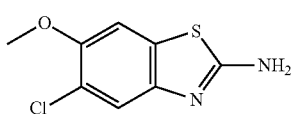

Formula (25)

or a pharmaceutically-acceptable salt, cocrystal, solvate, or prodrug thereof. The properties and synthesis of SKA-13 are described in Sankaranarayanan, et al., *Mol. Pharmacol.* 2009, 75, 281-95, the disclosure of which is incorporated by reference herein.

In an embodiment, the $K_{Ca}3.1$ agonist is 6-benzylbenzo[d]thiazol-2-amine, also known as SKA-7 (Formula (26)):

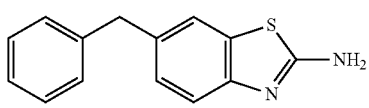

Formula (26)

or a pharmaceutically-acceptable salt, cocrystal, solvate, or prodrug thereof. The properties and synthesis of SKA-7 are described in Sankaranarayanan, et al., *Mol. Pharmacol.* 2009, 75, 281-95, the disclosure of which is incorporated by reference herein.

In an embodiment, the $K_{Ca}3.1$ agonist is 6-phenoxybenzo[d]thiazol-2-amine, also known as SKA-32 (Formula (27)):

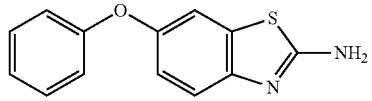

Formula (27)

or a pharmaceutically-acceptable salt, cocrystal, solvate, or prodrug thereof. The properties and synthesis of SKA-32 are described in Sankaranarayanan, et al., *Mol. Pharmacol.* 2009, 75, 281-95, the disclosure of which is incorporated by reference herein.

In an embodiment, the $K_{Ca}3.1$ agonist is (2-aminobenzo[d]thiazol-6-yl)(phenyl)methanone, also known as SKA-22 (Formula (28)):

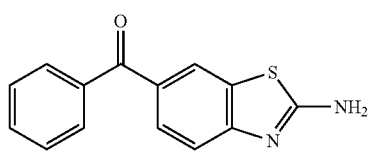

Formula (28)

or a pharmaceutically-acceptable salt, cocrystal, solvate, or prodrug thereof. The properties and synthesis of SKA-22 are described in Sankaranarayanan, et al., *Mol. Pharmacol.* 2009, 75, 281-95, the disclosure of which is incorporated by reference herein.

In an embodiment, the $K_{Ca}3.1$ agonist is (2-aminobenzo[d]thiazol-6-yl)(phenyl)methanone, also known as SKA-48 (Formula (29)):

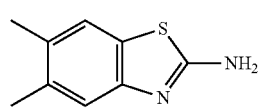

Formula (29)

or a pharmaceutically-acceptable salt, cocrystal, solvate, or prodrug thereof. The properties and synthesis of SKA-48 are described in Sankaranarayanan, et al., *Mol. Pharmacol.* 2009, 75, 281-95, the disclosure of which is incorporated by reference herein.

In an embodiment, the $K_{Ca}3.1$ agonist is 6-fluorobenzo[d]thiazol-2-amine, also known as SKA-18 (Formula (29)):

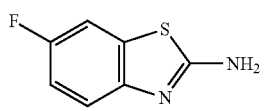

Formula (29)

or a pharmaceutically-acceptable salt, cocrystal, solvate, or prodrug thereof. The properties and synthesis of SKA-18 are described in Sankaranarayanan, et al., *Mol. Pharmacol.* 2009, 75, 281-95, the disclosure of which is incorporated by reference herein.

In an embodiment, the $K_{Ca}3.1$ agonist is 5,6-difluorobenzo[d]thiazol-2-amine, also known as SKA-42 (Formula (30)):

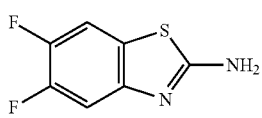

Formula (30)

or a pharmaceutically-acceptable salt, cocrystal, solvate, or prodrug thereof. The properties and synthesis of SKA-42 are described in Sankaranarayanan, et al., *Mol. Pharmacol.* 2009, 75, 281-95, the disclosure of which is incorporated by reference herein.

In an embodiment, the $K_{Ca}3.1$ agonist is 6-chlorobenzo[d]thiazol-2-amine, also known as SKA-3 (Formula (31)):

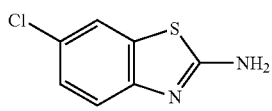

Formula (31)

or a pharmaceutically-acceptable salt, cocrystal, solvate, or prodrug thereof. The properties and synthesis of SKA-3 are described in Sankaranarayanan, et al., *Mol. Pharmacol.* 2009, 75, 281-95, the disclosure of which is incorporated by reference herein.

In an embodiment, the $K_{Ca}3.1$ agonist is 5-(trifluoromethoxy)benzo[d]thiazol-2-amine, also known as SKA-8 (Formula (32)):

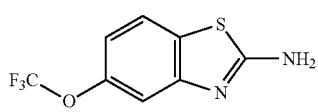

Formula (32)

or a pharmaceutically-acceptable salt, cocrystal, solvate, or prodrug thereof. The properties and synthesis of SKA-8 are described in Sankaranarayanan, et al., *Mol. Pharmacol.* 2009, 75, 281-95, the disclosure of which is incorporated by reference herein.

In an embodiment, the $K_{Ca}3.1$ agonist is 4-(trifluoromethoxy)benzo[d]thiazol-2-amine, also known as SKA-35 (Formula (33)):

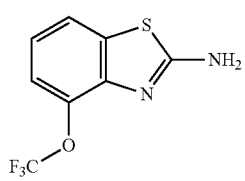

Formula (33)

or a pharmaceutically-acceptable salt, cocrystal, solvate, or prodrug thereof. The properties and synthesis of SKA-35 are described in Sankaranarayanan, et al., *Mol. Pharmacol.* 2009, 75, 281-95, the disclosure of which is incorporated by reference herein.

In an embodiment, the $K_{Ca}3.1$ agonist is 6-(trifluoromethyl)benzo[d]thiazol-2-amine, also known as SKA-51 (Formula (34)):

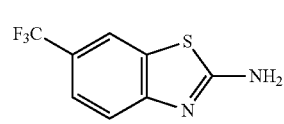

Formula (34)

or a pharmaceutically-acceptable salt, cocrystal, solvate, or prodrug thereof. The properties and synthesis of SKA-51 are described in Sankaranarayanan, et al., *Mol. Pharmacol.* 2009, 75, 281-95, the disclosure of which is incorporated by reference herein.

In an embodiment, the $K_{Ca}3.1$ agonist is 5-(trifluoromethyl)benzo[d]thiazol-2-amine, also known as SKA-34 (Formula (35)):

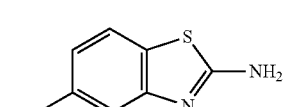

Formula (35)

or a pharmaceutically-acceptable salt, cocrystal, solvate, or prodrug thereof. The properties and synthesis of SKA-34 are described in Sankaranarayanan, et al., *Mol. Pharmacol.* 2009, 75, 281-95, the disclosure of which is incorporated by reference herein.

In an embodiment, the $K_{Ca}3.1$ agonist is 6-((trifluoromethyl)thio)benzo[d]thiazol-2-amine, also known as SKA-19 (Formula (36)):

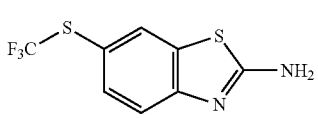

Formula (36)

or a pharmaceutically-acceptable salt, cocrystal, solvate, or prodrug thereof. The properties and synthesis of SKA-19 are described in Sankaranarayanan, et al., *Mol. Pharmacol.* 2009, 75, 281-95, the disclosure of which is incorporated by reference herein.

In an embodiment, the $K_{Ca}3.1$ agonist is 6-(chlorodifluoromethoxy)benzo[d]thiazol-2-amine, also known as SKA-11 (Formula (37)):

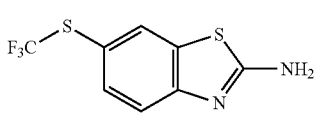

Formula (37)

or a pharmaceutically-acceptable salt, cocrystal, solvate, or prodrug thereof. The properties and synthesis of SKA-11 are described in Sankaranarayanan, et al., *Mol. Pharmacol.* 2009, 75, 281-95, the disclosure of which is incorporated by reference herein.

In an embodiment, the $K_{Ca}3.1$ agonist is [2,4'-bibenzo[d]thiazol]-2'-amine, also known as SKA-53 (Formula (38)):

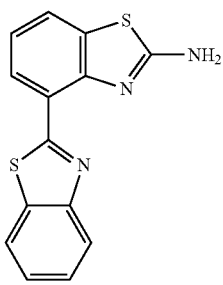

Formula (38)

or a pharmaceutically-acceptable salt, cocrystal, solvate, or prodrug thereof. The properties and synthesis of SKA-53 are described in Sankaranarayanan, et al., *Mol. Pharmacol.* 2009, 75, 281-95, the disclosure of which is incorporated by reference herein.

In an embodiment, the $K_{Ca}3.1$ agonist is 6,7-dihydro-5H-indeno[5,6-d]thiazol-2-amine, also known as SKA-29 (Formula (39)):

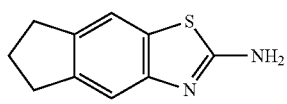

Formula (39)

or a pharmaceutically-acceptable salt, cocrystal, solvate, or prodrug thereof. The properties and synthesis of SKA-29 are described in Sankaranarayanan, et al., *Mol. Pharmacol.* 2009, 75, 281-95, the disclosure of which is incorporated by reference herein.

In an embodiment, the $K_{Ca}3.1$ agonist is 6,7,8,9-tetrahydronaphtho[2,1-d]thiazol-2-amine, also known as SKA-44 (Formula (40)):

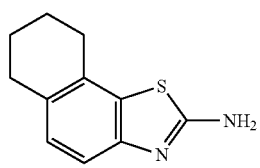

Formula (40)

or a pharmaceutically-acceptable salt, cocrystal, solvate, or prodrug thereof. The properties and synthesis of SKA-44 are described in Sankaranarayanan, et al., *Mol. Pharmacol.* 2009, 75, 281-95, the disclosure of which is incorporated by reference herein.

In an embodiment, the $K_{Ca}3.1$ agonist is 6,7,8,9-tetrahydronaphtho[1,2-d]thiazol-2-amine, also known as SKA-49 (Formula (41)):

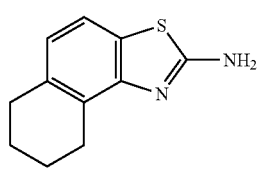

Formula (41)

or a pharmaceutically-acceptable salt, cocrystal, solvate, or prodrug thereof. The properties and synthesis of SKA-49 are described in Sankaranarayanan, et al., *Mol. Pharmacol.* 2009, 75, 281-95, the disclosure of which is incorporated by reference herein.

In an embodiment, the $K_{Ca}3.1$ agonist is naphtho[2,1-d]thiazol-2-amine, also known as SKA-45 (Formula (42)):

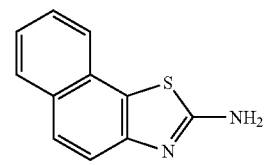

Formula (42)

or a pharmaceutically-acceptable salt, cocrystal, solvate, or prodrug thereof. The properties and synthesis of SKA-45 are described in Sankaranarayanan, et al., *Mol. Pharmacol.* 2009, 75, 281-95, the disclosure of which is incorporated by reference herein.

In an embodiment, the $K_{Ca}3.1$ agonist is 2-amino-6a,10a-dihydroanthra[2,1-d]thiazole-6,11-dione, also known as SKA-21 (Formula (43)):

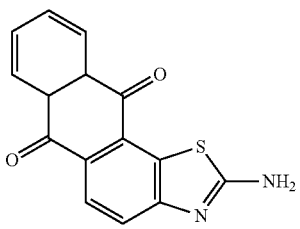

Formula (43)

or a pharmaceutically-acceptable salt, cocrystal, solvate, or prodrug thereof. The properties and synthesis of SKA-21 are described in Sankaranarayanan, et al., *Mol. Pharmacol.* 2009, 75, 281-95, the disclosure of which is incorporated by reference herein.

In an embodiment, the $K_{Ca}3.1$ agonist is 2-amino-7H-chromeno[6,5-d]thiazol-7-one, also known as SKA-26 (Formula (44)):

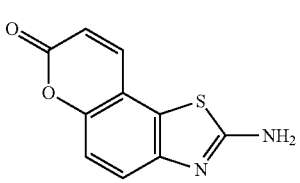

Formula (44)

or a pharmaceutically-acceptable salt, cocrystal, solvate, or prodrug thereof. The properties and synthesis of SKA-26 are described in Sankaranarayanan, et al., *Mol. Pharmacol.* 2009, 75, 281-95, the disclosure of which is incorporated by reference herein.

In an embodiment, the $K_{Ca}3.1$ agonist is benzo[1,2-d:4,5-d']bis(thiazole)-2,6-diamine, also known as SKA-50 (Formula (45)):

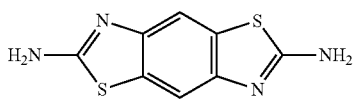

Formula (45)

or a pharmaceutically-acceptable salt, cocrystal, solvate, or prodrug thereof. The properties and synthesis of SKA-50 are described in Sankaranarayanan, et al., *Mol. Pharmacol.* 2009, 75, 281-95, the disclosure of which is incorporated by reference herein.

In an embodiment, the $K_{Ca}3.1$ agonist is benzo[1,2-d:4,3-d']bis(thiazole)-2-amine, also known as SKA-25 (Formula (40)):

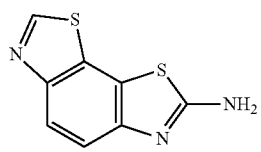

Formula (46)

or a pharmaceutically-acceptable salt, cocrystal, solvate, or prodrug thereof. The properties and synthesis of SKA-25 are described in Sankaranarayanan, et al., *Mol. Pharmacol.* 2009, 75, 281-95, the disclosure of which is incorporated by reference herein.

In an embodiment, the $K_{Ca}3.1$ agonist is thiazolo[4,5-c]quinolin-2-amine, also known as SKA-56 (Formula (47)):

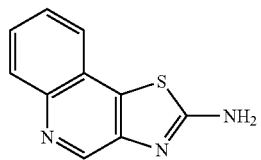

Formula (47)

or a pharmaceutically-acceptable salt, cocrystal, solvate, or prodrug thereof. The properties and synthesis of SKA-56 are described in Sankaranarayanan, et al., *Mol. Pharmacol.* 2009, 75, 281-95, the disclosure of which is incorporated by reference herein.

In an embodiment, the $K_{Ca}3.1$ agonist is 6,7-dihydro-[1,4]dioxino[2',3':4,5]benzo[1,2-d]thiazol-2-amine, also known as SKA-30 (Formula (48)):

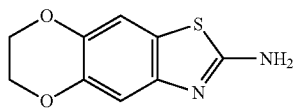

Formula (48)

or a pharmaceutically-acceptable salt, cocrystal, solvate, or prodrug thereof. The properties and synthesis of SKA-30 are described in Sankaranarayanan, et al., *Mol. Pharmacol.* 2009, 75, 281-95, the disclosure of which is incorporated by reference herein.

In an embodiment, the $K_{Ca}3.1$ agonist is a benzothiazole derivative selected from any one of the foregoing benzothiazole compounds, or a pharmaceutically-acceptable salt, cocrystal, solvate, or prodrug thereof. In an embodiment, the $K_{Ca}3.1$ agonist is a benzoimidazole derivative selected from any one of the foregoing benzoimidazole compounds, or a pharmaceutically-acceptable salt, cocrystal, solvate, or prodrug thereof.

In an embodiment, the $K_{Ca}3.1$ agonist is selected from the group consisting of:
5-ethylnaphtho[1,2-d]oxazol-2-amine;
5-propylnaphtho[1,2-d]oxazol-2-amine;
5-cyclopropylnaphtho[1,2-d]oxazol-2-amine;
5-(tert-butyl)naphtho[1,2-d]oxazol-2-amine;
5-fluoronaphtho[1,2-d]oxazol-2-amine;
5-chloronaphtho[1,2-d]oxazol-2-amine;
5-bromonaphtho[1,2-d]oxazol-2-amine;
5-iodonaphtho[1,2-d]oxazol-2-amine;
2-aminonaphtho[1,2-d]oxazole-5-carbonitrile;
naphtho[1,2-d]oxazol-2,5-diamine;
$N^5$-methylnaphtho[1,2-d]oxazole-2,5-diamine;
$N^5,N^5$-dimethylnaphtho[1,2-d]oxazole-2,5-diamine;
$N^5$-ethylnaphtho[1,2-d]oxazole-2,5-diamine;
5-(pyrrolidine-1-yl)naphtho[1,2-d]oxazol-2-amine;
5-methoxynaphtho[1,2-d]oxazol-2-amine;
5-trifluoromethylnaphtho[1,2-d]oxazol-2-amine;
and pharmaceutically-acceptable salts, cocrystals, solvates, or prodrugs thereof. The properties and synthesis of these compounds are described in International Patent Application Publication No. WO 2015/164816 A2, the disclosure of which is incorporated by reference herein.

In an embodiment, the $K_{Ca}3.1$ agonist is selected from the group consisting of:
5-ethylnaphtho[2,1-d]oxazol-2-amine;
5-propylnaphtho[2,1-d]oxazol-2-amine;
5-cyclopropylnaphtho[2,1-d]oxazol-2-amine;
5-(tert-butyl)naphtho[2,1-d]oxazol-2-amine;
5-fluoronaphtho[2,1-d]oxazol-2-amine;
5-chloronaphtho[2,1-d]oxazol-2-amine;
5-bromonaphtho[2,1-d]oxazol-2-amine;
5-iodonaphtho[2,1-d]oxazol-2-amine;
2-aminonaphtho[2,1-d]oxazole-5-carbonitrile;
naphtho[2,1-d]oxazol-2,5-diamine;
$N^5$-methylnaphtho[2,1-d]oxazole-2,5-diamine;
$N^5,N^5$-dimethylnaphtho[2,1-d]oxazole-2,5-diamine;
$N^5$-ethylnaphtho[2,1-d]oxazole-2,5-diamine;
5-(pyrrolidine-1-yl)naphtho[2,1-d]oxazol-2-amine;
5-methoxynaphtho[2,1-d]oxazol-2-amine;
5-trifluoromethylnaphtho[2,1-d]oxazol-2-amine;
and pharmaceutically-acceptable salts, cocrystals, solvates, or prodrugs thereof. The properties and synthesis of these compounds are described in International Patent Application Publication No. WO 2015/164816 A2, the disclosure of which is incorporated by reference herein.

In an embodiment, the $K_{Ca}3.1$ agonist is selected from the group consisting of:
2,3,3-trimethyl-3H-benzo[g]indole (also known as SKA-92 and CAS No. 74470-85-2);
2-methylnaphtho[2,3-d]oxazole (also known as SKA-104 and CAS No. 20686-66-2);
2-methylnaphtho[1,2-d]oxazole (also known as SKA-103 and CAS No. 85-15-4);
naphtho[1,2-d]oxazol-2-amine (also known as SKA-102 and CAS No. 858432-45-8);
2-methylnaphtho[1,2-d]thiazole (also known as SKA-74 and CAS No. 2682-45-3);
2-amino-4-(1-naphthyl)thiazole (also known as SKA-75, CAS No. 56503-96-9);
2-amino-4-(2-naphthyl)thiazole (also known as SKA-76, CAS No. 21331-43-1);

and pharmaceutically-acceptable salts, cocrystals, solvates, or prodrugs thereof. The properties and synthesis of these compounds are described in International Patent Application Publication No. WO 2015/164816 A2, the disclosure of which is incorporated by reference herein.

In an embodiment, the $K_{Ca}3.1$ agonist is 5-methylnaphtho[1,2-d]thiazol-2-amine (also known as SKA-111), and pharmaceutically-acceptable salts, cocrystals, solvates, or prodrugs thereof. The properties and synthesis of SKA-111 are described in International Patent Application Publication No. WO 2015/164816 A2 and Coleman, et al., *Mol. Pharmacol.* 2014, 86, 342-57, the disclosures of which are incorporated by reference herein.

Methods of Expanding Tumor Infiltrating Lymphocytes

In an embodiment, the invention provides a method of expanding TILs, the method comprising contacting a population of TILs comprising at least one TIL with a potassium channel agonist described herein. In an embodiment, the invention provides a method of expanding TILs, the method comprising the steps of contacting the population of TILs with one or more potassium channel agonists in a cell culture medium.

In an embodiment, the invention provides a process for the preparation of a population of tumor infiltrating lymphocytes (TILs) from a tumor, the process comprising the steps of:
 (a) contacting a fragmented tumor with a first cell culture medium;
 (b) performing an initial expansion (pre-REP) of the first population of TILs in the first cell culture medium to obtain a second population of TILs, wherein the second population of TILs is at least 5-fold greater in number than the first population of TILs, wherein the first cell culture medium comprises IL-2;
 (b) performing a rapid expansion (REP) of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
 (c) harvesting the third population of TILs; and
 wherein either the first cell culture medium or the second cell culture medium or both the first cell culture medium and the second cell culture medium further comprise a potassium channel agonist.

In an embodiment, the potassium channel agonist can differ in the pre-REP step and REP step.

In an embodiment, the potassium channel agonist is a $K_{Ca}3.1$ (IK channel) agonist.

In an embodiment, the invention provides a process for expanding a population of TILs including a pre-rapid expansion (pre-REP) process and a rapid expansion process (REP), wherein the cell culture medium used for expansion comprises IL-2 at a concentration selected from the group consisting of between 100 IU/mL and 10,000 IU/mL, between 200 IU/mL and 5,000 IU/mL, between 300 IU/mL and 4,800 IU/mL, between 400 IU/mL and 4,600 IU/mL, between 500 IU/mL and 4,400 IU/mL, between 600 IU/mL and 4,200 IU/mL, between 700 IU/mL and 4,000 IU/mL, between 800 IU/mL and 3,800 IU/mL, between 900 IU/mL and 3,600 IU/mL, between 1,000 IU/mL and 3,400 IU/mL, between 1,100 IU/mL and 3,200 IU/mL, between 1,200 IU/mL and 3,000 IU/mL, between 1,300 IU/mL and 2,800 IU/mL, between 1,400 IU/mL and 2,600 IU/mL, between 1,500 IU/mL and 2,400 IU/mL, between 1,600 IU/mL and 2,200 IU/mL, between 1,700 IU/mL and 2,000 IU/mL, between 5,500 IU/mL and 9,500 IU/mL, between 6,000 IU/mL and 9,000 IU/mL, between 6500 IU/mL and 8,500 IU/mL, between 7,000 IU/mL and 8,000 IU/mL, and between 7,500 IU/mL and 8,000 IU/mL.

In an embodiment, the invention provides a process for expanding a population of TILs including a pre-rapid expansion (pre-REP) process and a rapid expansion process (REP), wherein the cell culture medium used for expansion comprises IL-2 at a concentration selected from the group consisting of about 100 IU/mL, about 200 IU/mL, about 300 IU/mL, about 400 IU/mL, about 100 IU/mL, about 100 IU/mL, about 100 IU/mL, about 100 IU/mL, about 100 IU/mL, about 500 IU/mL, about 600 IU/mL, about 700 IU/mL, about 800 IU/mL, about 900 IU/mL, about 1,000 IU/mL, about 1,100 IU/mL, about 1,200 IU/mL, about 1,300 IU/mL, about 1,400 IU/mL, about 1,500 IU/mL, about 1,600 IU/mL, about 1,700 IU/mL, about 1,800 IU/mL, about 1,900 IU/mL, about 2,000 IU/mL, about 2,100 IU/mL, about 2,200 IU/mL, about 2,300 IU/mL, about 2,400 IU/mL, about 2,500 IU/mL, about 2,600 IU/mL, about 2,700 IU/mL, about 2,800 IU/mL, about 2,900 IU/mL, about 3,000 IU/mL, about 3,100 IU/mL, about 3,200 IU/mL, about 3,300 IU/mL, about 3,400 IU/mL, about 3,500 IU/mL, about 3,600 IU/mL, about 3,700 IU/mL, about 3,800 IU/mL, about 3,900 IU/mL, about 4,000 IU/mL, about 4,100 IU/mL, about 4,200 IU/mL, about 4,300 IU/mL, about 4,400 IU/mL, about 4,500 IU/mL, about 4,600 IU/mL, about 4,700 IU/mL, about 4,800 IU/mL, about 4,900 IU/mL, about 5,000 IU/mL, about 5,100 IU/mL, about 5,200 IU/mL, about 5,300 IU/mL, about 5,400 IU/mL, about 5,500 IU/mL, about 5,600 IU/mL, about 5,700 IU/mL, about 5,800 IU/mL, about 5,900 IU/mL, about 6,000 IU/mL, about 6,500 IU/mL, about 7,000 IU/mL, about 7,500 IU/mL, about 8,000 IU/mL, about 8,500 IU/mL, about 9,000 IU/mL, about 9,500 IU/mL, and about 10,000 IU/mL.

In an embodiment, the invention provides a process for expanding a population of TILs including a pre-rapid expansion (pre-REP) process. In an embodiment, the invention provides a pre-REP process of expanding a population of TILs, the pre-REP process comprising the steps of contacting the population of TILs with one or more potassium channel agonists in a cell culture medium, wherein the cell culture medium further comprises IL-2 at an initial concentration of between 1000 IU/mL and 6000 IU/mL.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of about 6000 IU/mL.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, and wherein the one or more potassium channel agonists comprises a $K_{Ca}3.1$ (IK channel) agonist.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, and wherein the one or more potassium channel agonists comprises a $K_{Ca}3.1$ (IK channel) agonist at a concentration selected from the group consisting of between 1 picomolar (pM) and 1000 pM, between 1 pM and 500 pM, between 50 pM and 450 pM, between 100 pM and 400 pM, between 150 pM and 350 pM, between 200 pM and 300 pM, between 550 pM and 950 pM, between 600 pM and 900 pM, between 650 pM and 850 pM, between 700 pM and 800 pM, between 1 nanomolar (nM) and 1000 nM, between 1 nM and 500 nM, between 50 nM and 450 nM, between 100 nM and 400 nM, between 150 nM and 350 nM, between 200 nM and 300 nM, between 550 nM and 950 nM, between 600 nM and 900 nM, between 650 nM and 850 nM, between 700 nM and 800 nM, between 100 nM and 500 nM, between 200 nM and 500 nM, between 300 nM and 500 nM, between 400 nM and 500 nM, between 500 nM and 600 nM, between 600 nM and 700 nM, between 700 nM and 800 nM, between 250 nM and 500 nM, between 10 nM and 200 nM, between 50 nM and 200 nM, between 1 micromolar (μM) and 1000 μM, between 1 μM and 500 μM, between 50 μM and 450 μM, between 100 μM and 400 μM, between 150 μM and 350 μM, between 200 μM and 300 μM, between 550 μM and 950 μM, between 600 μM and 900 μM, between 650 μM and 850 μM, between 700 μM and 800 μM, between 100 μM and 500 μM, between 200 μM and 500 μM, between 300 μM and 500 μM, between 400 μM and 500 μM, between 500 μM and 600 μM, between 600 μM and 700 μM, between 700 μM and 800 μM, between 250 μM and 500 μM, between 10 μM and 200 μM, between 50 μM and 200 μM, between 1 millimolar (mM) and 1000 mM, between 1 mM and 500 mM, between 50 mM and 450 mM, between 100 mM and 400 mM, between 150 mM and 350 mM, between 200 mM and 300 mM, between 550 mM and 950 mM, between 600 mM and 900 mM, between 650 mM and 850 mM, between 700 mM and 800 mM, between 100 mM and 500 mM, between 200 mM and 500 mM, between 300 mM and 500 mM, between 400 mM and 500 mM, between 500 mM and 600 mM, between 600 mM and 700 mM, between 700 mM and 800 mM, between 250 mM and 500 mM, between 10 mM and 200 mM, and between 50 mM and 200 mM.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, and wherein the one or more potassium channel agonists may include a $K_{Ca}3.1$ (IK channel) agonist, at a concentration selected from the group consisting of between 1 nanomolar (nM) and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, between 900 nM and 1 micromolar (μM), between 1 μM and 2 μM, between 2 μM and 5 μM, between 5 μM and 10 μM, and between 10 μM and 100 μM.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, and wherein the one or more potassium channel agonists comprises a $K_{Ca}3.1$ (IK channel) agonist at a concentration selected from the group consisting of about 1 pM, about 50 pM, about 100 pM, about 150 pM, about 200 pM, about 250 pM, about 300 pM, about 350 pM, about 400 pM, about 450 pM, about 500 pM, about 550 pM, about 600 pM, about 650 pM, about 700 pM, about 750 pM, about 800 pM, about 850 pM, about 900 pM, about 950 pM, about 1 nM, about 25 nM, about 50 nM, about 75 nM, about 100 nM, about 125 nM, about 150 nM, about 175 nM, about 200 nM, about 225 nM, about 250 nM, about 275 nM, about 300 nM, about 325 nM, about 350 nM, about 375 nM, about 400 nM, about 425 nM, about 450 nM, about 475 nM, about 500 nM, about 525 nM, about 550 nM, about 575 nM, about 600 nM, about 625 nM, about 650 nM, about 675 nM, about 700 nM, about 750 nM, about 800 nM, about 850 nM, about 900 nM, about 950 nM, about 1 μM, about 2 μM, about 5 μM, about 10 μM, about 20 μM, about 30 μM, about 40 μM, about 50 μM, about 60 μM, about 70 μM, about 80 μM, about 90 μM, about 100 μM, about 125 μM, about 150 μM, about 175 μM, about 200 μM, about 225 μM, about 250 μM, about 275 μM, about 300 μM, about 325 μM, about 350 μM, about 375 μM, about 400 μM, about 425 μM, about 450 μM, about 500 μM, about 550 μM, about 600 μM, about 650 μM, about 700 μM, about 750 μM, about 800 μM, about 850 μM, about 900 μM, about 950 μM, about 1 millimolar (mM), about 2 mM, about 5 mM, about 10 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, and about 100 mM.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, and wherein the one or more potassium channel agonists comprises a $K_{Ca}3.1$ (IK channel) agonist at a concentration selected from the group consisting of above 1 pM, above 50 pM, above 100 pM, above 150 pM, above 200 pM, above 250 pM, above 300 pM, above 350 pM, above 400 pM, above 450 pM, above 500 pM, above 550 pM, above 600 pM, above 650 pM, above 700 pM, above 750 pM, above 800 pM, above 850 pM, above 900 pM, above 950 pM, above 1 nM, above 25 nM, above 50 nM, above 75 nM, above 100 nM, above 125 nM, above 150 nM, above 175 nM, above 200 nM, above 225 nM, above 250 nM, above 275 nM, above 300 nM, above 325 nM, above 350 nM, above 375 nM, above 400 nM, above 425 nM, above 450 nM, above 475 nM, above 500 nM, above 525 nM, above 550 nM, above 575 nM, above 600 nM, above 625 nM, above 650 nM, above 675 nM, above 700 nM, above 750 nM, above 800 nM, above 850 nM, above 900 nM, above 950 nM, above 1 μM, above 2 μM, above 5 μM, above 10 μM, above 20 μM, above 30 μM, above 40 μM, above 50 μM, above 60 μM, above 70 μM, above 80 μM, above 90 μM, above 100 μM, above 125 μM, above 150 μM, above 175 μM, above 200 μM, above 225 μM, above 250 μM, above 275 μM, above 300 μM, above 325 μM, above 350 μM, above 375 μM, above 400 μM, above 425 μM, above 450 μM, above 500 μM, above 550 μM, above 600 μM, above 650 μM, above 700 μM, above 750 μM, above 800 μM, above 850 μM, above 900 μM, above 950 μM, above 1 millimolar (mM), above 2 mM, above 5 mM, above 10 mM, above 25 mM, above 30 mM, above 35 mM, above 40 mM, above 45 mM, above 50 mM, above 55 mM, above 60 mM, above 65 mM, above 70 mM, above 75 mM, above 80 mM, above 85 mM, above 90 mM, above 95 mM, and above 100 mM.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, and wherein the one or more potassium channel agonists comprises a $K_{Ca}3.1$ (IK channel) agonist at a concentration selected from the group consisting of below 1 pM, below 50 pM, below 100 pM, below 150 pM, below 200 pM, below 250 pM, below 300 pM, below 350 pM, below 400 pM, below 450 pM, below 500 pM, below 550 pM, below 600 pM, below 650 pM, below 700 pM, below 750 pM, below 800 pM, below 850 pM, below 900 pM, below 950 pM, below 1 nM, below 25 nM, below 50 nM, below 75 nM, below 100 nM, below 125 nM, below 150 nM, below 175 nM, below 200 nM, below 225 nM, below 250 nM, below 275 nM, below 300 nM, below 325 nM, below 350 nM, below 375 nM, below 400 nM, below 425 nM, below 450 nM, below 475 nM, below 500 nM, below 525 nM, below 550 nM, below 575 nM, below 600 nM, below 625 nM, below 650 nM, below 675 nM, below 700 nM, below 750 nM, below 800 nM, below 850 nM, below 900 nM, below 950 nM, below 1 µM, below 2 µM, below 5 µM, below 10 µM, below 20 µM, below 30 µM, below 40 µM, below 50 µM, below 60 µM, below 70 µM, below 80 µM, below 90 µM, below 100 µM, below 125 µM, below 150 µM, below 175 µM, below 200 µM, below 225 µM, below 250 µM, below 275 µM, below 300 µM, below 325 µM, below 350 µM, below 375 µM, below 400 µM, below 425 µM, below 450 µM, below 500 µM, below 550 µM, below 600 µM, below 650 µM, below 700 µM, below 750 µM, below 800 µM, below 850 µM, below 900 µM, below 950 µM, below 1 millimolar (mM), below 2 mM, below 5 mM, below 10 mM, below 25 mM, below 30 mM, below 35 mM, below 40 mM, below 45 mM, below 50 mM, below 55 mM, below 60 mM, below 65 mM, below 70 mM, below 75 mM, below 80 mM, below 85 mM, below 90 mM, below 95 mM, and below 100 mM.

In an embodiment, the invention provides a pre-REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, wherein the one or more potassium channel agonists comprises a $K_{Ca}3.1$ (IK channel) agonist, wherein the population of TILs comprising T cells with a phenotype selected from the group consisting CD8$^+$CD28$^+$, CD8$^+$CD27$^+$, CD8$^+$CD27$^+$CD28$^+$, CCR7$^+$, and combinations thereof, is increases relative to a reference population of TILs obtained without the potassium channel agonist, wherein the phenotype in the second population of TILs is increased by at least 1%, at least 2%, at least 3%, at least 4%, at least 5%, at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, at least 90%, at least 95%, at least 100%, at least 125%, at least 150%, at least 200%, at least 250%, at least 300%, at least 400%, or at least 500% relative to the reference population of TILs.

In an embodiment, the invention provides a pre-REP process of expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, wherein the one or more potassium channel agonists comprises a $K_{Ca}3.1$ (IK channel) agonist, wherein the population of TILs is expanded over a period of time selected from the group consisting of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, and 40 days.

In an embodiment, the invention provides a pre-REP process of expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL, wherein the one or more potassium channel agonists comprises a $K_{Ca}3.1$ (IK channel) agonist, wherein the population of TILs is expanded over a period of time selected from the group consisting of less than 1 day, less than 2 days, less than 3 days, less than 4 days, less than 5 days, less than 6 days, less than 7 days, less than 8 days, less than 9 days, less than 10 days, less than 11 days, less than 12 days, less than 13 days, less than 14 days, less than 15 days, less than 16 days, less than 17 days, less than 18 days, less than 19 days, less than 20 days, less than 21 days, less than 25 days, less than 30 days, less than 35 days, and less than 40 days.

In an embodiment, the invention provides a method of expanding a population of TILs, the method comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL.

In an embodiment, the invention provides a REP process for expanding a population of TILs, the process comprising the steps of contacting the population of TILs with one or more potassium channel agonists in a cell culture medium, wherein the cell culture medium further comprises IL-2 at an initial concentration of about 6000 IU/mL and OKT-3 antibody at an initial concentration of about 30 ng/mL.

In an embodiment, the invention provides a REP process for expanding a population of TILs, the process comprising the steps of contacting the population of TILs with one or more potassium channel agonists in a cell culture medium, wherein the cell culture medium further comprises IL-2 at an initial concentration of about 6000 IU/mL and OKT-3 antibody at an initial concentration of about 30 ng/mL, and wherein the one or more potassium channel agonists comprises a $K_{Ca}3.1$ (IK channel) agonist.

In an embodiment, the invention provides a REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL, and wherein the one or more potassium channel agonists comprises a $K_{Ca}3.1$ (IK channel) agonist at a concentration selected from the group consisting of between 1 picomolar (pM) and 1000 pM, between 1 pM and 500 pM, between 50 pM and 450 pM, between 100 pM and 400 pM, between 150 pM and 350 pM, between 200 pM and 300 pM, between 550 pM and 950 pM, between 600 pM and 900 pM, between 650 pM and 850 pM, between 700 pM and 800 pM, between 1 nanomolar (nM) and 1000 nM, between 1 nM and 500 nM, between 50 nM and 450 nM, between 100 nM and 400 nM, between 150 nM and 350 nM, between 200 nM and 300 nM, between 550 nM and 950 nM, between 600 nM and 900 nM, between 650 nM and 850 nM, between 700 nM and 800 nM, between 100 nM and 500 nM, between 200 nM and 500 nM, between 300 nM and 500 nM, between 400 nM and 500 nM, between 500 nM and 600 nM, between 600 nM and 700 nM, between 700 nM and 800 nM, between 250 nM and 500 nM, between 10 nM and 200 nM, between 50 nM and 200 nM, between 1 micromolar (µM) and 1000 µM, between 1 µM and 500 µM, between 50 µM and 450 µM, between 100 µM and 400 µM, between 150 µM and 350 µM, between 200 µM and 300 µM, between 550 µM and 950 µM, between 600 µM and 900 µM, between 650 µM and 850 µM, between 700 µM and 800 µM, between 100 µM and 500 µM, between 200 µM and 500 µM, between 300 µM and 500 µM, between 400 µM and 500 µM, between 500 µM and 600 µM, between 600 µM and 700 µM, between 700 µM and 800 µM, between 250 µM and 500 µM, between 10 µM and 200 µM, between 50 µM and 200 µM, between 1 millimolar (mM) and 1000 mM, between 1 mM and 500 mM, between 50 mM and 450 mM, between 100 mM and 400 mM, between 150 mM and 350 mM, between 200 mM and 300 mM, between 550 mM and 950 mM, between 600 mM and 900 mM, between 650 mM and 850 mM, between 700 mM and 800 mM, between 100 mM and 500 mM, between 200 mM and 500 mM, between 300 mM and 500 mM, between 400 mM and 500 mM, between 500 mM and 600 mM, between 600 mM and 700 mM, between 700 mM and 800 mM, between 250 mM and 500 mM, between 10 mM and 200 mM, and between 50 mM and 200 mM.

In an embodiment, the invention provides a REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL, and wherein the one or more potassium channel agonists comprises a $K_{Ca}3.1$ (IK channel) agonist at a concentration selected from the group consisting of between 1 nanomolar (nM) and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, between 900 nM and 1 micromolar (µM), between 1 µM and 2 between 2 µM and 5 between 5 µM and 10 between 10 µM and 100 between 100 µM and 200 between 200 µM and 300 between 300 µM and 400 between 400 µM and 500 between 500 µM and 600 between 600 µM and 700 between 700 µM and 800 µM, between 800 µM and 900 between 900 µM and 1 mM, between 1 mM and 10 mM, between 10 mM and 100 mM, between 100 mM and 200 mM, between 200 mM and 300 mM, between 300 mM and 400 mM, and between 400 mM and 500 mM.

In an embodiment, the invention provides a REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL, and wherein the one or more potassium channel agonists comprises a $K_{Ca}3.1$ (IK channel) agonist at a concentration selected from the group consisting of about 1 pM, about 50 pM, about 100 pM, about 150 pM, about 200 pM, about 250 pM, about 300 pM, about 350 pM, about 400 pM, about 450 pM, about 500 pM, about 550 pM, about 600 pM, about 650 pM, about 700 pM, about 750 pM, about 800 pM, about 850 pM, about 900 pM, about 950 pM, about 1 nM, about 25 nM, about 50 nM, about 75 nM, about 100 nM, about 125 nM, about 150 nM, about 175 nM, about 200 nM, about 225 nM, about 250 nM, about 275 nM, about 300 nM, about 325 nM, about 350 nM, about 375 nM, about 400 nM, about 425 nM, about 450 nM, about 475 nM, about 500 nM, about 525 nM, about 550 nM, about 575 nM, about 600 nM, about 625 nM, about 650 nM, about 675 nM, about 700 nM, about 750 nM, about 800 nM, about 850 nM, about 900 nM, about 950 nM, about 1 µM, about 2 µM, about 5 µM, about 10 µM, about 20 µM, about 30 µM, about 40 µM, about 50 µM, about 60 µM, about 70 µM, about 80 µM, about 90 µM, about 100 µM, about 125 µM, about 150 µM, about 175 µM, about 200 µM, about 225 µM, about 250 µM, about 275 µM, about 300 µM, about 325 µM, about 350 µM, about 375 µM, about 400 µM, about 425 µM, about 450 µM, about 500 µM, about 550 µM, about 600 µM, about 650 µM, about 700 µM, about 750 µM, about 800 µM, about 850 µM, about 900 µM, about 950 µM, about 1 millimolar (mM), about 2 mM, about 5 mM, about 10 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 125 mM, about 150 mM, about 175 mM, about 200 mM, about 300 mM, about 400 mM, and about 500 mM.

In an embodiment, the invention provides a REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL, and wherein the one or more potassium channel agonists comprises a $K_{Ca}3.1$ (IK channel) agonist at a concentration selected from the group consisting of above 1 pM, above 50 pM, above 100 pM, above 150 pM, above 200 pM, above 250 pM, above 300 pM, above 350 pM, above 400 pM, above 450 pM, above 500 pM, above 550 pM, above 600 pM, above 650 pM, above 700 pM, above 750 pM, above 800 pM, above 850 pM, above 900 pM, above 950 pM, above 1 nM, above 25 nM, above 50 nM, above 75 nM, above 100 nM, above 125 nM, above 150 nM, above 175 nM, above 200 nM, above 225 nM, above 250 nM, above 275 nM, above 300 nM, above 325 nM, above 350 nM, above 375 nM, above 400 nM, above 425 nM, above 450 nM, above 475 nM, above 500 nM, above 525 nM, above 550 nM, above 575 nM, above 600 nM, above 625 nM, above 650 nM, above 675 nM, above 700 nM, above 750 nM, above 800 nM, above 850 nM, above 900 nM, above 950 nM, above 1 µM, above 2 µM, above 5 µM, above 10 µM, above 20 µM, above 30 µM, above 40 µM, above 50 µM, above 60 µM, above 70 µM, above 80 µM, above 90 µM, above 100 µM, above 125 µM, above 150 µM, above 175 µM, above 200 µM, above 225 µM, above 250 µM, above 275 µM, above 300 µM, above 325 µM, above 350 µM, above 375 µM, above 400 µM, above 425 µM, above 450 µM, above 500 µM, above 550 µM, above 600 µM, above 650 µM, above 700 µM, above 750 µM, above 800 µM, above 850 µM, above 900 µM, above 950 µM, above 1 millimolar (mM), above 2 mM, above 5 mM, above 10 mM, above 25 mM, above 30 mM, above 35 mM, above 40 mM, above 45 mM, above 50 mM, above 55 mM, above 60 mM, above 65 mM, above 70 mM, above 75 mM, above 80 mM, above 85 mM, above 90 mM, above 95 mM, above 100 mM, above 125 mM, above 150 mM, above 175 mM, above 200 mM, above 300 mM, above 400 mM, and above 500 mM.

In an embodiment, the invention provides a REP process for expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL, and wherein the one or more potassium channel agonists comprises a $K_{Ca}3.1$ (IK channel) agonist at a concentration selected from the group consisting of below 1 pM, below 50 pM, below 100 pM, below 150 pM, below 200 pM, below 250 pM, below 300 pM, below 350 pM, below 400 pM, below 450 pM, below 500 pM, below 550 pM, below 600 pM, below 650 pM, below 700 pM, below 750 pM, below 800 pM, below 850 pM, below 900 pM, below 950 pM, below 1 nM, below 25 nM, below 50 nM, below 75 nM, below 100 nM, below 125 nM, below 150 nM, below 175 nM, below 200 nM, below 225 nM, below 250 nM, below 275 nM, below 300 nM, below 325 nM, below 350 nM, below 375 nM, below 400 nM, below 425 nM, below 450 nM, below 475 nM, below 500 nM, below 525 nM, below 550 nM, below 575 nM, below 600 nM, below 625 nM, below 650 nM, below 675 nM, below 700 nM, below 750 nM, below 800 nM, below 850 nM, below 900 nM, below 950 nM, below 1 μM, below 2 μM, below 5 μM, below 10 μM, below 20 μM, below 30 μM, below 40 μM, below 50 μM, below 60 μM, below 70 μM, below 80 μM, below 90 μM, below 100 μM, below 125 μM, below 150 μM, below 175 μM, below 200 μM, below 225 μM, below 250 μM, below 275 μM, below 300 μM, below 325 μM, below 350 μM, below 375 μM, below 400 μM, below 425 μM, below 450 μM, below 500 μM, below 550 μM, below 600 μM, below 650 μM, below 700 μM, below 750 μM, below 800 μM, below 850 μM, below 900 μM, below 950 μM, below 1 millimolar (mM), below 2 mM, below 5 mM, below 10 mM, below 25 mM, below 30 mM, below 35 mM, below 40 mM, below 45 mM, below 50 mM, below 55 mM, below 60 mM, below 65 mM, below 70 mM, below 75 mM, below 80 mM, below 85 mM, below 90 mM, below 95 mM, below 100 mM, below 125 mM, below 150 mM, below 175 mM, below 200 mM, below 300 mM, below 400 mM, and below 500 mM.

In an embodiment, the invention provides a REP process of expanding a population of tumor infiltrating lymphocytes (TILs), the process comprising the steps of contacting the population of TILs with one or more potassium channel agonists in a cell culture medium, wherein the population of TILs expands by at least 50-fold over a period of 7 days in the cell culture medium.

In an embodiment, the invention provides a REP process of expanding a population of tumor infiltrating lymphocytes (TILs), the process comprising the steps of contacting the population of TILs with one or more potassium channel agonists in a cell culture medium, wherein the population of TILs expands by at least 50-fold over a period of 7 days in the cell culture medium, and wherein the expansion is performed using a gas permeable container.

In an embodiment, the invention provides a REP process of expanding a population of tumor infiltrating lymphocytes (TILs), the process comprising the steps of contacting the population of TILs with one or more potassium channel agonists in a cell culture medium, wherein the population of TILs expands by at least 50-fold over a period of 7 days in the cell culture medium, and wherein the expansion is performed using a gas permeable container, wherein the gas permeable container is a gas permeable bag or a gas permeable flask.

In an embodiment, the invention provides a REP process of expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL, wherein the one or more potassium channel agonists comprises a $K_{Ca}3.1$ (IK channel) agonist, wherein the population of TILs is rapidly expanded over a period of time selected from the group consisting of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, and 40 days.

In an embodiment, the invention provides a REP process of expanding a population of TILs, the process comprising the steps of contacting the population of TILs with one or more potassium channel agonists in a cell culture medium, wherein the cell culture medium further comprises IL-2 at an initial concentration of between 1000 IU/mL and 6000 IU/mL and OKT-3 antibody at an initial concentration of about 30 ng/mL, wherein the one or more potassium channel agonists comprises a $K_{Ca}3.1$ (IK channel) agonist, wherein the population of TILs is rapidly expanded over a period of time selected from the group consisting of less than 1 day, less than 2 days, less than 3 days, less than 4 days, less than 5 days, less than 6 days, less than 7 days, less than 8 days, less than 9 days, less than 10 days, less than 11 days, less than 12 days, less than 13 days, less than 14 days, less than 15 days, less than 16 days, less than 17 days, less than 18 days, less than 19 days, less than 20 days, less than 21 days, less than 25 days, less than 30 days, less than 35 days, and less than 40 days.

In an embodiment, REP can be performed in a gas permeable container using the potassium channel agonists of the present disclosure by any suitable method. For example, TILs can be rapidly expanded using non-specific T cell receptor stimulation in the presence of interleukin-2 (IL-2) or interleukin-15 (IL-15). The non-specific T cell receptor stimulus can include, for example, about 30 ng/mL of OKT-3, a monoclonal anti-CD3 antibody (commercially available from Ortho-McNeil, Raritan, N.J. or Miltenyi Biotech, Auburn, Calif.). TILs can be rapidly expanded by further stimulation of the TILs in vitro with one or more antigens, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gp100:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2.

In an embodiment, a method for expanding TILs may include using about 5000 mL to about 25000 mL of cell culture medium, about 5000 mL to about 10000 mL of cell culture medium, or about 5800 mL to about 8700 mL of cell culture medium. In an embodiment, a method for expanding TILs may include using about 1000 mL to about 2000 mL of cell medium, about 2000 mL to about 3000 mL of cell culture medium, about 3000 mL to about 4000 mL of cell culture medium, about 4000 mL to about 5000 mL of cell culture medium, about 5000 mL to about 6000 mL of cell culture medium, about 6000 mL to about 7000 mL of cell culture medium, about 7000 mL to about 8000 mL of cell culture medium, about 8000 mL to about 9000 mL of cell culture medium, about 9000 mL to about 10000 mL of cell culture medium, about 10000 mL to about 15000 mL of cell culture medium, about 15000 mL to about 20000 mL of cell culture medium, or about 20000 mL to about 25000 mL of cell culture medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad Calif.). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the rapid expansion is performed using a gas permeable container. Such embodiments allow for cell populations to expand from about $5 \times 10^5$ cells/cm$^2$ to between $10 \times 10^6$ and $30 \times 10^6$ cells/cm$^2$. In an embodiment, this expansion occurs without feeding. In an embodiment, this expansion occurs without feeding so long as medium resides at a height of about 10 cm in a gas-permeable flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739 A1, International Patent Application Publication No. WO 2014/210036 A1, U.S. Patent Application Publication No. US 2013/0115617 A1, International Publication No. WO 2013/188427 A1, U.S. Patent Application Publication No. US 2011/0136228 A1, U.S. Pat. No. 8,809,050, International Patent Application Publication No. WO 2011/072088 A2, U.S. Patent Application Publication No. US 2016/0208216 A1, U.S. Patent Application Publication No. US 2012/0244133 A1, International Patent Application Publication No. WO 2012/129201 A1, U.S. Patent Application Publication No. US 2013/0102075 A1, U.S. Pat. No. 8,956,860, International Patent Application Publication No. WO 2013/173835 A1, and U.S. Patent Application Publication No. US 2015/0175966 A1, the disclosures of which are incorporated herein by reference. Such processes are also described in Jin, et al., *J. Immunotherapy* 2012, 35, 283-292, the disclosure of which is incorporated by reference herein.

In an embodiment, the gas permeable container is a G-Rex 10 flask (Wilson Wolf Manufacturing Corporation, New Brighton, Minn., USA). In an embodiment, the gas permeable container includes a 10 cm$^2$ gas permeable culture surface. In an embodiment, the gas permeable container includes a 40 mL cell culture medium capacity. In an embodiment, the gas permeable container provides 100 to 300 million TILs after 2 medium exchanges.

In an embodiment, the gas permeable container is a G-Rex 100 flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 450 mL cell culture medium capacity. In an embodiment, the gas permeable container provides 1 to 3 billion TILs after 2 medium exchanges.

In an embodiment, the gas permeable container is a G-Rex 100M flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 1000 mL cell culture medium capacity. In an embodiment, the gas permeable container provides 1 to 3 billion TILs without medium exchange.

In an embodiment, the gas permeable container is a G-Rex 100 L flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 2000 mL cell culture medium capacity. In an embodiment, the gas permeable container provides 1 to 3 billion TILs without medium exchange.

In an embodiment, the gas permeable container is a G-Rex 24 well plate (Wilson Wolf Manufacturing Corporation, New Brighton, Minn., USA). In an embodiment, the gas permeable container includes a plate with wells, wherein each well includes a 2 cm$^2$ gas permeable culture surface. In an embodiment, the gas permeable container includes a plate with wells, wherein each well includes an 8 mL cell culture medium capacity. In an embodiment, the gas permeable container provides 20 to 60 million cells per well after 2 medium exchanges.

In an embodiment, the gas permeable container is a G-Rex 6 well plate (Wilson Wolf Manufacturing Corporation, New Brighton, Minn., USA). In an embodiment, the gas permeable container includes a plate with wells, wherein each well includes a 10 cm$^2$ gas permeable culture surface. In an embodiment, the gas permeable container includes a plate with wells, wherein each well includes a 40 mL cell culture medium capacity. In an embodiment, the gas permeable container provides 100 to 300 million cells per well after 2 medium exchanges.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using potassium channel agonists for a duration of about 14 to about 42 days, e.g., about 28 days.

In an embodiment, the ratio of TILs to potassium channel agonists (cells to moles) in the rapid expansion is about 1 to 0.00000001, about 1 to 0.0000001, about 1 to 0.000001, about 1 to 0.00001, about 1 to 0.0001, about 1 to 0.001, about 1 to 0.01, about 1 to 0.01, about 1 to 0.1, or about 1 to 1. In an embodiment, the ratio of TILs to moles of potassium channel agonists in the rapid expansion is between 1 to 0.00000001 and 1 to 0.0001. In an embodiment, the ratio of TILs to potassium channel agonists in the rapid expansion is between 1 to 0.00000001 and 1 to 0.000001.

In an embodiment, the ratio of TILs to potassium channel agonists (TIL:potassium channel agonist, cells to molecules) is selected from the group consisting of about 1:1 to about 1:10, about 1:10 to about 1:100, about 1:100 to about 1:1000, about 1:1000 to about $1:10^4$, about $1:10^4$ to about $1:10^5$, about $1:10^5$ to about $1:10^6$, about $1:10^6$ to about $1:10^7$, about $1:10^7$ to about $1:10^8$, and about $1:10^8$ to about $1:10^9$.

In an embodiment, the cell culture medium comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In a preferred embodiment, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody.

In an embodiment, TILs are expanded in gas-permeable containers. Gas-permeable containers have been used to expand TILs using PBMCs using methods, compositions, and devices known in the art, including those described in U.S. patent application Publication No. U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, about 10 L, about 11 L, about 12 L, about 13 L, about 14 L, about 15 L, about 16 L, about 17 L, about 18 L, about 19 L, about 20 L, about 25 L, and about 30 L. In an embodiment, the cell expansion system includes a gas permeable cell bag with a volume range selected from the group consisting of between 50 and 150 mL, between 150 and 250 mL, between 250 and 350 mL, between 350 and 450 mL, between 450 and 550 mL, between 550 and 650 mL, between 650 and 750 mL, between 750 and 850 mL, between 850 and 950 mL, and between 950 and 1050 mL. In an embodiment, the cell expansion system includes a gas permeable cell bag with a volume range selected from the group consisting of between 1 L and 2 L, between 2 L and 3 L, between 3 L and 4 L, between 4 L and 5 L, between 5 L and 6 L, between 6 L and 7 L, between 7 L and 8 L, between 8 L and 9 L, between 9 L and 10 L, between 10 L and 11 L, between 11 L and 12 L, between 12 L and 13 L, between 13 L and 14 L, between 14 L and 15 L, between 15 L and 16 L, between 16 L and 17 L, between 17 L and 18 L, between 18 L and 19 L, and between 19 L and 20 L. In an embodiment, the cell expansion system includes a gas permeable cell bag with a volume range selected from the group consisting of between 0.5 L and 5 L, between 5 L and 10 L, between 10 L and 15 L, between 15 L and 20 L, between 20 L and 25 L, and between 25 L and 30 L. In an embodiment, the cell expansion system utilizes a rocking time of about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, and about 28 days. In an embodiment, the cell expansion system utilizes a rocking time of between 30 minutes and 1 hour, between 1 hour and 12 hours, between 12 hours and 1 day, between 1 day and 7 days, between 7 days and 14 days, between 14 days and 21 days, and between 21 days and 28 days. In an embodiment, the cell expansion system utilizes a rocking rate of about 2 rocks/minute, about 5 rocks/minute, about 10 rocks/minute, about 20 rocks/minute, about 30 rocks/minute, and about 40 rocks/minute. In an embodiment, the cell expansion system utilizes a rocking rate of between 2 rocks/minute and 5 rocks/minute, 5 rocks/minute and 10 rocks/minute, 10 rocks/minute and 20 rocks/minute, 20 rocks/minute and 30 rocks/minute, and 30 rocks/minute and 40 rocks/minute. In an embodiment, the cell expansion system utilizes a rocking angle of about 2°, about 3°, about 4°, about 5°, about 6°, about 7°, about 8°, about 9°, about 10°, about 11°, and about 12°. In an embodiment, the cell expansion system utilizes a rocking angle of between 2° and 3°, between 3° and 4°, between 4° and 5°, between 5° and 6°, between 6° and 7°, between 7° and 8°, between 8° and 9°, between 9° and 10°, between 10° and 11°, and between 11° and 12°.

In an embodiment, a method of expanding TILs using potassium channel agonists further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

In an embodiment, the invention provides a method of expanding a population of TILs using any of the potassium channel agonists of the present disclosure, the method comprising the steps as described in Jin, et al., *J. Immunotherapy* 2012, 35, 283-292, the disclosure of which is incorporated by reference herein. For example, the tumor or portion thereof may be placed in enzyme media and mechanically dissociated for approximately 1 minute. The mixture may then be incubated for 30 minutes at 37° C. in 5% $CO_2$ and then mechanically disrupted again for approximately 1 minute. After incubation for 30 minutes at 37° C. in 5% $CO_2$, the tumor or portion thereof may be mechanically disrupted a third time for approximately 1 minute. If after the third mechanical disruption, large pieces of tissue are present, 1 or 2 additional mechanical dissociations may be applied to the sample, with or without 30 additional minutes of incubation at 37° C. in 5% $CO_2$. At the end of the final incubation, if the cell suspension contains a large number of red blood cells or dead cells, a density gradient separation using Ficoll may be performed to remove these cells. TIL cultures were initiated in 24-well plates (Costar 24-well cell culture cluster, flat bottom; Corning Incorporated, Corning, N.Y.), each well may be seeded with $1 \times 10^6$ tumor digest cells or one tumor fragment approximately 1 to 8 $mm^3$ in size in 2 mL of complete medium (CM) with IL-2 (6000 IU/mL; Chiron Corp., Emeryville, Calif.). CM comprises Roswell Park Memorial Institute (RPMI) 1640 buffer with GlutaMAX, supplemented with 10% human AB serum, 25 mM Hepes, and 10 mg/mL gentamicin. Cultures may be initiated in gas-permeable flasks with a 40 mL capacity and a 10 $cm^2$ gas-permeable silicon bottom (G-Rex 10; Wilson Wolf Manufacturing, New Brighton, each flask may be loaded with $10-40 \times 10^6$ viable tumor digest cells or 5-30 tumor fragments in 10-40 mL of CM with IL-2. G-Rex 10 and 24-well plates may be incubated in a humidified incubator at 37° C. in 5% $CO_2$ and 5 days after culture initiation, half the media may be removed and replaced with fresh CM and IL-2 and after day 5, half the media may be changed every 2-3 days. Rapid expansion protocol (REP) of TILs may be performed using T-175 flasks and gas-permeable bags or gas-permeable G-Rex flasks, as described elsewhere herein, using the potassium channel agonists of the present disclosure. For REP in T-175 flasks, $1 \times 10^6$ TILs may be suspended in 150 mL of media in each flask. The TIL may be cultured with potassium channel agonists of the present disclosure at a ratio described herein, in a 1 to 1 mixture of CM and AIM-V medium (50/50 medium), supplemented with 3000 IU/mL of IL-2 and 30 ng/mL of anti-CD3 antibody (OKT-3). The T-175 flasks may be incubated at 37° C. in 5% $CO_2$. Half the media may be changed on day 5 using 50/50 medium with 3000 IU/mL of IL-2. On day 7, cells from 2 T-175 flasks may be combined in a 3 L bag and 300 mL of AIM-V with 5% human AB serum and 3000 IU/mL of IL-2 may be added to the 300 mL of TIL suspension. The number of cells in each bag may be counted every day or two days, and fresh media may be added to keep the cell count between 0.5 and $2.0 \times 10^6$ cells/mL. For REP in 500 mL capacity flasks with 100 $cm^2$ gas-permeable silicon bottoms (e.g., G-Rex 100, Wilson Wolf Manufacturing, as described elsewhere herein), $5 \times 10^6$ or $10 \times 10^6$ TILs may be cultured with potassium channel agonists at a ratio described herein (e.g., 1 to 100) in 400 mL of 50/50 medium, supplemented with 3000 IU/mL of IL-2 and 30 ng/mL of anti-CD3 antibody (OKT-3). The G-Rex100 flasks may be incubated at 37° C. in 5% $CO_2$. On day five, 250 mL of supernatant may be removed and placed into centrifuge bottles and centrifuged at 1500 rpm (491 g) for 10 minutes. The obtained TIL pellets may be resuspended with 150 mL of fresh 50/50 medium with 3000 IU/mL of IL-2 and added back to the G-Rex 100 flasks. When TIL are expanded serially in G-Rex 100 flasks, on day seven the TIL in each G-Rex100 are suspended in the 300 mL of media present in each flask and the cell suspension may be divided into three 100 mL aliquots that may be used to seed 3 G-Rex100 flasks. About 150 mL of AIM-V with 5% human AB serum and 3000 IU/mL of IL-2 may then be added to each flask. G-Rex 100 flasks may then be incubated at 37° C. in 5% $CO_2$, and after four days, 150 mL of AIM-V with 3000 IU/mL of IL-2 may be added to each G-Rex 100 flask. After this, the REP may be completed by harvesting cells on day 14 of culture.

In an embodiment, a method of expanding or treating a cancer includes a step wherein TILs are obtained from a patient tumor sample. A patient tumor sample may be obtained using methods known in the art. For example, TILs may be cultured from enzymatic tumor digests and tumor fragments (about 1 to about 8 $mm^3$ in size) from sharp dissection. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In an embodiment, a rapid expansion process for TILs may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks, commercially available from Wilson Wolf Manufacturing Corporation, New Brighton, Minn., USA). For TIL rapid expansion in T-175 flasks, $1 \times 10^6$ TILs suspended in 150 mL of media may be added to each T-175 flask. The TILs may be cultured with potassium channel agonists at a ratio of 1 TIL to 100 potassium channel agonist molecules and the cells were cultured in a 1 to 1 mixture of CM and AIM-V medium, supplemented with 3000 IU (international units) per mL of IL-2 and 30 ng per ml of anti-CD3 antibody (e.g., OKT-3). The T-175 flasks may be incubated at 37° C. in 5% $CO_2$. Half the media may be exchanged on day 5 using 50/50 medium with 3000 IU per mL of IL-2. On day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, for TIL rapid expansions in 500 mL capacity gas permeable flasks with $100^2$ cm gas-permeable silicon bottoms (G-Rex 100, commercially available from Wilson Wolf Manufacturing Corporation, New Brighton, Minn., USA), $5 \times 10^6$ or $10 \times 10^6$ TIL may be cultured with potassium channel agonists in 400 mL of 50/50 medium, supplemented with 5% human AB serum, 3000 IU per mL of IL-2 and 30 ng per mL of anti-CD3 (OKT-3). The G-Rex 100 flasks may be incubated at 37° C. in 5% $CO_2$. On day 5, 250 mL of supernatant may be removed and placed into centrifuge bottles and centrifuged at 1500 rpm (revolutions per minute; 491×g) for 10 minutes. The TIL pellets may be re-suspended with 150 mL of fresh medium with 5% human AB serum, 3000 IU per mL of IL-2, and added back to the original G-Rex 100 flasks. When TILs are expanded serially in G-Rex 100 flasks, on day 7 the TILs in each G-Rex 100 flask may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-Rex 100 flask. The cells may be harvested on day 14 of culture.

In an embodiment, TILs may be prepared as follows. 2 $mm^3$ tumor fragments are cultured in complete media (CM) comprised of AIM-V medium (Invitrogen Life Technologies, Carlsbad, Calif.) supplemented with 2 mM glutamine (Mediatech, Inc. Manassas, Va.), 100 U/mL penicillin (Invitrogen Life Technologies), 100 µg/mL streptomycin (Invitrogen Life Technologies), 5% heat-inactivated human AB serum (Valley Biomedical, Inc. Winchester, Va.) and 600 IU/mL rhIL-2 (Chiron, Emeryville, Calif.). For enzymatic digestion of solid tumors, tumor specimens are diced into RPMI-1640, washed and centrifuged at 800 rpm for 5 minutes at 15-22° C., and resuspended in enzymatic digestion buffer (0.2 mg/mL Collagenase and 30 units/ml of DNase in RPMI-1640) followed by overnight rotation at room temperature. TILs established from fragments may be grown for 3-4 weeks in CM and expanded fresh or cryopreserved in heat-inactivated HAB serum with 10% dimethylsulfoxide (DMSO) and stored at −180° C. until the time of study. Tumor associated lymphocytes (TAL) obtained from ascites collections were seeded at $3\times10^6$ cells/well of a 24 well plate in CM. TIL growth was inspected about every other day using a low-power inverted microscope.

In an embodiment, the potassium channel agonists of the present invention may be used to expand T cells. Any of the foregoing embodiments of the present invention described for the expansion of TILs may also be applied to the expansion of T cells. In an embodiment, the potassium channel agonists of the present invention may be used to expand $CD8^+$ T cells. In an embodiment, the potassium channel agonists of the present invention may be used to expand $CD4^+$ T cells. In an embodiment, the potassium channel agonists of the present invention may be used to expand T cells transduced with a chimeric antigen receptor (CAR-T). In an embodiment, the potassium channel agonists of the present invention may be used to expand T cells comprising a modified T cell receptor (TCR). The CAR-T cells may be targeted against any suitable antigen, including CD19, as described in the art, e.g., in U.S. Pat. Nos. 7,070,995; 7,446,190; 8,399,645; 8,916,381; and 9,328,156; the disclosures of which are incorporated by reference herein. The modified TCR cells may be targeted against any suitable antigen, including NY-ESO-1, TRP-1, TRP-2, tyrosinase cancer antigen, MAGE-A3, SSX-2, and VEGFR2, or antigenic portions thereof, as described in the art, e.g., in U.S. Pat. Nos. 8,367,804 and 7,569,664, the disclosures of which are incorporated by reference herein.

Optional Cryopreservation of TILs

In some embodiments, either a bulk TIL population or an expanded population of TILs can be optionally cryopreserved. In some embodiments, cryopreservation occurs on a therapeutic TIL population. In some embodiments, cryopreservation occurs on the TILs harvested after an expansion. In some embodiments, the TILs are cryopreserved in an infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As described herein, cryopreservation can occur at numerous points throughout the TIL expansion process. In some embodiments, the bulk TIL population after a first expansion or an expanded population of TILs after one or more second expansions can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In some cases, a TIL population can be cryopreserved immediately, using the protocols described herein.

Pharmaceutical Compositions, Dosages, and Dosing Regimens for TILs

In an embodiment, TILs expanded using methods of the present disclosure are administered to a patient as a pharmaceutical composition. In an embodiment, the pharmaceutical composition is a suspension of TILs in a sterile buffer. TILs expanded using methods of the present disclosure may be administered by any suitable route as known in the art. Preferably, the TILs are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. Preferably, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^8$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25% 4%, 3.75%, 3.50%, 3.25% 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10_9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{11}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation or direct injection into tumor, or by inhalation.

Pharmaceutical Compositions, Dosages, and Dosing Regimens for Potassium Channel Agonists In some embodiments, the invention provides a pharmaceutical composition comprising a potassium channel agonist, including a $K_{Ca}3.1$ agonist, for use in the treatment of the diseases and conditions described herein in combination with treatment using TILs of the present invention. In a preferred embodiment, the invention provides pharmaceutical compositions, including those described below, for use in the treatment of cancer.

In some embodiments, a potassium channel agonist formulation comprises one or more excipients selected from tris-hydrochloride, sodium chloride, mannitol, pentetic acid, polysorbate 80, sodium hydroxide, and hydrochloric acid.

In some embodiments, the pharmaceutical composition comprising a potassium channel agonist may be a liquid pharmaceutical composition suitable for oral consumption.

Pharmaceutical compositions of the invention suitable for oral administration can be presented as discrete dosage forms, such as capsules, sachets, tablets, liquids, or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

In an embodiment, a potassium channel agonist, including a $K_{Ca}3.1$ agonist, is administered to a subject orally or by infusing a dose selected from the group consisting of about 0.25 mg, about 0.5 mg, about 1 mg, about 2 mg, about 2.5 mg, about 5 mg, about 7.5 mg, about 8 mg, about 10 mg, about 20 mg, about 25 mg, about 50 mg, about 75 mg, 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, and about 2000 mg. In an embodiment, a potassium channel agonist, including a $K_{Ca}3.1$ agonist, is administered weekly. In an embodiment, a potassium channel agonist, including a $K_{Ca}3.1$ agonist, is administered every two weeks. In an embodiment, a potassium channel agonist, including a $K_{Ca}3.1$ agonist, is administered every three weeks. In an embodiment, a potassium channel agonist is administered monthly. In an embodiment, a potassium channel agonist, including a $K_{Ca}3.1$ agonist, is administered at a lower initial dose, which is escalated when administered at subsequent intervals administered monthly.

The amounts of potassium channel agonists, including $K_{Ca}3.1$ agonists, administered will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the potassium channel agonist(s) may be provided in units of mg/kg of body mass or in mg/m² of body surface area.

In some embodiments, the potassium channel agonists, including $K_{Ca}3.1$ agonists, are administered for more than 1, 2, 3, 4, 5, 6, 7, 14, 28 days, 2 months, 3 months, 6 months, 12 months, or 24 months. In some cases, continuous dosing is achieved and maintained as long as necessary.

In some embodiments, an effective dosage of a potassium channel agonist disclosed herein, including a $K_{Ca}3.1$ agonist, is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a potassium channel agonist disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of a potassium channel agonist disclosed herein, including a $K_{Ca}3.1$ agonist, is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a potassium channel agonist disclosed herein is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, an effective dosage of a potassium channel agonist disclosed herein, including a $K_{Ca}3.1$ agonist, is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg. In some embodiments, an effective dosage of a potassium channel agonist disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of a potassium channel agonist disclosed herein, including a $K_{Ca}3.1$ agonist, is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.01 mg/kg to about 0.7 mg/kg, about 0.07 mg/kg to about 0.65 mg/kg, about 0.15 mg/kg to about 0.6 mg/kg, about 0.2 mg/kg to about 0.5 mg/kg, about 0.3 mg/kg to about 0.45 mg/kg, about 0.3 mg/kg to about 0.4 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg to about 1.6 mg/kg, about 1.35 mg/kg to about 1.5 mg/kg, about 1.4 mg/kg to about 1.45 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, a potassium channel agonist disclosed herein is about 0.4 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a potassium channel agonist, including a $K_{Ca}3.1$ agonist, is administered at a dosage of 1 to 1000 mg BID, including 1 mg, 2 mg, 5 mg, 10 mg, 20 mg, 30 mg, 40 mg, 50 mg, 60 mg, 70 mg, 80 mg, 90 mg, 100 mg, 150 mg, or 200 mg BID.

In some embodiments, the concentration of the potassium channel agonists, including $K_{Ca}3.1$ agonists, and combinations thereof provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the potassium channel agonists, including $K_{Ca}3.1$ agonists, and combinations thereof provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the potassium channel agonists, including $K_{Ca}3.1$ agonists, in the pharmaceutical compositions is independently in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the potassium channel agonists, including $K_{Ca}3.1$ agonists, in the pharmaceutical compositions is independently in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the potassium channel agonists, including $K_{Ca}3.1$ agonists, in the pharmaceutical compositions is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the potassium channel agonists, including $K_{Ca}3.1$ agonists, in the pharmaceutical compositions is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the invention provides a pharmaceutical composition comprising a potassium channel agonist, including a $K_{Ca}3.1$ agonist, for use in the treatment of the diseases and conditions described herein in combination with treatment using TILs of the present invention, wherein the potassium channel agonist is administered twice daily at a dosage of 50 mg following treatment with TILs, wherein the pharmaceutical composition further comprises anhydrous dibasic calcium phosphate, colloidal silicon dioxide, croscarmellose sodium, hypromellose, magnesium stearate, microcrystalline cellulose, polyethylene glycol, titanium dioxide, or combinations thereof. In some of the foregoing embodiments, the potassium channel agonist or $K_{Ca}3.1$ agonist is riluzole.

Pharmaceutical Compositions for Combinations of TILs and Potassium Channel Agonists In preferred embodiments, the invention provides a pharmaceutical composition for injection containing the combination of a TIL and at least one potassium channel agonist, and combinations thereof, and a pharmaceutical excipient suitable for injection, including intratumoral injection or intravenous infusion. Components and amounts of agents in the compositions are as described herein.

In some embodiments, the combination of TILs and a potassium channel agonist is administered in a single dose. Such administration may be by injection, e.g., intravenous injection, in order to introduce the potassium channel agonist.

In some embodiments, the combination of TILs and potassium channel agonists is administered in multiple doses. In a preferred embodiment, the combination of TILs and potassium channel agonists is administered in multiple doses. Dosing of the potassium channel agonists may be once, twice, three times, four times, five times, six times, or more than six times per day. Dosing of TILs and potassium channel agonists may be once a month, once every two weeks, once a week, or once every other day.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating the combination of the potassium channel agonists and TILs in the required amounts in the appropriate media with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., *Handbook of Clinical Drug Data*, Tenth Edition, McGraw-Hill, 2002; and Pratt and Taylor, eds., *Principles of Drug Action*, Third Edition, Churchill Livingston, N.Y., 1990, each of which is incorporated by reference herein in its entirety.

Administration of a combination of a TIL and a potassium channel agonist can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

The invention also provides kits. The kits include a combination of ready-to-administer TILs and a potassium channel agonist, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, the potassium channel agonists and TILs and another active pharmaceutical ingredient are provided as separate compositions in separate containers within the kit. In selected embodiments, the molecule selected from the group consisting of a potassium channel agonist and the TILs are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

The kits described above are preferably for use in the treatment of the diseases and conditions described herein. In a preferred embodiment, the kits are for use in the treatment of cancer. In preferred embodiments, the kits are for use in treating solid tumor cancers. In a preferred embodiment, the kits of the present invention are for use in the treatment of cancer, including any of the cancers described herein.

Methods of Treating Cancers

The compositions and combinations of TILs (and populations thereof) and potassium channel agonists described above can be used in a method for treating hyperproliferative disorders. In a preferred embodiment, they are for use in treating cancers. In a preferred embodiment, the invention provides a method of treating a cancer, wherein the cancer is a hematological malignancy or a solid tumor. In a preferred embodiment, the invention provides a method of treating a cancer, wherein the cancer is selected from the group consisting of melanoma, ovarian cancer, cervical cancer, lung cancer, bladder cancer, breast cancer, head and neck cancer, renal cell carcinoma, acute myeloid leukemia, colorectal cancer, and sarcoma. In a preferred embodiment, the invention provides a method of treating a cancer, wherein the cancer is selected from the group consisting of non-small cell lung cancer (NSCLC) or triple negative breast cancer, double-refractory melanoma, and uveal (ocular) melanoma. In a preferred embodiment, the invention provides a method of treating a cancer, wherein the cancer is selected from the group consisting of melanoma, ovarian cancer, cervical cancer, lung cancer, bladder cancer, breast cancer, head and neck cancer, renal cell carcinoma, acute myeloid leukemia, colorectal cancer, and sarcoma with a combination of TILs and a potassium channel agonist. In a preferred embodiment, the invention provides a method of treating a cancer, wherein the cancer is selected from the group consisting of non-small cell lung cancer (NSCLC), estrogen receptor positive (ER$^+$) breast cancer, progesterone receptor positive (PR$^+$) breast cancer, human epidermal growth factor receptor 2 (HER2$^+$) breast cancer, triple positive breast cancer (ER$^+$/PR$^+$/HER2$^+$), triple negative breast cancer (ER$^-$/PR$^-$/HER2$^-$), double-refractory melanoma, and uveal (ocular) melanoma with a combination of TILs and a potassium channel agonist.

In some embodiments, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor to obtain tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
  wherein either the first cell culture medium or the second cell culture medium or both the first cell culture medium and the second cell culture medium further comprise a potassium channel agonist;
  wherein the cancer is selected from the group consisting of melanoma, ovarian cancer, cervical cancer, lung cancer, bladder cancer, breast cancer, head and neck cancer, renal cell carcinoma, acute myeloid leukemia, colorectal cancer, and sarcoma.

In some embodiments, the invention provides a method of treating a cancer with a population of tumor infiltrating lymphocytes (TILs) comprising the steps of:
  (a) resecting a tumor from a patient, the tumor comprising a first population of TILs;
  (b) fragmenting the tumor to obtain tumor fragments;
  (c) contacting the tumor fragments with a first cell culture medium;
  (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
  (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
  (f) harvesting the third population of TILs; and
  (g) administering a therapeutically effective portion of the third population of TILs to a patient with the cancer;
  wherein either the first cell culture medium or the second cell culture medium or both the first cell culture medium and the second cell culture medium further comprise a potassium channel agonist;
  wherein the cancer is selected from the group consisting of non-small cell lung cancer (NSCLC), estrogen receptor positive (ER$^+$) breast cancer, progesterone receptor positive WO breast cancer, human epidermal growth factor receptor 2 (HER2$^+$) breast cancer, triple positive breast cancer (ER$^+$/PR$^+$/HER2$^+$), triple negative breast cancer (ER$^-$/PR$^-$/HER2$^-$), double-refractory melanoma, and uveal (ocular) melanoma.

Efficacy of the methods, compounds, and combinations of compounds described herein in treating, preventing and/or managing the indicated diseases or disorders can be tested using various animal models known in the art. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32. Models for determining efficacy of treatments for colorectal cancer, including the CT26 model, are described in Castle, et al., *BMC Genomics,* 2013, 15, 190; Endo, et al., *Cancer Gene Therapy,* 2002, 9, 142-148; Roth, et al., *Adv. Immunol.* 1994, 57, 281-351; Fearon, et al., *Cancer Res.* 1988, 48, 2975-2980.

Non-Myeloablative Lymphodepletion with Chemotherapy

In an embodiment, the invention provides a method of treating a cancer with a population of TILs, wherein a patient is pre-treated with non-myeloablative chemotherapy prior to an infusion of TILs and treatment with a potassium channel agonist according to the present disclosure. In an embodiment, the non-myeloablative chemotherapy is one or more chemotherapeutic agents. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.*, 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 µg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m²/day, 150 mg/m²/day, 175 mg/m²/day 200 mg/m²/day, 225 mg/m²/day, 250 mg/m²/day, 275 mg/m²/day, or 300 mg/m²/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m²/day i.v. In some embodiments, the cyclophosphamide treatment is administered for 4 days at 250 mg/m²/day i.v.

In some embodiments, lymphodepletion is performed by administering the fludarabine and the cyclophosphamide are together to a patient. In some embodiments, fludarabine is administered at 25 mg/m²/day i.v. and cyclophosphamide is administered at 250 mg/m²/day i.v. over 4 days.

In an embodiment, the lymphodepletion is performed by administration of cyclophosphamide at a dose of 60 mg/m²/day for two days followed by administration of fludarabine at a dose of 25 mg/m²/day for five days.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Figure 2:
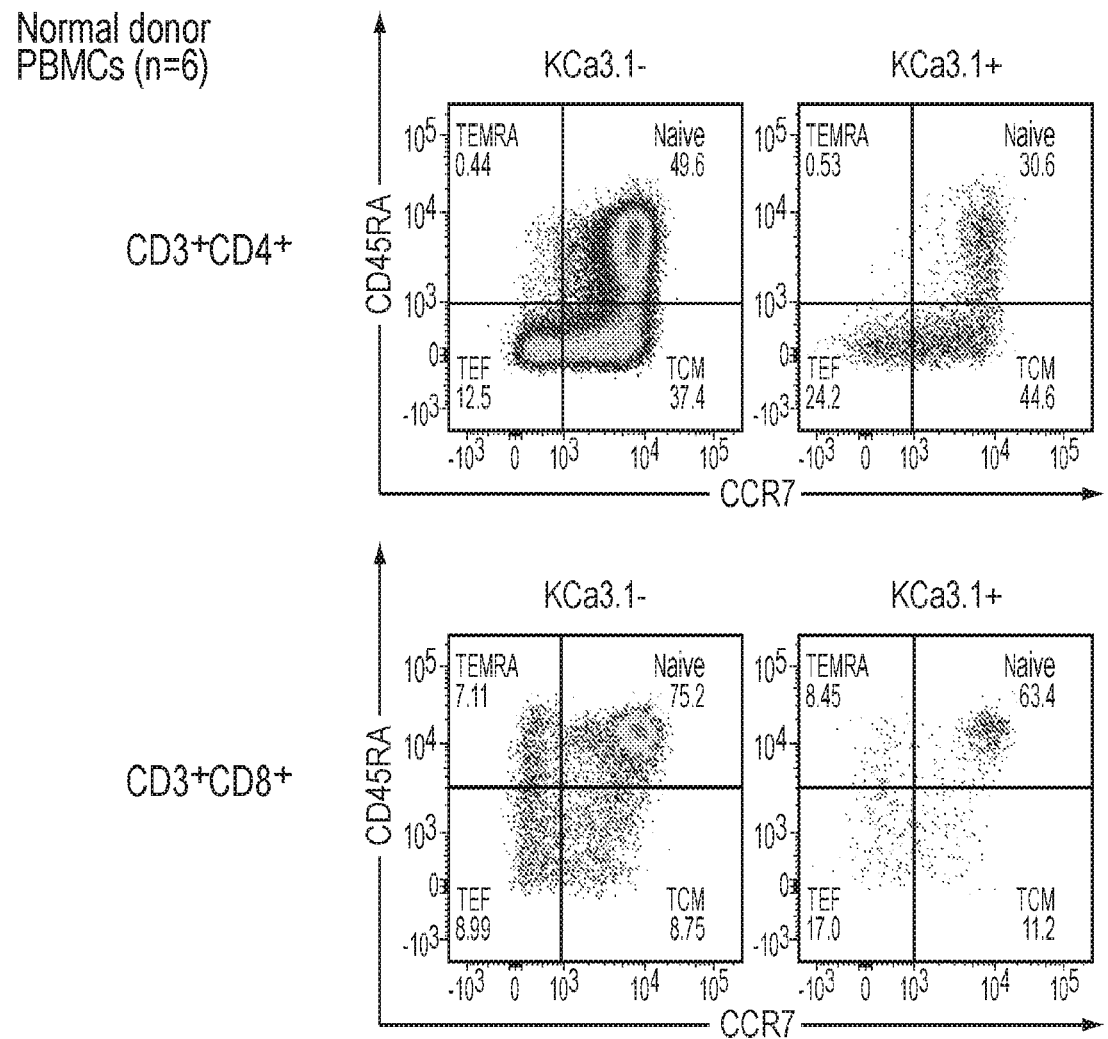
FIG. 2. illustrates the results of flow cytometry experiments performed using the strategy depicted in FIG. 1. The top panel shows the CD3$^+$CD4$^+$ subset and the bottom panel shows the CD3$^+$CD8$^+$ subset. Both $K_{Ca}3.1^+$ and $K_{Ca}3.1^-$ subsets are shown.
Figure 3:
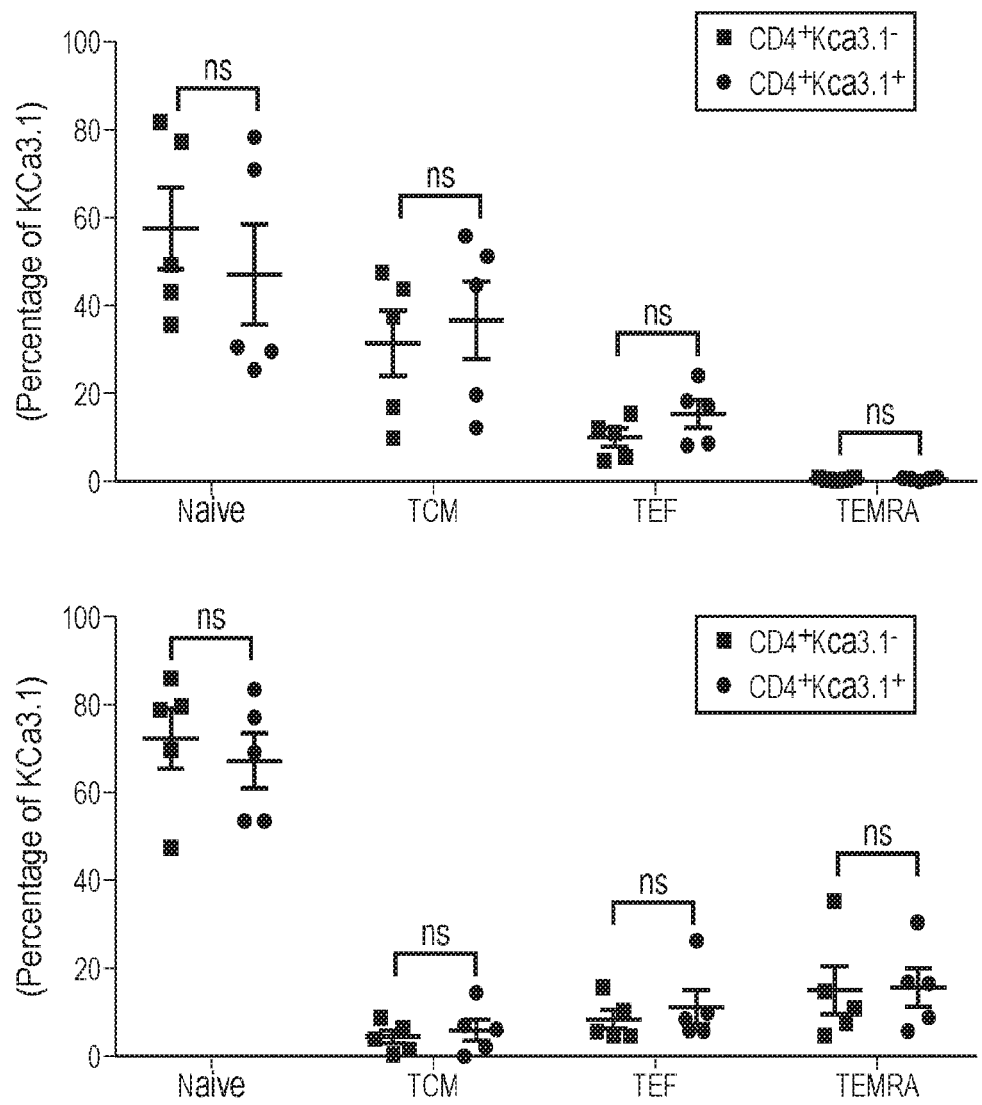
FIG. 3 illustrates the expression of four T cell subsets: naïve, central memory (TCM), effector memory (TEF), and effector memory RA$^+$ (TEMRA) cells. The top panel shows the CD3$^+$CD4$^+$ subset and the bottom panel shows the CD3$^+$CD8$^+$ subset. Both $K_{Ca}3.1^+$ and $K_{Ca}3.1^-$ subsets are shown.

Example 1—Expression of $K_{Ca}3.1$ $K_{Ca}3.1$ is widely expressed by all T cell subsets in normal donor PBMCs. The T cell subset is defined using CD45RA and CCR7, namely naïve, central memory (TCM), effector memory (TEF), and effector memory RA$^+$ (TEMRA) cells, and the cell sorting strategy shown in FIG. 1 was performed using a Becton, Dickinson & Co. (BD) FACS CANTO II flow cytometry system. Normal donor PBMCs were stained with anti-CD3, anti-CD4, anti-CD8, anti-KCa3.1, anti-CD45RA, and anti-CCR7 and analyzed by flow cytometry (n=6). The percentage of KCa3.1 expression is demonstrated in each T cell subset, namely the CD3$^+$CD4$^+$ (FIG. 2A and FIG. 3A) and CD3$^+$CD8$^+$ subsets (FIG. 2B and FIG. 3B). No statistical difference in $K_{Ca}3.1$ expression in each T cell subset is found using student's unpaired T test (p values <0.05 are considered statistically significant).

To study kinetic expression of $K_{Ca}3.1$, wo normal donor PBMC lines and three TIL lines from melanoma tumors were activated with anti-CD3 and anti-CD28 with the $K_{Ca}3.1$ agonist SKA-31 (Formula (2)). PBMCs and TILs at day 0 (baseline) were used as controls for $K_{Ca}3.1$ expression. Normal donor PBMCs and three TIL lines (M004, M1011, and M1023) were thawed and cultured in TIL culture media (TIL CM) containing RPMI 1640 (Thermo Fisher Scientific, Waltham, Mass., USA), 1 mM Glutamax (Thermo Fisher Scientific), 1 mM pyruvate (Thermo Fisher Scientific), 50 µM 2-mercaptoethanol (Thermo Fisher Scientific), and 1× Pen-Strep (Thermo Fisher Scientific), and 10% human AB serum (Gemini Bio-Products, West Sacramento, Calif., USA) with IL-2 (6000 IU/mL) (CellGenix Inc., Portsmouth, N.H., USA). On the next day, PBMCs were activated with anti-CD3 (Clone CLB-T3/4.E, Cell Sciences) (1 µg/mL) and anti-CD28 (Clone 28.2, BioLegend, San Diego, Calif., USA) (500 ng/mL) with or without 50 nM SKA-31 (Sigma-Aldrich Co., St. Louis, Mo., USA). TILs were stimulated with anti-CD3 (Clone CLB-T3/4.E, 1XE mAB, Cell Sciences) (100 ng/mL) and anti-CD28 (500 ng/mL) with or without 50 nM SKA-31. Cells were harvested on day 1, 3, and 7 following activation, stained with anti-CD3 (clone SP34-2, BD Biosciences), anti-CD8 (clone RPA-T8, BioLegend), anti-$K_{Ca}3.1$ (Polyclonal, Alomone Lab), and AmCyan (Thermo Fisher Scientific), and analyzed by flow cytometry using a BD FACS CANTO II system.

Figure 4:
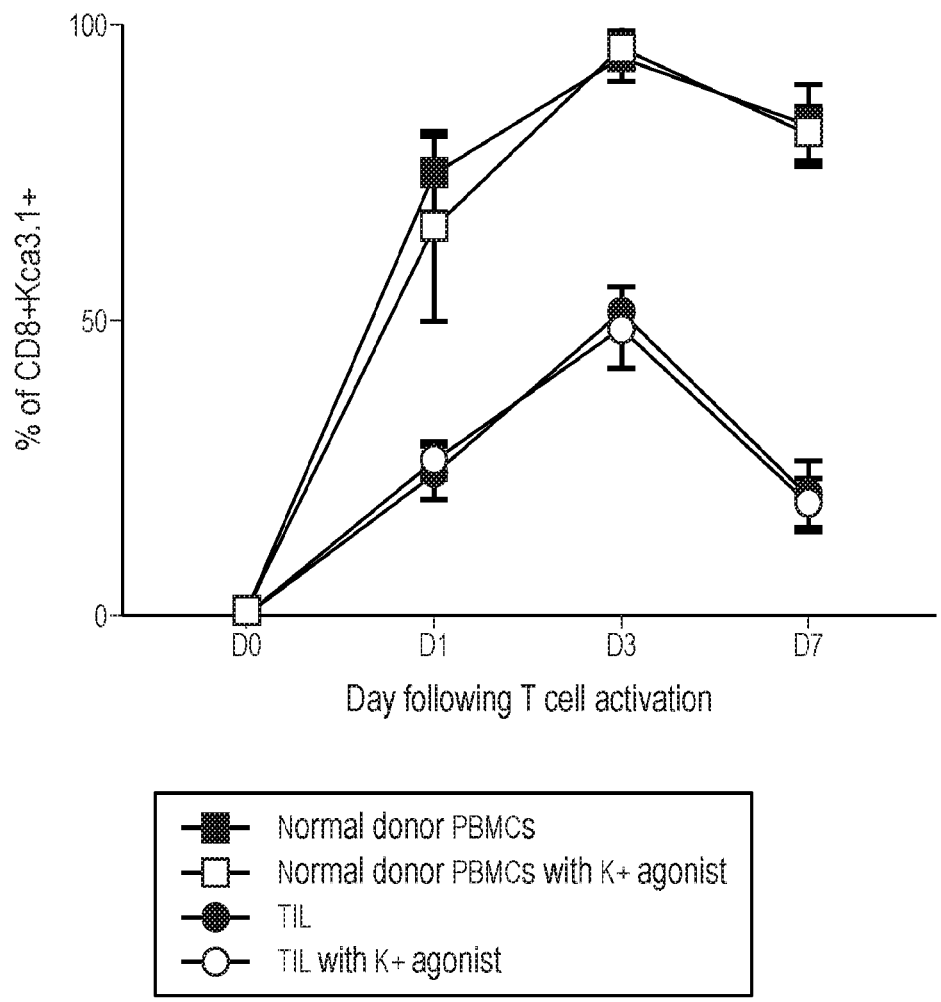
FIG. 4 illustrates kinetic expression of $K_{Ca}3.1$ in two normal donor peripheral blood mononuclear cell (PBMC) lines and in three melanoma TIL lines. The cells were harvested and stained with anti-CD3, anti-CD8, anti-$K_{Ca}3.1$, and Amcyan on day 1, 3, and 7 following activation to determine the kinetic expression of $K_{Ca}3.1$.

The results are shown in FIG. 4. Upon T cell activation with anti-CD3 (OKT3), $K_{Ca}3.1$ expression was first observed on day 1. The highest expression was found on day 3. The expression gradually declined on day 7. In human PBMCs and TILs, $K_{Ca}3.1$ expression was relatively low with upregulation observed within 24 hours following stimulation with anti-CD3 and anti-CD28. The results show that the addition of the $K_{Ca}3.1$ agonist SKA-31 did not alter $K_{Ca}3.1$ expression. The results also demonstrate the surprising result that $K_{Ca}3.1$ channel expression was found to begin downregulation through day 7 of the REP, regardless of the presence or absence of the $K_{Ca}3.1$ agonist, so that the use of a $K_{Ca}3.1$ agonist may be effectively employed between day 0 and approximately day 7 to day 11 (or an appropriate period determined by downregulation) during the REP (or pre-REP) of TILs.

Figure 5:
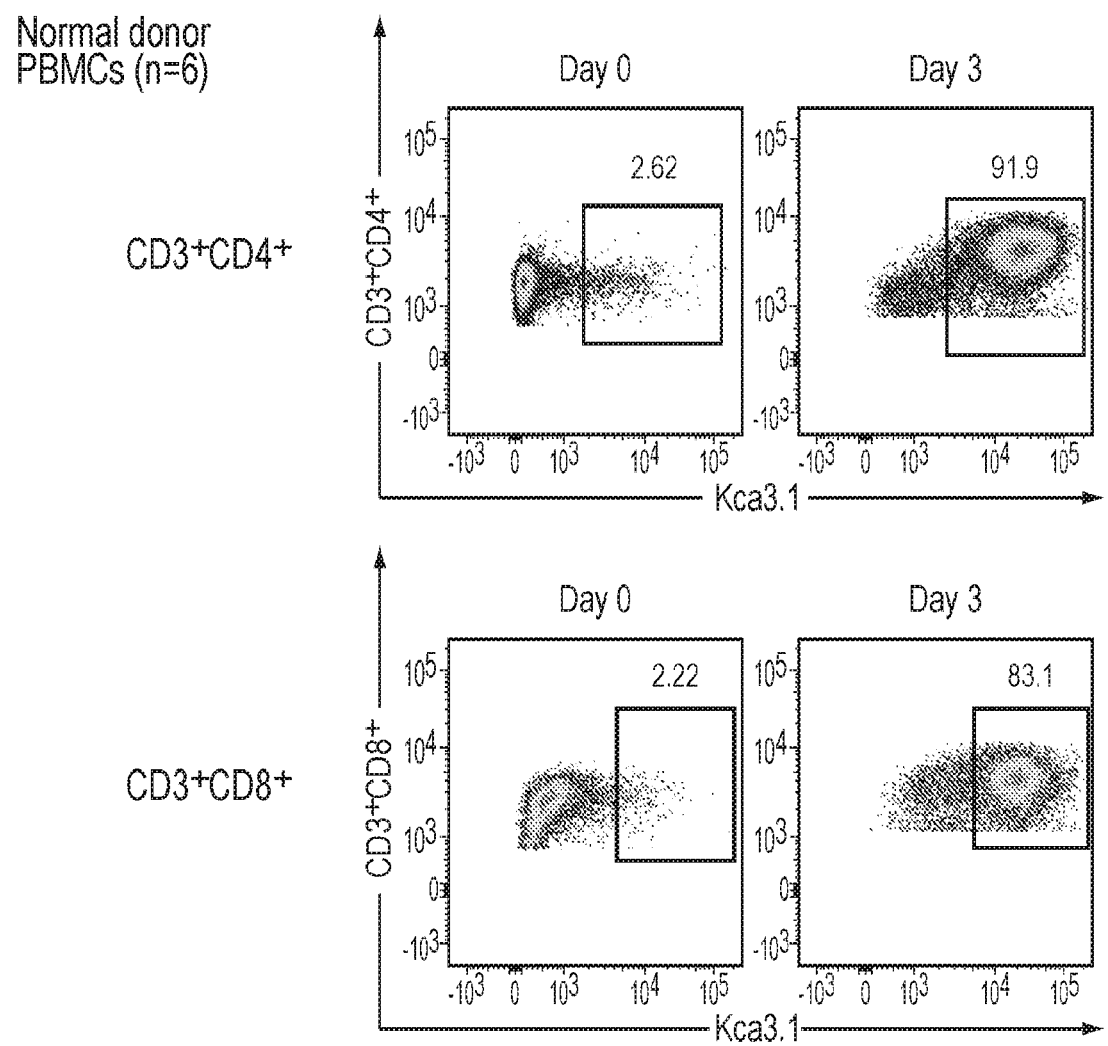
FIG. 5 illustrates flow cytometry data showing the percentage of $K_{Ca}3.1$ in CD3$^+$CD4$^+$ subset (top) and CD3$^+$CD8$^+$ subset (bottom) on day 0 and day 3 following TCR activation.
Figure 6:
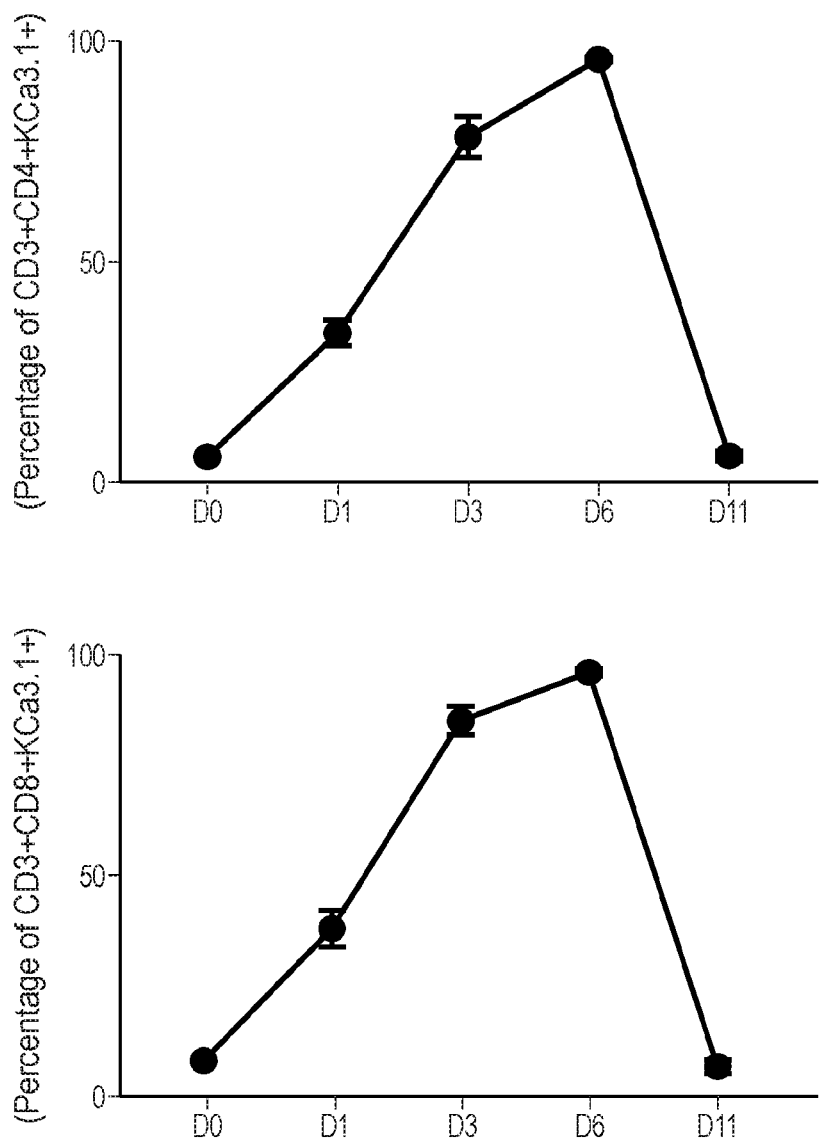
FIG. 6 illustrates kinetic expression of $K_{Ca}3.1$ within 3 day time course in CD3$^+$CD4$^+$ (top) and CD3$^+$CD8$^+$ subsets (bottom).

The upregulation of $K_{Ca}3.1$ expression following T cell activation was further explored. Normal donor PBMCs were activated with anti-CD3 (1000 ng/mL) and anti-CD28 (500 ng/mL) (n=6). Pseudocolor plots demonstrate the percentage of $K_{Ca}3.1$ in CD3$^+$CD4$^+$ subset (FIG. 5, top) and CD3$^+$CD8$^+$ subset (FIG. 5, bottom) on day 0 and day 3 following TCR activation. Kinetic expression of $K_{Ca}3.1$ within 3 day time course is demonstrated in CD3$^+$CD4$^+$ (FIG. 6, top) and CD3$^+$CD8$^+$ subsets (FIG. 6, bottom).

Heightened expression of $K_{Ca}3.1$ in pre-REP TILs (i.e., after culture in IL-2) was also observed. $K_{Ca}3.1$ expression was assessed by flow cytometry in normal donor PBMCs (n=6) and pre-REP TIL (n=8). Pseudocolor plots and dotplots represent the percentage of $K_{Ca}3.1$ expression demonstrated in CD3$^+$CD4$^+$ and CD3$^+$CD8$^+$ subsets of normal donor PBMCs and TILs (FIG. 7 and FIG. 8) (p values represent the difference between normal PBMCs and pre REP-TIL using student's unpaired T test, where p values <0.05 are considered statistically significant).

Example 2—a Potassium Channel Agonist Enhances TIL Expansion During REP

Melanoma TIL lines were propagated using a REP protocol for 14 days with or without the $K_{Ca}3.1$ agonist SKA-31 (Formula (2)). Ten TIL lines (M004, M1011, M1017, M1020, M1021, M1025, M1030, M1034, M1036, and M1045) were propagated with REP with anti-CD3 OKT-3 antibody (Miltenyi Biotech) (30 ng/mL) using irradiated PBMC feeder cells at ratio of TILs to feeder cells of 1 to 100 in G-REX 24 well plates (Wilson Wolf Manufacturing). Approximately 1×10$^6$ TILs were used per G-REX 24 well on day 0 in 8 mL of TIL REP media (TIL CM and Aim V media (Thermo Fisher Scientific) at a 1 to 1 ratio) with or without 50 mM of SKA-31. On day 2, the cultures were supplemented with IL-2 (6000 IU/mL). Half of the media was replaced with fresh AIMV media on day 5 with or without 50 mM SKA-31. The REP cultures were supplemented with IL-2 (3000 IU/mL) on day 9 and 12 respectively. On day 14, TILs were counted and calculated for fold expansion.

Figure 9:
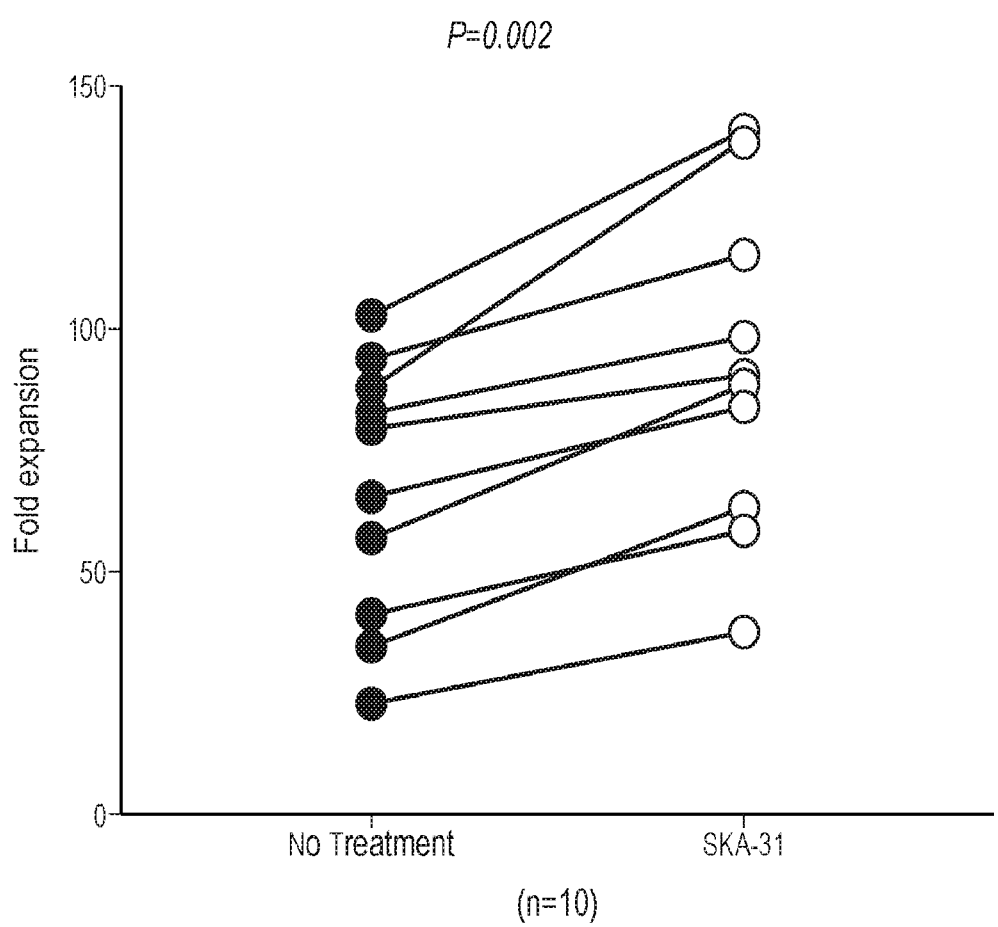
FIG. 9 illustrates the fold expansion of TILs from different lines in the presence of the $K_{Ca}3.1$ agonist SKA-31 ("SKA-31") relative to a control experiment performed without SKA-31 ("No Treatment").

The results are illustrated in FIG. 9. The observed fold expansion is significantly higher with the addition of the $K_{Ca}3.1$ agonist as compared to the control performed without $K_{Ca}3.1$ agonist. Surprisingly, TILs propagated in the REP had a 1.42-fold greater expansion (p=0.002) in the presence of SKA-31.

Example 3—TILs Treated with a Potassium Channel Agonist Exhibit a Less Differentiated Phenotype Ten melanoma TIL lines were expanded with the REP protocol for 14 days with or without the $K_{Ca}3.1$ agonist SKA-31 (Formula (2)) as in Example 2. At the end of each REP, TILs were harvested and phenotyped with anti-CD3 (clone SP34-2, BD Biosciences), anti-CD28 (clone CD28.2, BD biosciences), and anti-CD27 (M-T271, BD Biosciences) antibodies.

Figure 10:
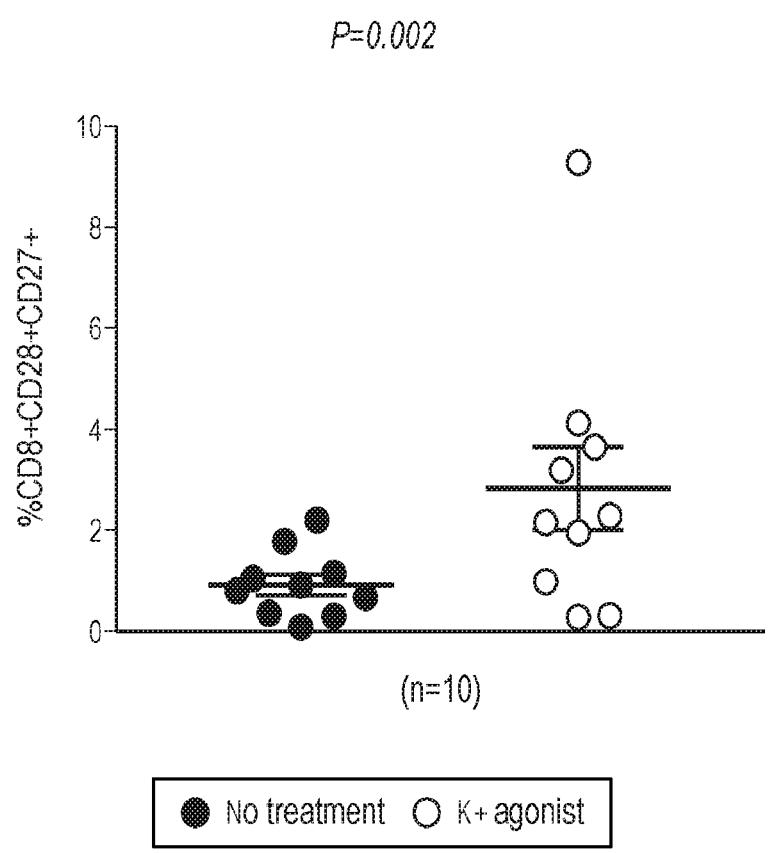
FIG. 10 illustrates the percentage of the CD8$^+$CD27$^+$CD28$^+$ T cell subset observed in TILs treated with the $K_{Ca}3.1$ agonist SKA-31 ("K+ agonist") compared to TILs treated without SKA-31 ("No treatment") during REP.
Figure 11:
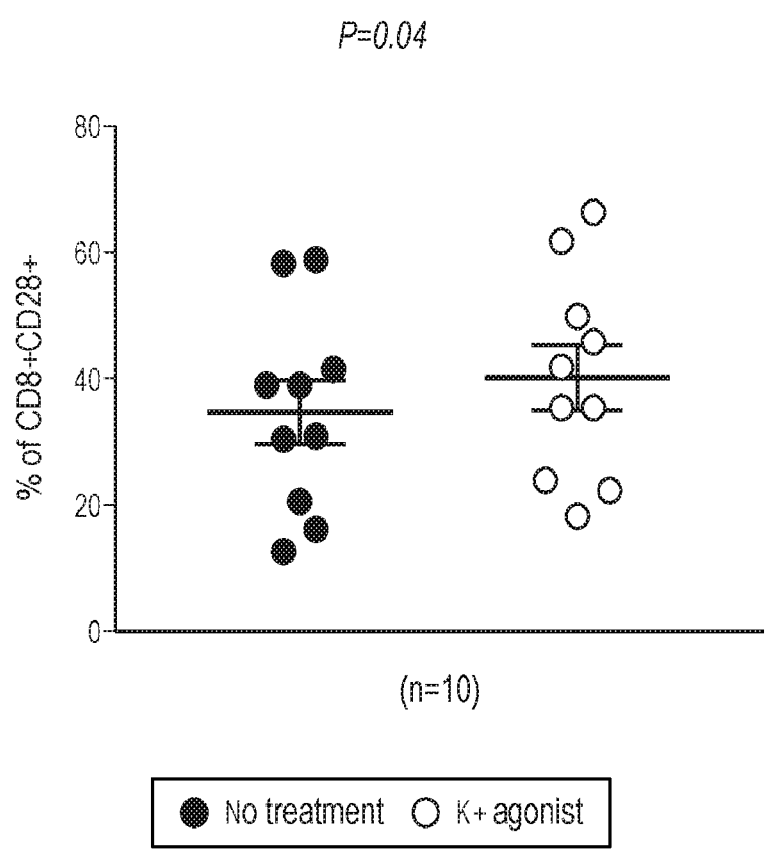
FIG. 11 illustrates the percentage of the CD8$^+$CD28$^+$ T cell subset observed in TILs treated with the $K_{Ca}3.1$ agonist SKA-31 ("K+ agonist") compared to TILs treated without SKA-31 ("No treatment") during REP.
Figure 12:
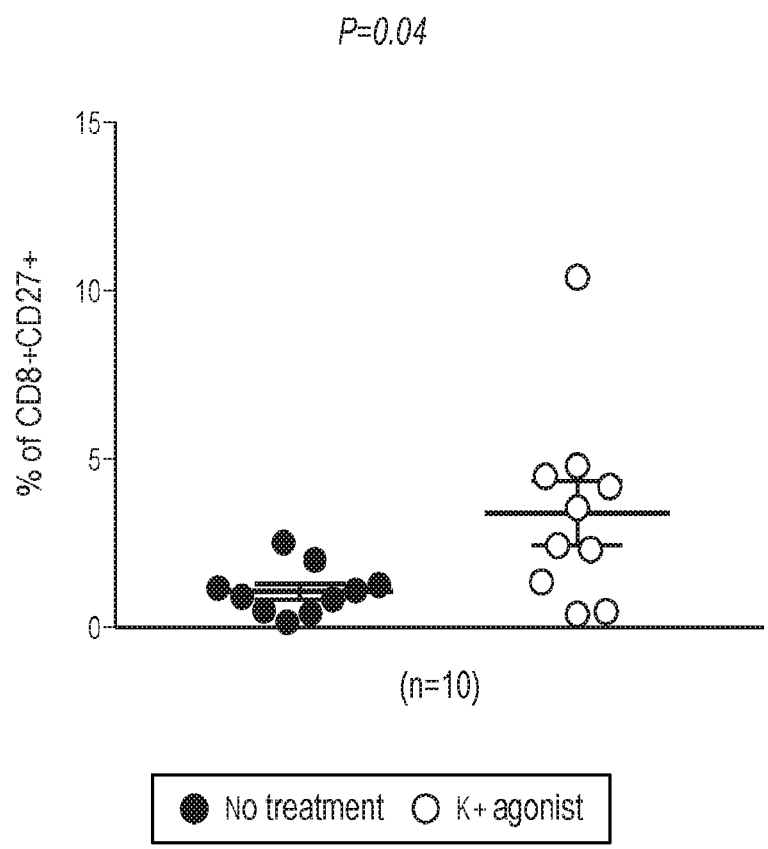
FIG. 12 illustrates the percentage of the CD8+CD27+ T cell subset observed in TILs treated with the $K_{Ca}3.1$ agonist SKA-31 ("K+ agonist") compared to TILs treated without SKA-31 ("No treatment") during REP.

The results are presented in FIG. 10, FIG. 11, and FIG. 12, and indicate that melanoma TILs treated with a $K_{Ca}3.1$ agonist SKA-31 exhibit a greater expansion of the CD8$^+$ CD28$^+$ (p=0.04), CD8$^+$CD27$^+$ (p=0.04), and CD8$^+$CD27$^+$ CD28$^+$ T cell subsets (p=0.002). Overall, the results show that TILs treated with a $K_{Ca}3.1$ agonist exhibit a surprisingly less differentiated phenotype, with greater subsets of CD8$^+$ CD27$^+$, CD8$^+$CD28$^+$, and CD8$^+$CD27$^+$CD28$^+$ T cells.

Figure 13:
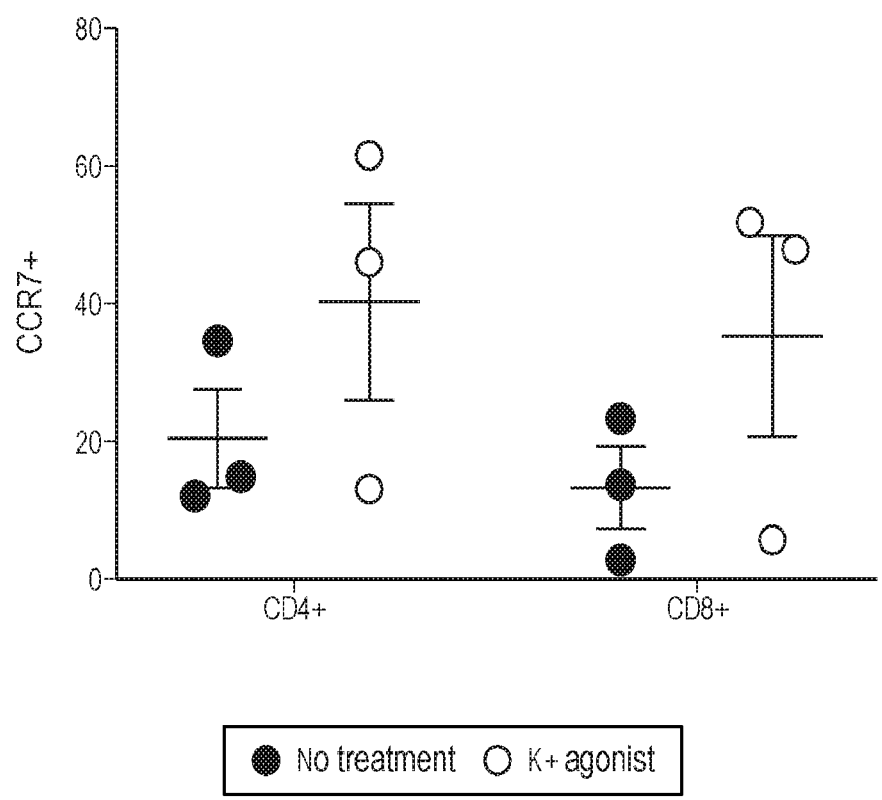
FIG. 13 illustrates increased CCR7+ expression in CD4+ and CD8+ TILs obtained from three tumor fragments (kidney, estrogen receptor positive (ER+) breast, and melanoma) treated with the $K_{Ca}3.1$ agonist SKA-31 ("K+ agonist") compared to TILs treated without SKA-31 ("No treatment") during pre-REP.
Figure 14:
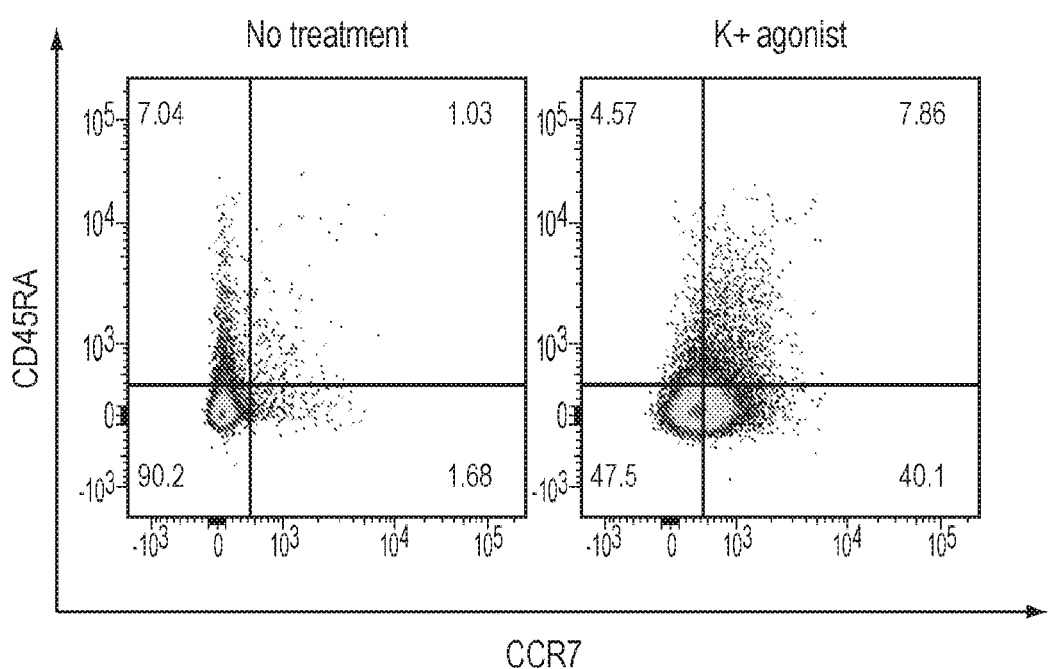
FIG. 14 illustrates the results of representative flow cytometry experiments performed to measure CCR7+ expression.

Example 4—A Potassium Channel Agonist Enhances CCR7$^+$ and CD25$^+$ Expression in Pre-REP TILs Three tumors (kidney, estrogen receptor positive (ER$^+$) breast, and melanoma) were grown with either IL-2 alone or IL-2 with SKA-31 at a to evaluate the performance of a $K_{Ca}3.1$ agonist in the pre-REP stage. The resected tumor samples were cut into 3-5 mm$^2$ fragments. Four to eight tumor fragments were placed into GREX-10 flask containing TIL CM (previously described) with IL-2 (6000 IU/mL) with or without 100 nM SKA-31. The culture was supplemented with IL-2 every 5 days until harvested. After three weeks, TIL was collected, counted, and stained with anti-CD8 (clone RPA-T8, BioLegend), anti-CD4 (OKT-4, BioLegend), anti-CCR7 (BioLegend G043H7), or AmCyan (Thermo Fisher Scientific), and analyzed by flow cytometry using a BD FACS CANTO II system. The results of CCR7 expression in the three tumor fragments are presented in FIG. 13, with representative flow cytometry results for one of the tumors presented in FIG. 14.

Figure 7:
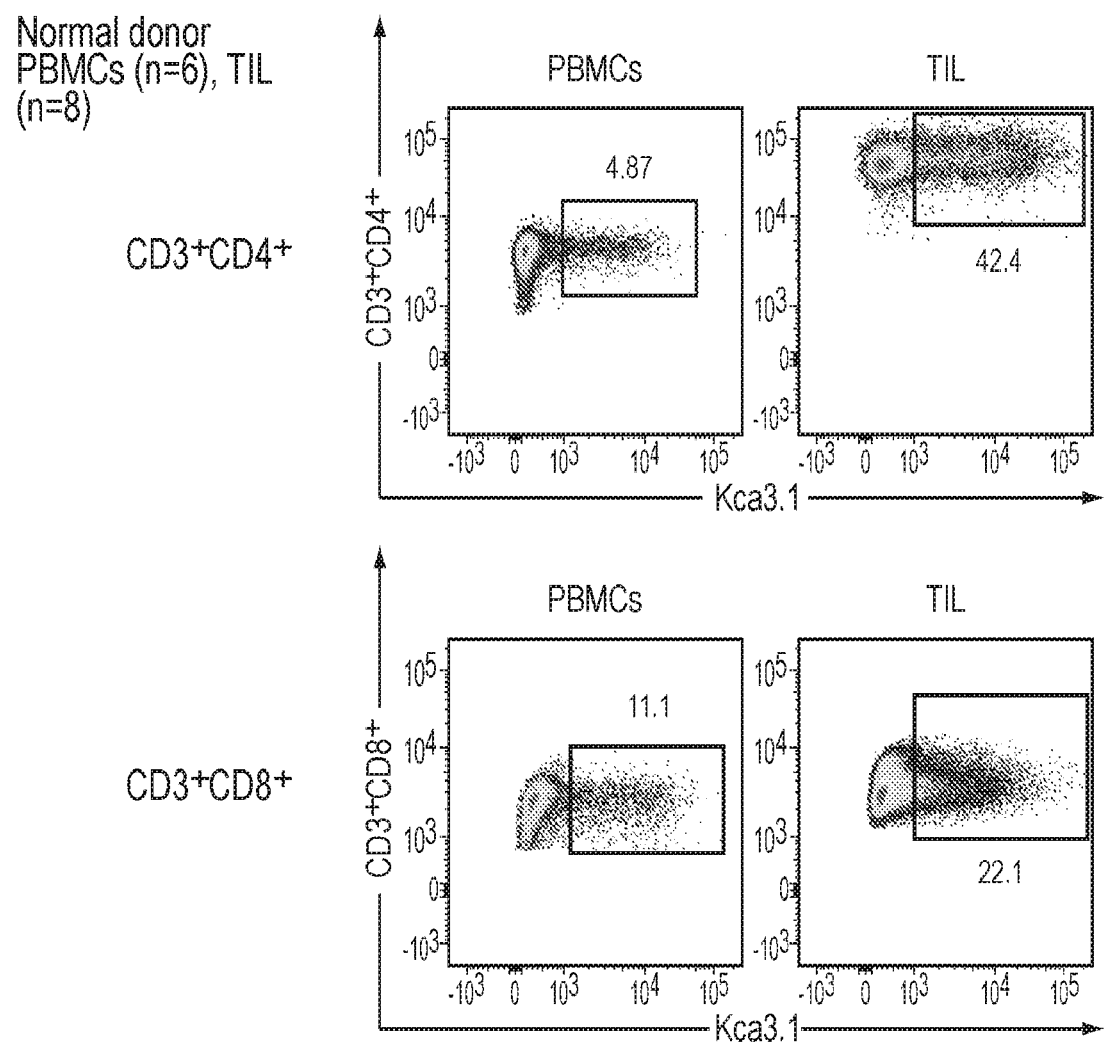
FIG. 7 illustrates flow cytometry data showing $K_{Ca}3.1$ expression in CD3$^+$CD4$^+$ (top) and CD3$^+$CD8$^+$ (bottom) subsets of normal donor PBMCs compared to TILs.
Figure 8:
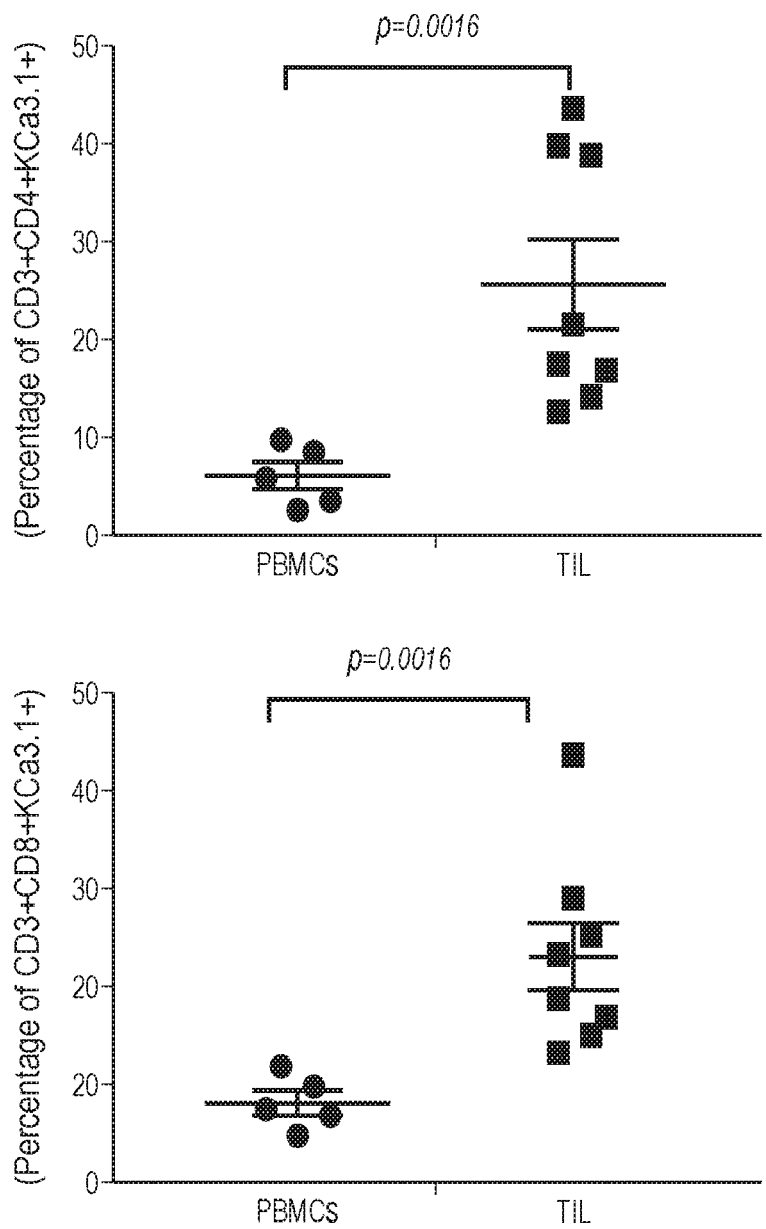
FIG. 8 illustrates the percentage of $K_{Ca}3.1$ expression observed in CD3$^+$CD4$^+$ (top) and CD3$^+$CD8$^+$ (bottom) subsets of normal donor PBMCs compared to TILs (p values represent the difference between normal PBMCs and pre REP-TIL using student's unpaired T test, and p values <0.05 are considered statistically significant).

CCR7 is associated with memory T cells, and promotes TIL expansion, and attenuates T-cell differentiation. Campbell, et al., *J. Immunol.* 2001, 166, 877-84; Gattinoni, et al., *Nature Med.* 2011, 17, 1290-97; Zhou, et al., *J. Immunol.* 2005, 175, 7046-52. The results in FIG. 6 and FIG. 7 show that a $K_{Ca}3.1$ agonist surprisingly enhances the expression of CCR7 in TILs, which may provide for better clinical performance of TILs expanded using a $K_{Ca}3.1$ agonist.

Figure 15:
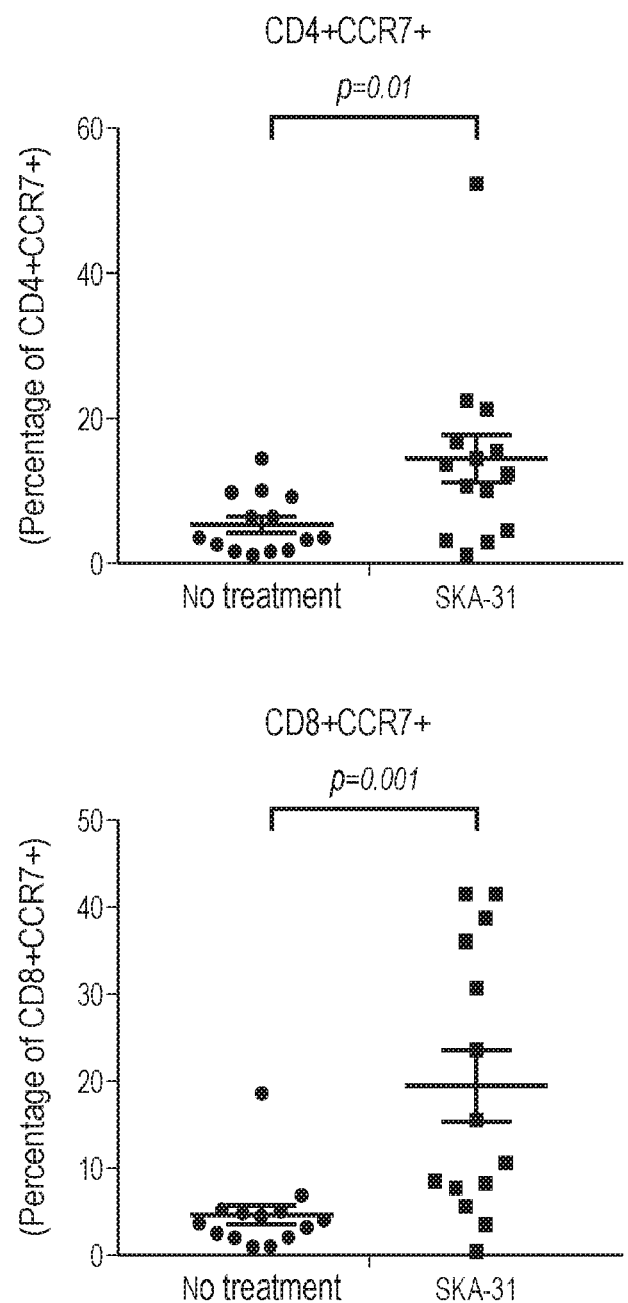
FIG. 15 illustrates statistically significant increased CCR7+ expression in CD4+ and CD8+ TILs obtained from fourteen tumor fragments.
Figure 16:
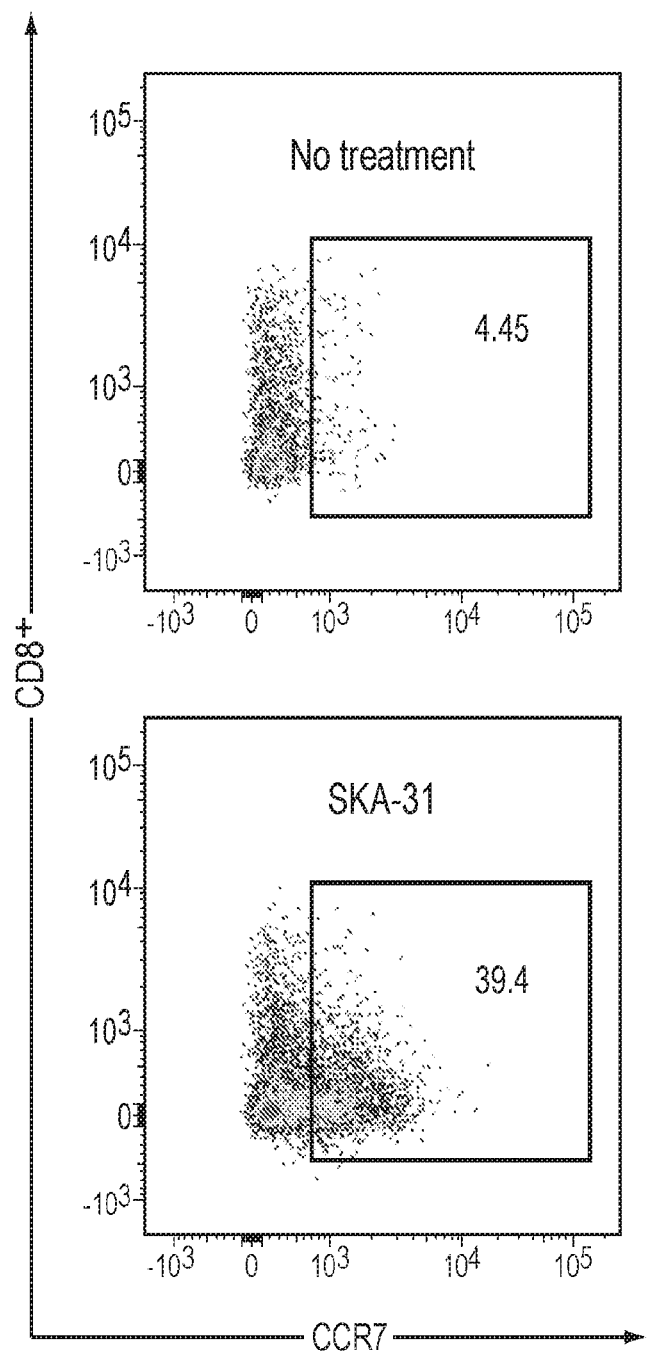
FIG. 16 illustrates the results of representative flow cytometry experiments performed to measure CCR7+ expression.
Figure 17:
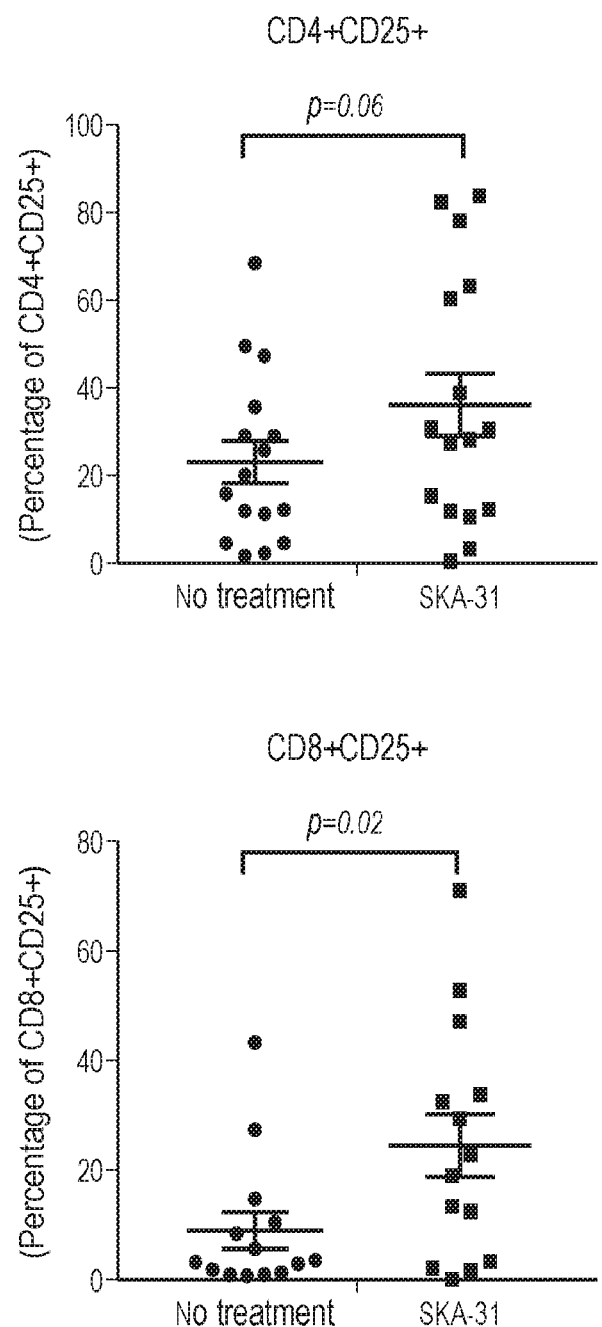
FIG. 17 illustrates statistically significant increased CD25+ expression in CD4+ and CD8+ TILs obtained from sixteen tumor fragments.
Figure 18:
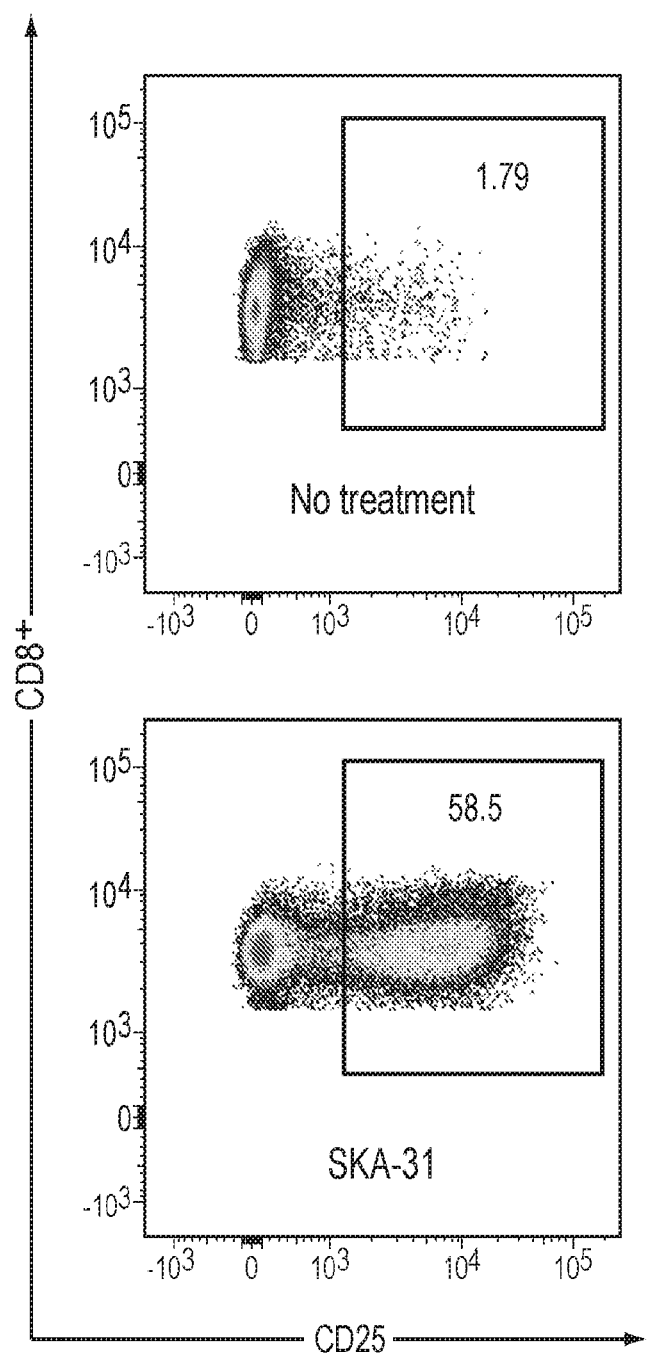
FIG. 18 illustrates the results of representative flow cytometry experiments performed to measure CD25+ expression.

Further evidence that SKA-31 enhances expression of CD25 and CCR7 was also obtained. Pre-REP TIL were grown with either IL-2 (6000 IU/mL) alone or with SKA-31 and were analyzed after 21 days (n=14; tumor types: breast cancer (8), melanoma (3), kidney (2), ovarian (1)). CCR7$^+$ expression was assessed by flow cytometry in CD4$^+$ (FIG. 15, top) and CD8$^+$ subsets (FIG. 15, bottom). A representative flow cytometry experiment is shown in FIG. 16. CD25$^+$ expression was assessed by flow cytometry in CD4$^+$ (FIG. 17, top) and CD8$^+$ subsets (FIG. 17, bottom) (n=16, breast cancer (8), melanoma (3), kidney (3), ovarian (2)). A representative flow cytometry experiment is shown in FIG. 18. In both cases, p values represent the difference between no treatment and SKA-31 using student's unpaired T test, and p values <0.05 are considered as statistically significant.

Example 5—A Potassium Channel Agonist Enhances Expansion of CD3$^+$CD8$^+$ Pre-REP TILs Tumor fragments from ovarian and breast cancer (triple positive, ER$^+$/PR$^+$/HER2$^+$) tumors were grown in a pre-REP stage with either IL-2 alone or IL-2 with SKA-31 (Formula (2)) at a concentration of 50 nM. The resected tumor samples were cut into 3-5 mm$^2$ fragments. Four to eight tumor fragments were placed into GREX-10 flasks containing TIL CM (previously described) with IL-2 (6000 IU/mL). The culture was supplemented with IL-2 every 5 days until harvested. After three weeks, TILs were collected, counted, and stained with anti-CD8 antibody (clone RPA-T8, BioLegend), anti-CD4 antibody (OKT-4, BioLegend), anti-CD3 antibody (clone SP34-2, BD Biosciences), and AmCyan (Thermo Fisher Scientific), and analyzed by flow cytometry using a BD FACS CANTO II system.

Figure 19:
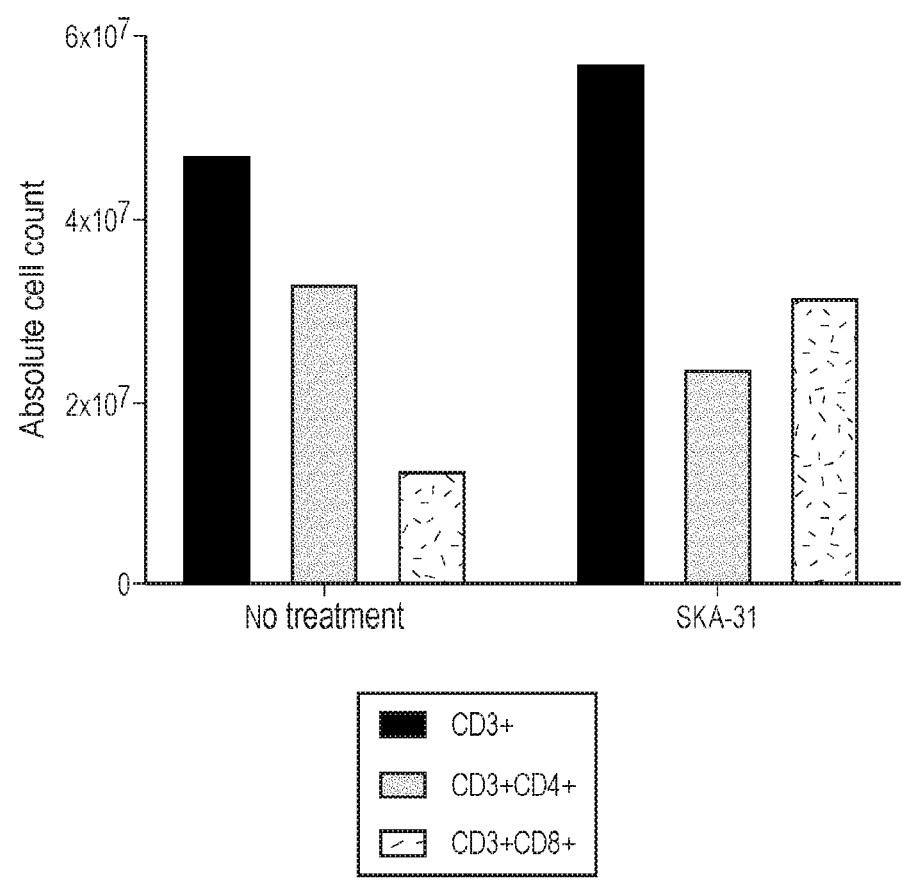
FIG. 19 illustrates absolute cell counts obtained for an ovarian tumor during pre-REP treated with the $K_{Ca}3.1$ agonist SKA-31 ("SKA-31") compared to TILs treated without SKA-31 ("No treatment").
Figure 20:
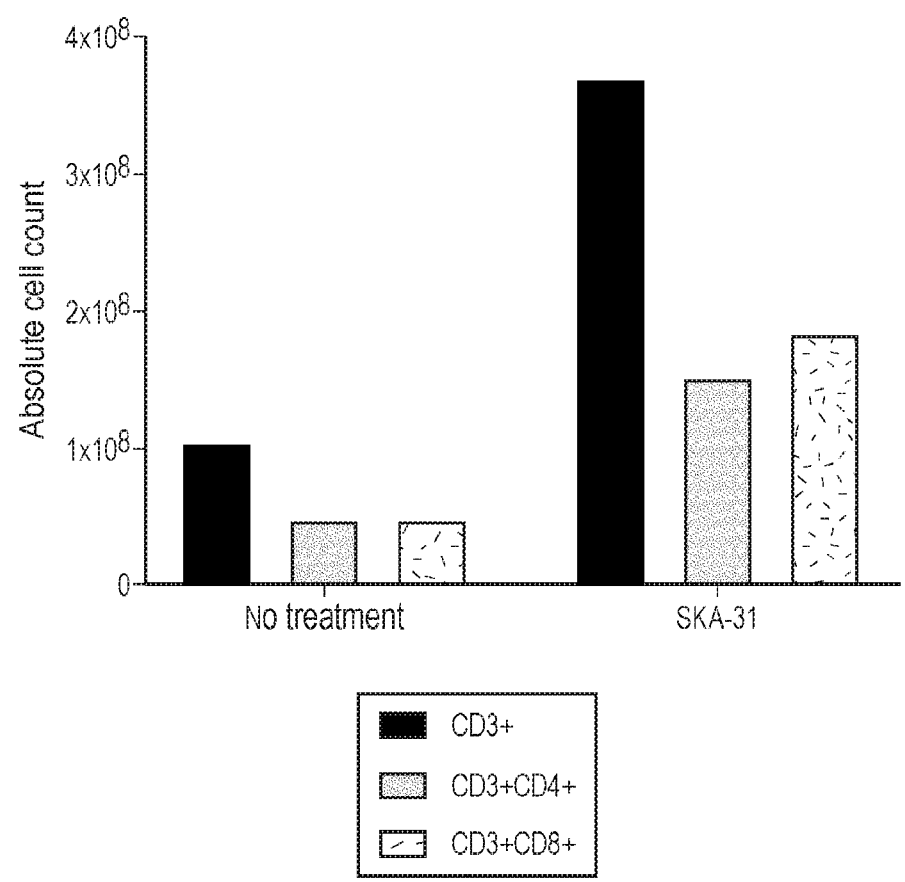
FIG. 20 illustrates absolute cell counts obtained for a breast tumor during pre-REP treated with the $K_{Ca}3.1$ agonist SKA-31 ("SKA-31") compared to TILs treated without SKA-31 ("No treatment").

The results are presented in FIG. 19, and show increased absolute cells counts in the presence of $K_{Ca}3.1$ agonist for TILs obtained from ovarian tumor fragments for CD3$^+$CD8$^+$ TILs. In FIG. 20, the results for breast tumor fragments show increased absolute cell counts for both CD3$^+$CD4$^+$ TILs and CD3$^+$CD8$^+$ TILs. Surprisingly, a $K_{Ca}3.1$ agonist was found to enhance the expansion and absolute cells counts of therapeutically-useful pre-REP TILs. A high proportion of CD3$^+$CD8$^+$ T cells in pre-REP TILs leads to a superior final TIL product after REP that has been shown to be strongly associated with clinical responses in TIL treated patients.

Figure 21:
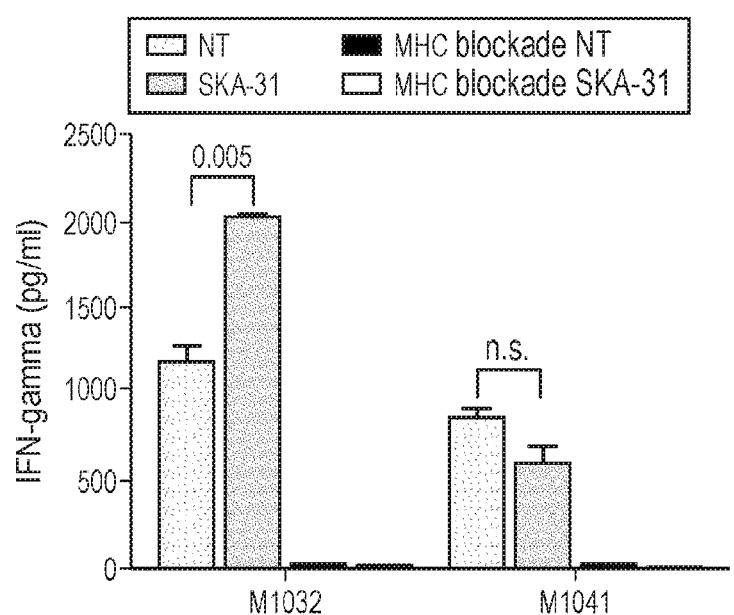
FIG. 21 illustrates IFN-γ secretion results from TILs after co-culture of melanoma tumor cells and TIL together for 24 hours at a 3:1 effector:target (E:T) ratio, using TILs prepared with and without SKA-31. NT refers to no treatment (i.e., TILs prepared without SKA-31).
Figure 22:
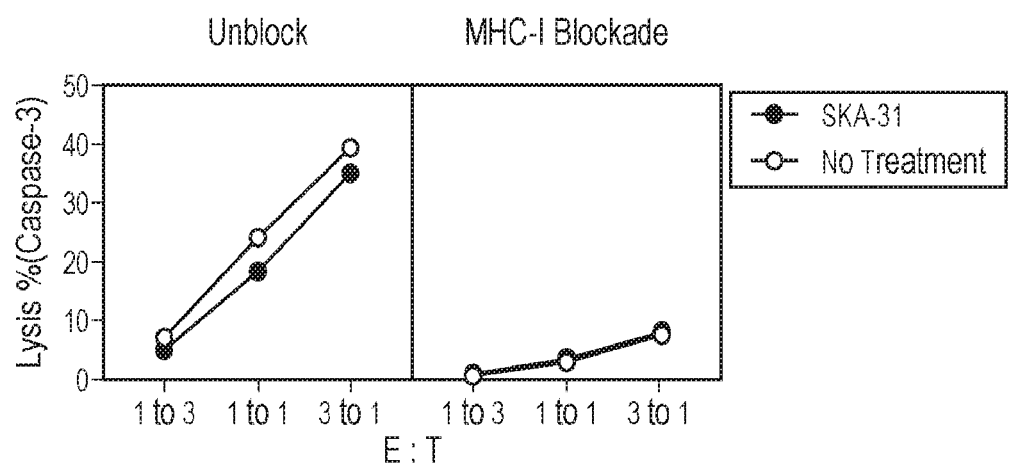
FIG. 22 illustrates killing potency (as measured by caspase-3) for the M1032 TIL cell line with MHC-I blockade (using antibody) and without MHC-I blockade ("unblocked") at different E:T ratios.
Figure 23:
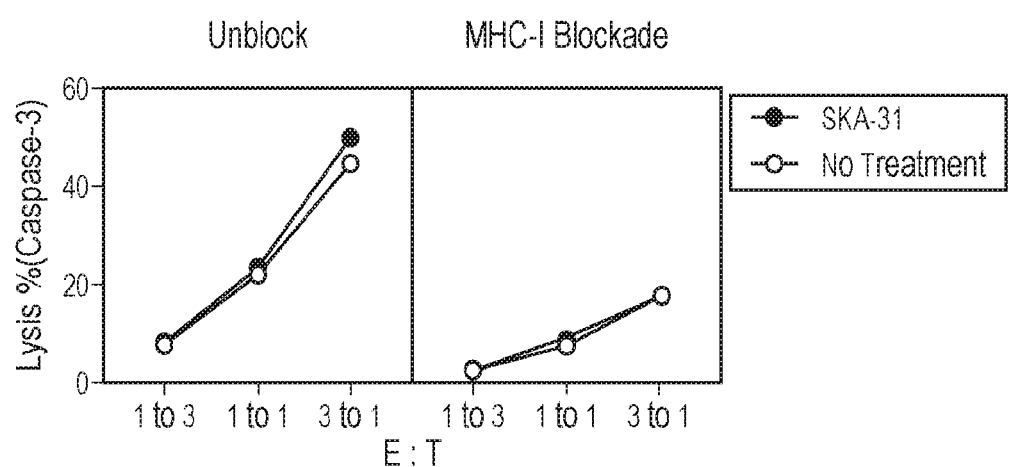
FIG. 23 illustrates killing potency (as measured by caspase-3) for the M1041 TIL cell line with MHC-I blockade (using antibody) and without MHC-I blockade ("unblocked") at different E:T ratios.

Example 6—Effects of a KCa3.1 Agonist on Interferon-γ Secretion and Tumor Killing Experiments were performed to demonstrate that a $K_{Ca}3.1$ agonist enhances and sustains IFN-γ secretion from TILs with no adverse effect on tumor killing. FIG. 21 illustrates the results of IFN-γ release as measured by enzyme-linked immunosorbent assay (ELISA). TILs prepared with and without SKA-31 were co-cultured with melanoma tumor cells for 24 hours at a TIL:melanoma cell ratio of 3:1 (i.e., a 3:1 effector:target or E:T ratio). Blocking of the TCR MHC-I was performed using 80 μg/mL of antibody clone W6/32 (BioLegend). The results are shown in FIG. 21. A statistically significant increase in IFN-γ release is observed for one TIL cell line, and no adverse effect on IFN-γ release from a second TIL cell line. The MHC-I blockade results demonstrate that the killing is caused by T cell lytic killing, and not cytokine, NK cell, or other mechanisms. FIG. 22 shows the results of cell killing for the M1032 line, at different E:T ratios, via the caspase-3 marker for apototic melanoma cells. FIG. 23 shows the results of cell killing for the M1041 line, at different E:T ratios, via the caspase-3 marker for apototic melanoma cells. In both cases, no adverse effects on tumor killing are observed from use of the $K_{Ca}3.1$ agonist SKA-31.

Example 7—Methods of Expanding TILs and Treating Cancer with Expanded TILs

Targeting the $K_{Ca}3.1$ channel is a novel strategy to expand and sustain less differentiated TILs for clinical applications of adoptive T cell therapy. $K_{Ca}3.1$ is expressed by all T-cell subsets including naïve, central memory (TCM), effector memory (TEF), and effector memory CD45RA+ (TEMRA) cells. Significant up-regulation of $K_{Ca}3.1$ is found within 24 hours following T cell activation. TILs have significantly higher level of $K_{Ca}3.1$ as compared to normal T cells in peripheral blood (PBMCs), which suggests that TILs are activated T lymphocytes. Activation of $K_{Ca}3.1$ channels with an exemplary $K_{Ca}3.1$ agonist (SKA-31) promotes TIL expansion, and SKA-31 helps sustain $CD27^+$ and $CD28^+$ expression during TIL expansion. Increased CD25 expression and CCR7 expression is found in pre-REP TIL grown with IL-2 and SKA-31. Activation of the K+ channel is a novel strategy to promote TIL expansion and sustain a less differentiated phenotype, promoting long term engraftment.

Figure 24:
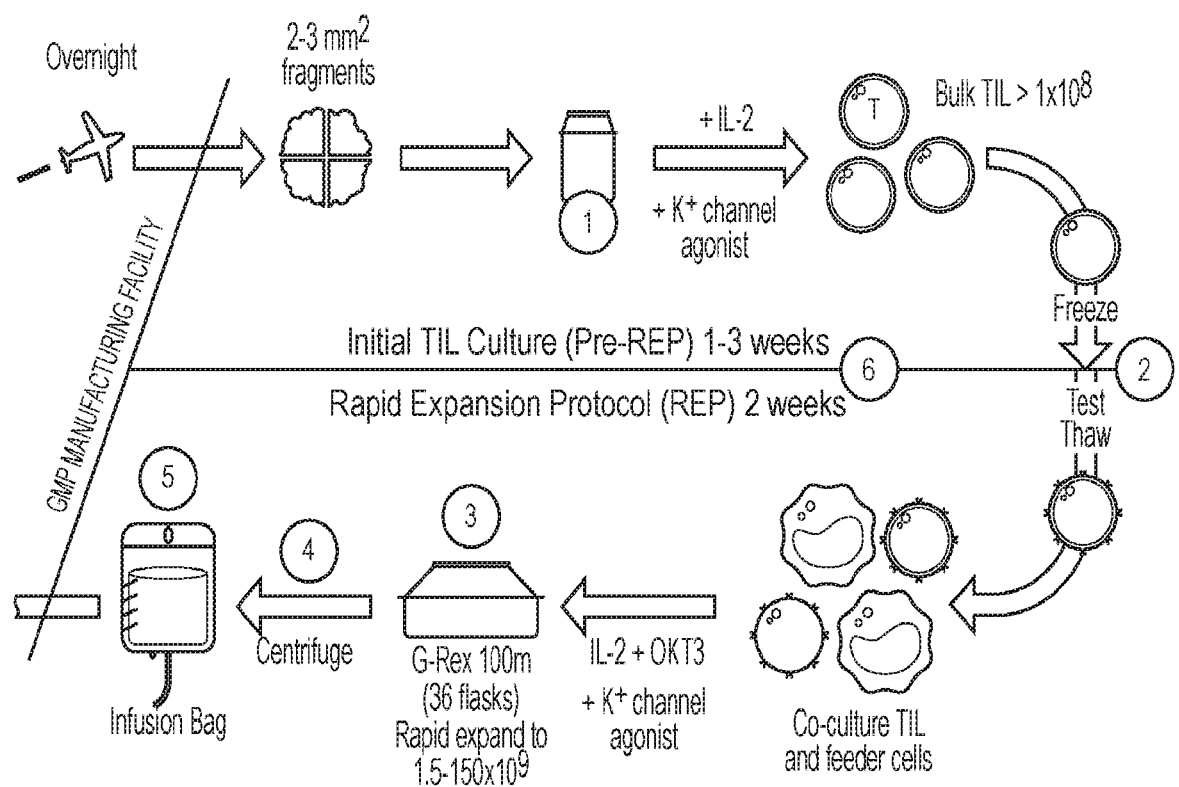
FIG. 24 illustrates a TIL expansion and treatment process. Potassium channel agonists of the present disclosure, including one or more $K_{Ca}3.1$ agonists of the present disclosure, may be used in both the pre-REP stage (top half of figure) and/or REP stage (bottom half of figure) and may be added when IL-2 is added to each cell culture. Step 1 refers to the addition of 4 tumor fragments into 10 G-Rex 10 flasks. At step 2, approximately 40×10⁶ TILs or greater are obtained. At step 3, a split occurs into 36 G-Rex 100 flasks for REP. TILs are harvested by centrifugation at step 4. Fresh TIL product is obtained at step 5 after a total process time of approximate 43 days, at which point TILs may be infused into a patient.
Figure 25:
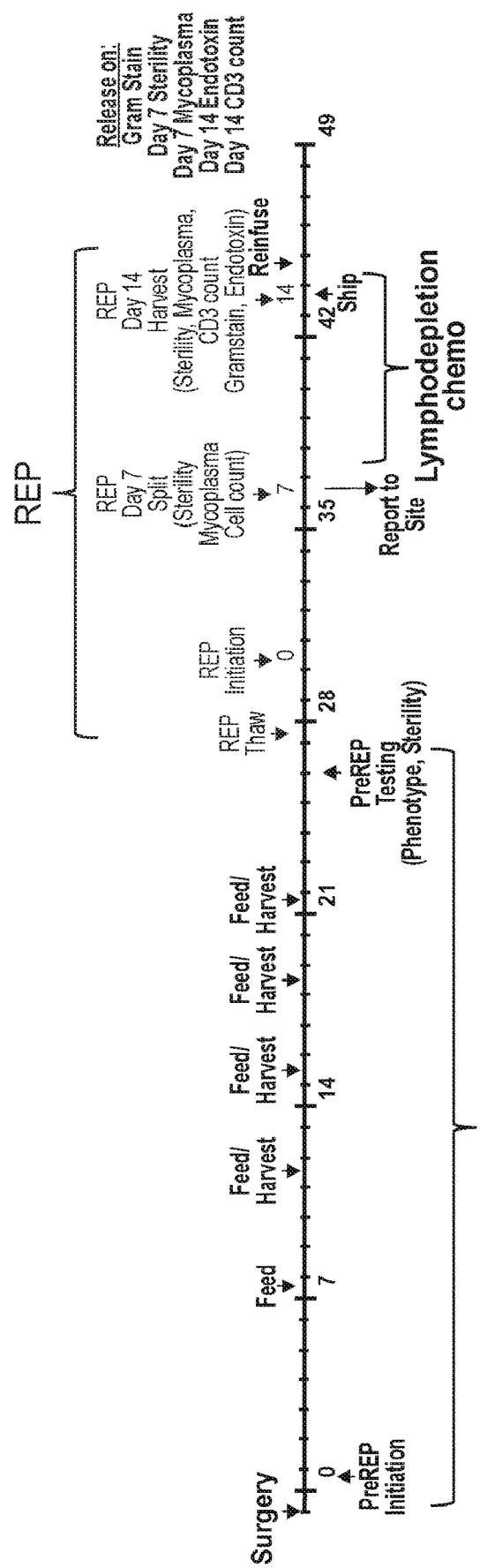
FIG. 25 illustrates a treatment protocol for use with TILs expanded with potassium channel agonists of the present disclosure. Surgery (and tumor resection) occurs at the start, and lymphodepletion chemo refers to non-myeloablative lymphodepletion with chemotherapy as described elsewhere herein. Potassium channel agonists of the present disclosure may also be used during therapy as described herein after administration of TILs.

TILs may be expanded using methods known in the art and any method described herein. For example, an exemplary method for expanding TILs is depicted in FIG. 24. A potassium channel agonist may be added to the method of FIG. 24 as described herein. The potassium channel agonist may be, for example, a $K_{Ca}3.1$ channel agonist described herein such as SKA-31 or SKA-20, and may be added during the pre-REP or the REP phases, or during both phases, at concentrations sufficient to enhance TIL growth as described herein. The expansion of TILs may be further combined with any method of treating cancer in combination with a potassium channel agonist in a patient described herein. An exemplary method for expanding TILs using a potassium channel agonist, such as a $K_{Ca}3.1$ channel agonist described herein, and treating a cancer patient with expanded TILs is shown in FIG. 25.

---

We claim:

1. A method of treating a cancer with a population of tumor infiltrating lymphocytes (TILs) comprising the steps of:
   (a) resecting a tumor from a patient, the tumor comprising a first population of TILs;
   (b) fragmenting the tumor into tumor fragments;
   (c) contacting the tumor fragments with a first cell culture medium;
   (d) performing an initial expansion of the first population of TILs in the first cell culture medium to obtain a second population of TILs, wherein the second population of TILs is at least 5-fold greater in number than the first population of TILs, wherein the first cell culture medium comprises IL-2;
   (e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and irradiated allogeneic peripheral blood mononuclear cells (PBMCs); and wherein the rapid expansion is performed over a period of 14 days or less;
   (f) harvesting the third population of TILs; and
   (g) administering a therapeutically effective portion of the third population of TILs to a patient with the cancer;
   wherein either the first cell culture medium or the second cell culture medium or both the first cell culture medium and the second cell culture medium further comprise a $K_{ca}3.1$ (IK channel) agonist.

2. The method of claim 1, wherein both the first cell culture medium and the second cell culture medium further comprise the $K_{ca}3.1$ agonist.

3. The method of claim 1, wherein the concentration of the $K_{ca}3.1$ agonist in the first cell culture medium is between 1 and 1000 nM.

4. The method of claim 1, wherein the initial expansion is performed over a period of 21 days or less.

5. The method of claim 1, wherein the rapid expansion is performed over a period of 7 days or less.

6. The method of claim 1, wherein the $K_{ca}3.1$ agonist is a compound according to Formula (1):

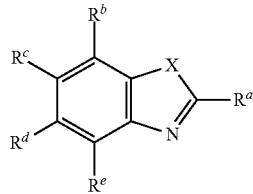

Formula (1)

or a pharmaceutically-acceptable salt, cocrystal, solvate, or prodrug thereof, wherein
$R^a$ is selected from halo, cyano, hydroxy, thiol, $(C_{1-6})$alkyl, —$NH_2$, and —$NR^1R^2$;
$R^1$ and $R^2$ are independently H or $(C_{1-6})$alkyl;
X is selected from the group consisting of S, O, and NH;
$R^b$ and $R^c$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^b$ and $R^c$ together with the carbon atoms to which they are attached form a ring selected from the group consisting of an aryl, naphthyl, anthryl, heteroaryl, cycloalkyl, and heterocycloalkyl ring; and
$R^d$ and $R^e$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^d$ and $R^e$ together with the carbon atoms to which they are attached form a ring selected from the group consisting of an aryl, naphthyl, anthryl, heteroaryl, cycloalkyl, and heterocycloalkyl ring;
with the proviso that if $R^b$ and $R^c$ form a ring, then $R^d$ and $R^e$ do not form a ring, and if $R^d$ and $R^e$ form a ring, then $R^b$ and $R^c$ do not form a ring.

7. The method of claim 1, wherein the $K_{ca}3.1$ agonist is selected from the group consisting of:
5-methylnaphtho[1,2-d]oxazol-2-amine;
5-ethylnaphtho[1,2-d]oxazol-2-amine;
5-propylnaphtho[1,2-d]oxazol-2-amine;
5-cyclopropylnaphtho[1,2-d]oxazol-2-amine;
5-(tert-butyl)naphtho[1,2-d]oxazol-2-amine;
5-fluoronaphtho[1,2-d]oxazol-2-amine;
5-chloronaphtho[1,2-d]oxazol-2-amine;
5-bromonaphtho[1,2-d]oxazol-2-amine;
5-iodonaphtho[1,2-d]oxazol-2-amine;
2-aminonaphtho[1,2-d]oxazole-5-carbonitrile;
naphtho[1,2-d]oxazol-2,5-diamine;

N⁵-methylnaphtho[1,2-d]oxazole-2,5-diamine;
N⁵,N⁵-dimethylnaphtho[1,2-d]oxazole-2,5-diamine;
N⁵-ethylnaphtho[1,2-d]oxazole-2,5-diamine;
5-(pyrrolidine-1-yl)naphtho[1,2-d]oxazol-2-amine;
5-methoxynaphtho[1,2-d]oxazol-2-amine;
5-trifluoromethylnaphtho[1,2-d]oxazol-2-amine;
5-methylnaphtho[2,1-d]oxazol-2-amine;
5-ethylnaphtho[2,1-d]oxazol-2-amine;
5-propylnaphtho[2,1-d]oxazol-2-amine;
5-cyclopropylnaphtho[2,1-d]oxazol-2-amine;
5-(tert-butyl)naphtho[2,1-d]oxazol-2-amine;
5-fluoronaphtho[2,1-d]oxazol-2-amine;
5-chloronaphtho[2,1-d]oxazol-2-amine;
5-bromonaphtho[2,1-d]oxazol-2-amine;
5-iodonaphtho[2,1-d]oxazol-2-amine;
2-aminonaphtho[2,1-d]oxazole-5-carbonitrile;
naphtho[2,1-d]oxazol-2,5-diamine;
N5-methylnaphtho[2,1-d]oxazole-2,5-diamine;
N5,N5-dimethylnaphtho[2,1-d]oxazole-2,5-diamine;
N5-ethylnaphtho[2,1-d]oxazole-2,5-diamine;
5-(pyrrolidine-1-yl)naphtho[2,1-d]oxazol-2-amine;
5-methoxynaphtho[2,1-d]oxazol-2-amine;
5-trifluoromethylnaphtho[2,1-d]oxazol-2-amine;
and pharmaceutically-acceptable salts, cocrystals, solvates, or prodrugs thereof.

8. The method of claim 1, wherein the IL-2 is present at an initial concentration of between 1000 IU/mL and 6000 IU/mL in the first cell culture medium.

9. The method of claim 1, further comprising the step of treating the patient with a non-myeloablative lymphodepletion regimen prior to administering the third population of TILs to the patient.

10. The method of claim 1, wherein the cancer is selected from the group consisting of melanoma, ovarian cancer, cervical cancer, lung cancer, bladder cancer, breast cancer, head and neck cancer, renal cell carcinoma, acute myeloid leukemia, colorectal cancer, non-small cell lung cancer (NSCLC), estrogen receptor positive (ER⁺) breast cancer, progesterone receptor positive (PR⁺) breast cancer, human epidermal growth factor receptor 2 (HER2⁺) breast cancer, triple positive breast cancer (ER⁺/PR⁺/HER2⁺), triple negative breast cancer (ER⁻/PR⁻/HER2⁻), double-refractory melanoma, uveal (ocular) melanoma and sarcoma.

11. A process for the preparation of a population of tumor infiltrating lymphocytes (TILs) from a tumor, the process comprising the steps of:
(a) fragmenting the tumor;
(b) performing an initial expansion of the first population of TILs in a first cell culture medium to obtain a second population of TILs, wherein the second population of TILs is at least 5-fold greater in number than the first population of TILs, wherein the first cell culture medium comprises IL-2;
(c) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), irradiated allogeneic peripheral blood mononuclear cells (PBMCs); and wherein the rapid expansion is performed over a period of 14 days or less;
(d) harvesting the third population of TILs; and
wherein either the first cell culture medium or the second cell culture medium or both the first cell culture medium and the second cell culture medium further comprise a $K_{ca}3.1$ (IK channel) agonist.

12. The process of claim 11, wherein the concentration of the $K_{ca}3.1$ agonist in the first cell culture medium is between 1 and 1000 nM.

13. The process of claim 11, wherein the initial expansion is performed over a period of 21 days or less.

14. The process of claim 11, wherein the rapid expansion is performed over a period of 7 days or less.

15. The process of claim 11, wherein the $K_{ca}3.1$ agonist is a compound according to Formula (1):

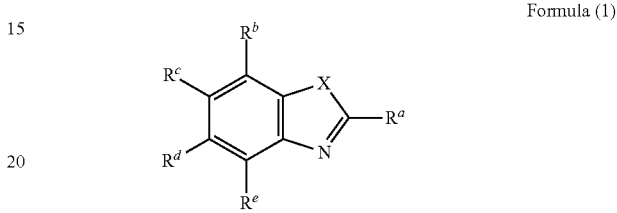

Formula (1)

or a pharmaceutically-acceptable salt, cocrystal, solvate, or prodrug thereof, wherein
$R^a$ is selected from halo, cyano, hydroxy, thiol, $(C_{1-6})$ alkyl, $-NH_2$, and $-NR^1R^2$;
$R^1$ and $R^2$ are independently H or $(C_{1-6})$alkyl;
X is selected from the group consisting of S, O, and NH;
$R^b$ and $R^c$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^b$ and $R^c$ together with the carbon atoms to which they are attached form a ring selected from the group consisting of an aryl, naphthyl, anthryl, heteroaryl, cycloalkyl, and heterocycloalkyl ring; and
$R^d$ and $R^e$ are independently selected from the group consisting of hydrogen, $(C_{1-6})$alkyl, $(C_{1-6})$alkoxyl, halo, nitro, aryl, heteroaryl, $(C_{1-6})$alkyl and $(C_{3-7})$cycloalkyl or $R^d$ and $R^e$ together with the carbon atoms to which they are attached form a ring selected from the group consisting of an aryl, naphthyl, anthryl, heteroaryl, cycloalkyl, and heterocycloalkyl ring;
with the proviso that if $R^b$ and $R^c$ form a ring, then $R^d$ and $R^e$ do not form a ring, and if $R^d$ and $R^e$ form a ring, then $R^b$ and $R^c$ do not form a ring.

16. The process of claim 11, wherein the $K_{ca}3.1$ agonist is selected from the group consisting of:
5-methylnaphtho[1,2-d]oxazol-2-amine;
5-ethylnaphtho[1,2-d]oxazol-2-amine;
5-propylnaphtho[1,2-d]oxazol-2-amine;
5-cyclopropylnaphtho[1,2-d]oxazol-2-amine;
5-(tert-butyl)naphtho[1,2-d]oxazol-2-amine;
5-fluoronaphtho[1,2-d]oxazol-2-amine;
5-chloronaphtho[1,2-d]oxazol-2-amine;
5-bromonaphtho[1,2-d]oxazol-2-amine;
5-iodonaphtho[1,2-d]oxazol-2-amine;
2-aminonaphtho[1,2-d]oxazole-5-carbonitrile;
naphtho[1,2-d]oxazol-2,5-diamine;
N⁵-methylnaphtho[1,2-d]oxazole-2,5-diamine;
N⁵,N⁵-dimethylnaphtho[1,2-d]oxazole-2,5-diamine;
N⁵-ethylnaphtho[1,2-d]oxazole-2,5-diamine;
5-(pyrrolidine-1-yl)naphtho[1,2-d]oxazol-2-amine;
5-methoxynaphtho[1,2-d]oxazol-2-amine;
5-trifluoromethylnaphtho[1,2-d]oxazol-2-amine;
5-methylnaphtho[2,1-d]oxazol-2-amine;
5-ethylnaphtho[2,1-d]oxazol-2-amine;

5-propylnaphtho[2,1-d]oxazol-2-amine;
5-cyclopropylnaphtho[2,1-d]oxazol-2-amine;
5-(tert-butyl)naphtho[2,1-d]oxazol-2-amine;
5-fluoronaphtho[2,1-d]oxazol-2-amine;
5-chloronaphtho[2,1-d]oxazol-2-amine;
5-bromonaphtho[2,1-d]oxazol-2-amine;
5-iodonaphtho[2,1-d]oxazol-2-amine;
2-aminonaphtho[2,1-d]oxazole-5-carbonitrile;
naphtho[2,1-d]oxazol-2,5-diamine;
N5-methylnaphtho[2,1-d]oxazole-2,5-diamine;
N5,N5-dimethylnaphtho[2,1-d]oxazole-2,5-diamine;
N5-ethylnaphtho[2,1-d]oxazole-2,5-diamine;
5-(pyrrolidine-1-yl)naphtho[2,1-d]oxazol-2-amine;
5-methoxynaphtho[2,1-d]oxazol-2-amine;
5-trifluoromethylnaphtho[2,1-d]oxazol-2-amine;
and pharmaceutically-acceptable salts, cocrystals, solvates, or prodrugs thereof.

17. The process of claim 11, wherein the IL-2 is present at an initial concentration of between 1000 IU/mL and 6000 IU/mL in the first cell culture medium.

* * * * *

SEQUENCE LISTING

```
<160> NUMBER OF SEQ ID NOS: 8

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Ala Lys Thr Thr Ala Pro Ser Val Tyr
            115                 120                 125

Pro Leu Ala Pro Val Cys Gly Gly Thr Thr Gly Ser Ser Val Thr Leu
```

```
                130               135               140
Gly Cys Leu Val Lys Gly Tyr Phe Pro Glu Pro Val Thr Leu Thr Trp
145               150               155               160

Asn Ser Gly Ser Leu Ser Ser Gly Val His Thr Phe Pro Ala Val Leu
                165               170               175

Gln Ser Asp Leu Tyr Thr Leu Ser Ser Val Thr Val Thr Ser Ser
            180               185               190

Thr Trp Pro Ser Gln Ser Ile Thr Cys Asn Val Ala His Pro Ala Ser
            195               200               205

Ser Thr Lys Val Asp Lys Lys Ile Glu Pro Arg Pro Lys Ser Cys Asp
    210               215               220

Lys Thr His Thr Cys Pro Pro Cys Pro Ala Pro Glu Leu Leu Gly Gly
225               230               235               240

Pro Ser Val Phe Leu Phe Pro Pro Lys Pro Lys Asp Thr Leu Met Ile
                245               250               255

Ser Arg Thr Pro Glu Val Thr Cys Val Val Val Asp Val Ser His Glu
                260               265               270

Asp Pro Glu Val Lys Phe Asn Trp Tyr Val Asp Gly Val Glu Val His
            275               280               285

Asn Ala Lys Thr Lys Pro Arg Glu Glu Gln Tyr Asn Ser Thr Tyr Arg
            290               295               300

Val Val Ser Val Leu Thr Val Leu His Gln Asp Trp Leu Asn Gly Lys
305               310               315               320

Glu Tyr Lys Cys Lys Val Ser Asn Lys Ala Leu Pro Ala Pro Ile Glu
                325               330               335

Lys Thr Ile Ser Lys Ala Lys Gly Gln Pro Arg Glu Pro Gln Val Tyr
                340               345               350

Thr Leu Pro Pro Ser Arg Asp Glu Leu Thr Lys Asn Gln Val Ser Leu
            355               360               365

Thr Cys Leu Val Lys Gly Phe Tyr Pro Ser Asp Ile Ala Val Glu Trp
            370               375               380

Glu Ser Asn Gly Gln Pro Glu Asn Asn Tyr Lys Thr Thr Pro Pro Val
385               390               395               400

Leu Asp Ser Asp Gly Ser Phe Phe Leu Tyr Ser Lys Leu Thr Val Asp
                405               410               415

Lys Ser Arg Trp Gln Gln Gly Asn Val Phe Ser Cys Ser Val Met His
                420               425               430

Glu Ala Leu His Asn His Tyr Thr Gln Lys Ser Leu Ser Leu Ser Pro
            435               440               445

Gly Lys
450

<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
```

```
                35                  40                  45

Asp Thr Ser Lys Leu Ala Ser Gly Val Pro Ala His Phe Arg Gly Ser
 50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2

<400> SEQUENCE: 3

Met Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                 85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
            115                 120                 125

Ile Ile Ser Thr Leu Thr
            130

<210> SEQ ID NO 4
<211> LENGTH: 132
<212> TYPE: PRT
<213> ORGANISM: Artificial Sequence
<220> FEATURE:
<223> OTHER INFORMATION: aldesleukin
```

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4

<400> SEQUENCE: 5

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7

<400> SEQUENCE: 6

Met Asp Cys Asp Ile Glu Gly Lys Asp Gly Lys Gln Tyr Glu Ser Val
1               5                   10                  15

```
Leu Met Val Ser Ile Asp Gln Leu Leu Asp Ser Met Lys Glu Ile Gly
            20                  25                  30

Ser Asn Cys Leu Asn Asn Glu Phe Asn Phe Lys Arg His Ile Cys
        35                  40                  45

Asp Ala Asn Lys Glu Gly Met Phe Leu Phe Arg Ala Ala Arg Lys Leu
50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
130                 135                 140

Lys Ile Leu Met Gly Thr Lys Glu His
145                 150

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15

<400> SEQUENCE: 7

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 8
<211> LENGTH: 132
<212> TYPE: PRT
<213> ORGANISM: Artificial Sequence
<220> FEATURE:
<223> OTHER INFORMATION: IL-21

<400> SEQUENCE: 8

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
            20                  25                  30

Ala Pro Glu Asp Val Glu Thr Asn Cys Glu Trp Ser Ala Phe Ser Cys
```

```
                35                  40                  45
Phe Gln Lys Ala Gln Leu Lys Ser Ala Asn Thr Gly Asn Asn Glu Arg
        50                  55                  60

Ile Ile Asn Val Ser Ile Lys Lys Leu Lys Arg Lys Pro Pro Ser Thr
65                      70                  75              80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
            115                 120                 125

Ser Glu Asp Ser
        130
```